(12) United States Patent
Guest

(10) Patent No.: US 11,618,878 B2
(45) Date of Patent: *Apr. 4, 2023

(54) ASEPTIC TISSUE PROCESSING METHOD, KIT AND DEVICE

(71) Applicant: INSTIL BIO (UK) LIMITED, Manchester (GB)

(72) Inventor: Ryan Dominic Guest, Manchester (GB)

(73) Assignee: INSTIL BIO (UK) LIMITED, Manchester (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/826,062

(22) Filed: May 26, 2022

(65) Prior Publication Data

US 2022/0290094 A1    Sep. 15, 2022

Related U.S. Application Data

(63) Continuation of application No. 16/477,366, filed as application No. PCT/GB2018/050088 on Jan. 12, 2018.

(30) Foreign Application Priority Data

Jan. 13, 2017  (GB) ...................................... 1700621

(51) Int. Cl.
*C12M 3/00* (2006.01)
*B01L 3/00* (2006.01)
(Continued)

(52) U.S. Cl.
CPC ............ *C12M 47/04* (2013.01); *C12M 41/48* (2013.01); *C12M 45/02* (2013.01); *C12M 45/09* (2013.01); *C12M 45/22* (2013.01)

(58) Field of Classification Search
CPC ....... C12M 45/02; C12M 45/09; C12M 47/04
See application file for complete search history.

(56) References Cited

U.S. PATENT DOCUMENTS 5,498,599 A    3/1996  Choi et al.
5,814,295 A *  9/1998  Martin, Jr. ......... A61K 39/0011
                                                    424/1.49
(Continued)

FOREIGN PATENT DOCUMENTS

CL    2019002769 A1    5/2020
EP       3674396 A1    7/2020
(Continued)

OTHER PUBLICATIONS

Huang, J. et al., "Survival, persistence, and progressive differentiation of adoptively transferred tumor-reactive T cells associated with tumor regresssion," J. Immunother., 28(3):258-267, (2005).
(Continued)

*Primary Examiner* — Nathan A Bowers
(74) *Attorney, Agent, or Firm* — Alston & Bird LLP

(57) ABSTRACT

The present invention concerns a single use aseptic kit comprising: a disaggregation module for receipt and processing of material comprising solid mammalian tissue; and a stabilisation module for storing disaggregated product material, wherein each of said modules comprises one or more flexible containers connected by one or more conduits adapted to enable flow of the tissue material there between; and wherein each of said modules comprises one or more ports to permit aseptic input of media and/or reagents into the one or more flexible containers. The invention further relates to an automated device for semi-automated aseptic disaggregation and/or enrichment and/or stabilisation of cells or cell aggregates from mammalian solid tissue comprising a programmable processor and the single use aseptic (Continued)

kit. The invention further relates to a semi-automatic aseptic tissue processing method.

15 Claims, 11 Drawing Sheets

(51) Int. Cl.
*C12M 1/00* (2006.01)
*C12M 1/36* (2006.01)
*C12M 1/33* (2006.01)

(56) References Cited

U.S. PATENT DOCUMENTS

| | | |
|---|---|---|
| 7,847,067 B2 | 12/2010 | Abo et al. |
| 8,034,334 B2 | 10/2011 | Dudley et al. |
| 8,287,857 B2 | 10/2012 | Dudley et al. |
| 8,383,099 B2 | 2/2013 | Dudley et al. |
| 8,809,050 B2 | 8/2014 | Vera et al. |
| 8,956,860 B2 | 2/2015 | Vera et al. |
| 9,074,185 B2 | 7/2015 | Dudley et al. |
| 9,567,565 B2 | 2/2017 | Vera et al. |
| 9,844,569 B2 | 12/2017 | Gros et al. |
| 10,130,659 B2 | 11/2018 | Wardell et al. |
| 10,166,257 B2 | 1/2019 | Wardell et al. |
| 10,202,454 B2 | 2/2019 | Freeman et al. |
| 10,272,113 B2 | 4/2019 | Wardell et al. |
| 10,363,273 B2 | 7/2019 | Wardell et al. |
| 10,398,734 B2 | 9/2019 | Wardell et al. |
| 10,415,015 B2 | 9/2019 | Veerapathran et al. |
| 10,420,799 B2 | 9/2019 | Wardell et al. |
| 10,435,455 B1 | 10/2019 | Sonntag et al. |
| 10,463,697 B2 | 11/2019 | Wardell et al. |
| 10,517,894 B2 | 12/2019 | Frank et al. |
| 10,533,156 B2 | 1/2020 | Vera et al. |
| 10,537,595 B2 | 1/2020 | Wardell et al. |
| 10,570,201 B2 | 2/2020 | Grosveld et al. |
| 10,639,330 B2 | 5/2020 | Wardell et al. |
| 10,646,517 B2 | 5/2020 | Wardell et al. |
| 10,653,723 B1 | 5/2020 | Wardell et al. |
| 10,695,372 B2 | 6/2020 | Wardell et al. |
| 10,894,063 B2 | 1/2021 | Wardell et al. |
| 10,905,718 B2 | 2/2021 | Wardell et al. |
| 10,918,666 B2 | 2/2021 | Wardell et al. |
| 10,925,900 B2 | 2/2021 | Wardell et al. |
| 10,933,094 B2 | 3/2021 | Wardell et al. |
| 10,946,044 B2 | 3/2021 | Wardell et al. |
| 10,946,045 B2 | 3/2021 | Wardell et al. |
| 10,953,046 B2 | 3/2021 | Wardell et al. |
| 10,953,047 B2 | 3/2021 | Wardell et al. |
| 11,007,225 B1 | 5/2021 | Wardell et al. |
| 11,007,226 B2 | 5/2021 | Wardell et al. |
| 11,013,770 B1 | 5/2021 | Wardell et al. |
| 11,026,974 B2 | 6/2021 | Frank et al. |
| 11,040,070 B2 | 6/2021 | Wardell et al. |
| 11,052,115 B2 | 7/2021 | Wardell et al. |
| 11,052,116 B2 | 7/2021 | Wardell et al. |
| 11,058,728 B1 | 7/2021 | Frank et al. |
| 11,077,182 B2 | 8/2021 | Hinrichs et al. |
| 11,083,752 B2 | 8/2021 | Wardell et al. |
| 11,123,371 B2 | 9/2021 | Frank et al. |
| 11,141,434 B2 | 10/2021 | Rabinovich et al. |
| 11,141,438 B2 | 10/2021 | Frank et al. |
| 11,168,303 B2 | 11/2021 | Wardell et al. |
| 11,168,304 B2 | 11/2021 | Wardell et al. |
| 11,179,419 B2 | 11/2021 | Frank et al. |
| 11,202,803 B1 | 12/2021 | Wardell et al. |
| 11,202,804 B2 | 12/2021 | Wardell et al. |
| 11,220,670 B2 | 1/2022 | Simpson-Abelson et al. |
| 11,241,456 B2 | 2/2022 | Wardell et al. |
| 11,254,913 B1 | 2/2022 | Wardell et al. |
| 11,266,694 B2 | 3/2022 | Frank et al. |
| 11,273,180 B2 | 3/2022 | Wardell et al. |
| 11,273,181 B2 | 3/2022 | Wardell et al. |
| 11,291,687 B2 | 4/2022 | Wardell et al. |
| 11,293,009 B2 | 4/2022 | Simpson-Abelson et al. |
| 11,304,979 B2 | 4/2022 | Wardell et al. |
| 11,304,980 B2 | 4/2022 | Frank et al. |
| 11,311,578 B2 | 4/2022 | Frank et al. |
| 11,337,998 B2 | 5/2022 | Wardell et al. |
| 11,344,579 B2 | 5/2022 | Wardell et al. |
| 11,344,580 B2 | 5/2022 | Frank et al. |
| 11,344,581 B2 | 5/2022 | Frank et al. |
| 11,351,197 B2 | 6/2022 | Frank et al. |
| 11,351,198 B2 | 6/2022 | Frank et al. |
| 11,351,199 B2 | 6/2022 | Frank et al. |
| 11,357,841 B2 | 6/2022 | Ritthipichai et al. |
| 11,364,266 B2 | 6/2022 | Frank et al. |
| 11,369,637 B2 | 6/2022 | Frank et al. |
| 11,384,337 B2 | 7/2022 | Chartier-Courtaud et al. |
| 11,401,507 B2 | 8/2022 | Simpson-Abelson et al. |
| 11,433,097 B2 | 9/2022 | Fardis |
| 2002/0168759 A1 | 11/2002 | Wang et al. |
| 2009/0258417 A1* | 10/2009 | Tanaka .................. C12M 23/04 435/325 |
| 2012/0244133 A1 | 9/2012 | Rosenberg et al. |
| 2013/0102075 A1 | 4/2013 | Vera et al. |
| 2013/0115617 A1 | 5/2013 | Wilson |
| 2014/0047572 A1 | 2/2014 | Chen et al. |
| 2014/0050708 A1 | 2/2014 | Powell et al. |
| 2014/0099309 A1 | 4/2014 | Powell et al. |
| 2015/0119351 A1 | 4/2015 | Lubin et al. |
| 2016/0208216 A1 | 7/2016 | Vera et al. |
| 2017/0191035 A1* | 7/2017 | Sia ......................... A61K 35/35 |
| 2018/0057592 A1 | 3/2018 | Frazier et al. |
| 2018/0127715 A1 | 5/2018 | Veerapathran et al. |
| 2018/0133253 A1 | 5/2018 | Gros et al. |
| 2018/0180601 A1 | 6/2018 | Pedersen et al. |
| 2018/0200367 A1 | 7/2018 | Borrello et al. |
| 2018/0207201 A1 | 7/2018 | Wardell et al. |
| 2018/0228841 A1 | 8/2018 | Frank et al. |
| 2018/0250338 A1* | 9/2018 | He ......................... A61K 33/243 |
| 2018/0280436 A1 | 10/2018 | Wardell et al. |
| 2018/0282694 A1 | 10/2018 | Wardell et al. |
| 2018/0325954 A1 | 11/2018 | Wardell et al. |
| 2019/0000882 A1 | 1/2019 | Wardell et al. |
| 2019/0000883 A1 | 1/2019 | Wardell et al. |
| 2019/0032011 A1 | 1/2019 | Better et al. |
| 2019/0040111 A1 | 2/2019 | Tran et al. |
| 2019/0070222 A1 | 3/2019 | Wardell et al. |
| 2019/0083536 A1 | 3/2019 | Wardell et al. |
| 2019/0083538 A1 | 3/2019 | Wardell et al. |
| 2019/0083539 A1 | 3/2019 | Wardell et al. |
| 2019/0085046 A1 | 3/2019 | Yoseph et al. |
| 2019/0085047 A1 | 3/2019 | Hinrichs et al. |
| 2019/0085063 A1 | 3/2019 | Frigault et al. |
| 2019/0136230 A1 | 5/2019 | Sather et al. |
| 2019/0177395 A1 | 6/2019 | Tran et al. |
| 2019/0177692 A1 | 6/2019 | June et al. |
| 2019/0231820 A1 | 8/2019 | Fardis |
| 2019/0235445 A1 | 8/2019 | Han et al. |
| 2019/0276802 A1 | 9/2019 | Simpson-Abelson et al. |
| 2019/0298770 A1 | 10/2019 | Rabinovich et al. |
| 2019/0322722 A1 | 10/2019 | Sonntag et al. |
| 2019/0345445 A1 | 11/2019 | Veerapathran et al. |
| 2019/0358259 A1 | 11/2019 | Wardell et al. |
| 2019/0358260 A1 | 11/2019 | Wardell et al. |
| 2019/0358261 A1 | 11/2019 | Wardell et al. |
| 2019/0374577 A1 | 12/2019 | Ritthipichai et al. |
| 2020/0000904 A1 | 1/2020 | McGranahan et al. |
| 2020/0024161 A1 | 1/2020 | Ramunni et al. |
| 2020/0032197 A1 | 1/2020 | Guest et al. |
| 2020/0056237 A1 | 2/2020 | Lu et al. |
| 2020/0095548 A1 | 3/2020 | Gros et al. |
| 2020/0095550 A1 | 3/2020 | Vera et al. |
| 2020/0121719 A1 | 4/2020 | Lotze et al. |
| 2020/0155601 A1 | 5/2020 | Wardell et al. |
| 2020/0157241 A1 | 5/2020 | Morgan et al. |
| 2020/0206265 A1 | 7/2020 | Perez et al. |
| 2020/0208086 A1 | 7/2020 | Quick et al. |
| 2020/0224161 A1 | 7/2020 | Karyampudi et al. |
| 2020/0246384 A1 | 8/2020 | Wardell et al. |
| 2020/0247869 A1 | 8/2020 | Tran et al. |
| 2020/0263130 A1 | 8/2020 | Bridgeman |

(56) References Cited

U.S. PATENT DOCUMENTS

| | | |
|---|---|---|
| 2020/0276241 A1 | 9/2020 | Wardell et al. |
| 2020/0276242 A1 | 9/2020 | Wardell et al. |
| 2020/0277573 A1 | 9/2020 | Simpson-Abelson et al. |
| 2020/0281978 A1 | 9/2020 | Wardell et al. |
| 2020/0289569 A1 | 9/2020 | Wardell et al. |
| 2020/0289570 A1 | 9/2020 | Moriarity et al. |
| 2020/0299644 A1 | 9/2020 | Frank et al. |
| 2020/0306306 A1 | 10/2020 | Wardell et al. |
| 2020/0306307 A1 | 10/2020 | Wardell et al. |
| 2020/0306310 A1 | 10/2020 | Moriarity et al. |
| 2020/0316121 A1 | 10/2020 | Deniger et al. |
| 2020/0347350 A1 | 11/2020 | Karyampudi et al. |
| 2021/0000872 A1 | 1/2021 | Price et al. |
| 2021/0079348 A1 | 3/2021 | Wardell et al. |
| 2021/0100842 A1 | 4/2021 | Wardell et al. |
| 2021/0100843 A1 | 4/2021 | Wardell et al. |
| 2021/0106625 A1 | 4/2021 | Wardell et al. |
| 2021/0123020 A1 | 4/2021 | Simpson-Abelson et al. |
| 2021/0128620 A1 | 5/2021 | Wardell et al. |
| 2021/0128621 A1 | 5/2021 | Wardell et al. |
| 2021/0128622 A1 | 5/2021 | Wardell et al. |
| 2021/0128623 A1 | 5/2021 | Wardell et al. |
| 2021/0128624 A1 | 5/2021 | Wardell et al. |
| 2021/0128625 A1 | 5/2021 | Wardell et al. |
| 2021/0130779 A1 | 5/2021 | Chartier-Courtaud et al. |
| 2021/0137930 A1 | 5/2021 | Fardis |
| 2021/0137984 A1 | 5/2021 | Wardell et al. |
| 2021/0145877 A1 | 5/2021 | Fardis |
| 2021/0187029 A1 | 6/2021 | Lotze et al. |
| 2021/0189339 A1 | 6/2021 | Simpson-Abelson et al. |
| 2021/0205365 A1 | 7/2021 | Price et al. |
| 2021/0207091 A1 | 7/2021 | Wardell et al. |
| 2021/0207092 A1 | 7/2021 | Wardell et al. |
| 2021/0214685 A1 | 7/2021 | Wardell et al. |
| 2021/0252062 A1 | 8/2021 | Frank et al. |
| 2021/0252063 A1 | 8/2021 | Frank et al. |
| 2021/0260121 A1 | 8/2021 | Frank et al. |
| 2021/0274776 A1 | 9/2021 | Veerapathran et al. |
| 2021/0279111 A1 | 9/2021 | Ranjan et al. |
| 2021/0309968 A1 | 10/2021 | Simpson-Abelson et al. |
| 2021/0335467 A1 | 10/2021 | Brooks et al. |
| 2021/0353677 A1 | 11/2021 | Wardell et al. |
| 2021/0361712 A1 | 11/2021 | Wardell et al. |
| 2021/0361713 A1 | 11/2021 | Wardell et al. |
| 2021/0369775 A1 | 12/2021 | Fardis et al. |
| 2021/0379111 A1 | 12/2021 | Wardell et al. |
| 2021/0401889 A1 | 12/2021 | Frank et al. |
| 2021/0407639 A1 | 12/2021 | Brooks et al. |
| 2021/0407640 A1 | 12/2021 | Brooks et al. |
| 2022/0000923 A1 | 1/2022 | Wardell et al. |
| 2022/0000924 A1 | 1/2022 | Wardell et al. |
| 2022/0000925 A1 | 1/2022 | Wardell et al. |
| 2022/0000926 A1 | 1/2022 | Frank et al. |
| 2022/0000927 A1 | 1/2022 | Frank et al. |
| 2022/0000928 A1 | 1/2022 | Frank et al. |
| 2022/0000929 A1 | 1/2022 | Frank et al. |
| 2022/0008469 A1 | 1/2022 | Wardell et al. |
| 2022/0008470 A1 | 1/2022 | Frank et al. |
| 2022/0010278 A1 | 1/2022 | Chartier-Courtaud et al. |
| 2022/0025052 A1 | 1/2022 | Rabinovich et al. |
| 2022/0033775 A1 | 2/2022 | Chartier-Courtaud et al. |
| 2022/0059202 A1 | 2/2022 | Brooks et al. |
| 2022/0072039 A1 | 3/2022 | Fardis |
| 2022/0088069 A1 | 3/2022 | Fardis et al. |
| 2022/0088080 A1 | 3/2022 | Frank et al. |
| 2022/0088081 A1 | 3/2022 | Frank et al. |
| 2022/0090018 A1 | 3/2022 | Wardell et al. |
| 2022/0096555 A1 | 3/2022 | Frank et al. |
| 2022/0112557 A1 | 4/2022 | Chartier-Courtaud et al. |
| 2022/0118011 A1 | 4/2022 | Wardell |
| 2022/0118012 A1 | 4/2022 | Fardis et al. |
| 2022/0122707 A1 | 4/2022 | Brooks et al. |
| 2022/0133795 A1 | 5/2022 | Karyampudi |
| 2022/0133798 A1 | 5/2022 | Frank et al. |
| 2022/0160760 A1 | 5/2022 | Bridgeman et al. |
| 2022/0193131 A1 | 6/2022 | Chartier-Courtaud et al. |
| 2022/0204932 A1 | 6/2022 | Chartier-Courtaud et al. |
| 2022/0249559 A1 | 8/2022 | Wardell |
| 2022/0313806 A1 | 10/2022 | Simpson-Abelson |
| 2022/0315892 A1 | 10/2022 | Veerapthran |
| 2022/0315893 A1 | 10/2022 | Veerapthran |
| 2022/0322655 A1 | 10/2022 | Veerapathran et al. |

FOREIGN PATENT DOCUMENTS

| | | |
|---|---|---|
| WO | 95/18858 A1 | 7/1995 |
| WO | 96/17060 A1 | 6/1996 |
| WO | WO-9923199 A1 * | 5/1999 |
| WO | 2004/021995 A2 | 3/2004 |
| WO | 2008/136843 A1 | 11/2008 |
| WO | 2011/072088 A2 | 6/2011 |
| WO | 2012/129201 A1 | 9/2012 |
| WO | 2013/173835 A1 | 11/2013 |
| WO | 2013/188427 A1 | 12/2013 |
| WO | 2014/133568 A1 | 9/2014 |
| WO | 2015/009604 A1 | 1/2015 |
| WO | 2015/123527 A1 | 8/2015 |
| WO | 2015/188839 A2 | 12/2015 |
| WO | 2017/103596 A1 | 6/2017 |
| WO | 2017/179015 A1 | 10/2017 |
| WO | 2018/009894 A1 | 1/2018 |
| WO | 2018/014039 A1 | 1/2018 |
| WO | 2018/081473 A1 | 5/2018 |
| WO | 2018/081789 A1 | 5/2018 |
| WO | 2018/094167 A1 | 5/2018 |
| WO | 2018/129332 A1 | 7/2018 |
| WO | 2018/129336 A1 | 7/2018 |
| WO | 2018/182817 A1 | 10/2018 |
| WO | 2018/209115 A1 | 11/2018 |
| WO | 2018/226714 A1 | 12/2018 |
| WO | 2019/100023 A1 | 5/2019 |
| WO | 2019/103857 A1 | 5/2019 |
| WO | 2019/118873 A2 | 6/2019 |
| WO | 2019/136456 A1 | 7/2019 |
| WO | 2019/136459 A1 | 7/2019 |
| WO | 2019/145711 A1 | 8/2019 |
| WO | 2019/157130 A1 | 8/2019 |
| WO | 2019/160829 A1 | 8/2019 |
| WO | 2019/190579 A1 | 10/2019 |
| WO | 2019/210131 A1 | 10/2019 |
| WO | 2019/217753 A1 | 11/2019 |
| WO | 2019/243835 A1 | 12/2019 |
| WO | 2020/061429 A1 | 3/2020 |
| WO | 2020/096682 A2 | 5/2020 |
| WO | 2020/096927 A1 | 5/2020 |
| WO | 2020/096986 A2 | 5/2020 |
| WO | 2020/096988 A2 | 5/2020 |
| WO | 2020/096989 A1 | 5/2020 |
| WO | 2020/114491 A1 | 6/2020 |
| WO | 2020/117233 A1 | 6/2020 |
| WO | 2020/131547 A1 | 6/2020 |
| WO | 2020/146740 A1 | 7/2020 |
| WO | 2020/152451 A1 | 7/2020 |
| WO | 2020/180733 A1 | 9/2020 |
| WO | 2020/232029 A1 | 11/2020 |
| WO | 2021/014174 A1 | 1/2021 |
| WO | 2021/081378 A1 | 4/2021 |
| WO | 2021/118990 A1 | 6/2021 |
| WO | 2021/123555 A1 | 6/2021 |
| WO | 2021/123832 A1 | 6/2021 |
| WO | 2021/216920 A1 | 10/2021 |
| WO | 2021/226061 A1 | 11/2021 |
| WO | 2021/226085 A1 | 11/2021 |
| WO | 2022/016112 A1 | 1/2022 |
| WO | 2022/016114 A1 | 1/2022 |
| WO | 2022/076606 A1 | 4/2022 |
| WO | 2022/076952 A1 | 4/2022 |
| WO | 2022/087324 A1 | 4/2022 |
| WO | 2022/125941 A1 | 6/2022 |
| WO | 2022/130015 A2 | 6/2022 |
| WO | 2022/130016 A1 | 6/2022 |
| WO | 2022/130017 A2 | 6/2022 |
| WO | 2022/133140 A1 | 6/2022 |
| WO | 2022/133149 A1 | 6/2022 |

(56) References Cited

FOREIGN PATENT DOCUMENTS

| WO | 2022/147196 A2 | 7/2022 |
|---|---|---|
| WO | 2022/165260 A1 | 8/2022 |
| WO | 2022/170219 A1 | 8/2022 |
| WO | 2022/187741 A2 | 9/2022 |
| WO | 2022/198141 A1 | 9/2022 |
| WO | 2022/204155 A1 | 9/2022 |
| WO | 2022/204564 A2 | 9/2022 |

OTHER PUBLICATIONS

Hulen, Thomas Morgan et al., "ACT Up TIL Now: The Evolution of Tumor-Infiltrating Lymphocytes in Adopted Cell Therapy for the Treatment of Solid tumors," Immuno, 1:194-211, (2011).

Ikarashi, H., et al., "Solid-phase anti-CD3 antibody activation and cryopreservation of human tumor-nifiltrating lymphocytes derived from epithelial ovarian cancer," Jpn. J. Cancer Res., 83(12):1359-1365, (1992).

Imai et al., "Expression of multiple immune checkpiont molecules on T cells in malignant ascites from epithelial ovarian carcinoma," Oncol. Left., 15(5):6457-6468, (Feb. 21, 2018).

International Preliminary Report on Patentability received for PCT Patent Application No. PCT/GB2019/050188, dated Aug. 6, 2020, 8 pages.

International Search Report and Written Opinion received for PCT Patent Application No. PCT/GB2018/050088, dated Apr. 19, 2018, 9 pages.

International Search Report and Written Opinion received for PCT Patent Application No. PCT/GB2019/050188, dated Apr. 11, 2019, 10 pages.

Iovance Biotherapeutics , "Iovance Biotherapeutics Announces Updates to tumor infiltrating lymphcoyte (TIL) therapy clinical programs," Press Release, 2 pgs., May 15, 2019.

Iovance Biotherapeutics , "Iovance Biotherapeutics Announces Updated Phase 2 Clinical Data form the Lifileucel Metastatic Melanomo Trail at the Society for Immunotherapy of Cancer 34th Annual Meeting," Press Release , 2 pgs., Nov. 8, 2019.

Iovance Biotherapeutics , "Journal of Clinical Oncology Publishes Clinical Data for Cohort 2 in Iovance C-144-01 Study of Lifileucel TIL-Therapy in Metastatic Melanomo," Press Release, 2 pgs., May 12, 2021.

Iovance Biotherapeutics , "Lion Biotechnologies Announces First Patient Dosed in Second Cohort of LN-144 Phase 2 Trail for Metastatic Melonomo," Press Release , 2 pgs., May 19, 2017.

Iovance Biotherapeutics , "Updated Results of Studies in Advanced Cervical Cancer and Melanomo Support Long-Term Efficacy of IovanceTumor Infiltrating Lymphoctye (TIL) Therapy," Press Release, 3 pgs., May 31, 2019.

Iovance Biotherapeutics , Cohort 2 by Invastigator, Responders Previously Progressed on Checkpoint Inhibitors, Chart, 1 pgs., (2020).

Iovance Biotherapeutics, "Iovance Biotherapeutics Announces reports results form FDA end of Phase 2 meeting and provides updates about the company's clinical program," Press Release, 3 pgs., Oct. 11, 2018.

Iovance Biotherapeutics, "Iovance Biotherapeutics Announces 33-Month Follow Up Date for Lifileucel in Advanced Melanoma at ASCO 2021 Annual Meeting," Press Release, 2 pgs., Jun. 6, 2021.

Iovance Biotherapeutics, "Iovance Biotherapeutics Announces Clinical Date for LN-145 in Non-Small Cell Lung Cancer," Press Release, 2 pgs., Jun. 29, 2021.

Iovance Biotherapeutics, "Iovance Biotherapeutics Announces Clinical Date Updates for Lifileucel in Advancer Melanoma at Upcoming ASCO 2021 Annual Meeting," Presss Release. 2 pgs., May 19, 2021.

Iovance Biotherapeutics, "Iovance Biotherapeutics Announces Clinical Date Updates for Lifileucel in Advancer Melanoma During American Asssociation for Cancer Research (AACR) 2021 Annual Meeting," Press Release, 3 pgs., Apr. 9, 2021.

Iovance Biotherapeutics, "Iovance Biotherapeutics Announces New LN-144 Phase 2 Clinical Data from Metastatic Melanoma Trial to be Presented at SITC Meeting," Press Release, 5 pgs, Nov. 9, 2017.

Iovance Biotherapeutics, "Iovance Biotherapeutics announces Preliminary Phase 2 Dada for TIL Treatment in Head and Nerk and Cervical Cancers," Press Release, 3 pgs, Jan. 24, 2018.

Itzhaki, O., et al., "Establishment and large-scale expansion of minimally cultured "young" tumor infiltrating lymphocytes for adoptive transfer therapy," J. Immunother., 34 (2):212-220, (2011).

Janakiram, M. et al., "Tumor infiltrating lymphocytes as a prognostic and pridictive biomaker in breast cancer," Moleculer Pathlogy of Breast Cancer, 12:1-20, (2016).

Jang et al., "Characterization of T cell reperoire of blood, tumor, and ascites in ovarian cancer patients using next generation sequencing," Oncoimmunology, 4(11):e1030561, (2015).

Jansen, Caroline S. et al., "AN Intra-tumoral niche maintains and diffrentiates stem-like CD8 T cells," Nature, 576:465-470, (2019).

Jazaeri Amir A. et al., Safety and efficacy of adoptive, cell transfer using autologus tumor infiltrating lymphocytes (LN-145) for treatment of recurrent, metastatic, or persistent cervical carcinoma, 182 ASCO Annual Meeting, Chicago, IL, (May 31-Jun. 4, 2019).

Jazaeri Amir A. et al., Safety and efficacy of adoptive, cell transfer using autologus tumor infiltrating lymphocytes (LN-145) for treatment of recurrent, metastic, or persistent cervical carcinoma, J. Clin. Oncol., 37:Suppl., Abstract 2538, (2019).

Jazaeri, Amir, "In vivo persistence of Iovance tumour-infiltrating lymphocytes LN-145 in cervical cancer patients," 3688 ESMO Virtual Congress, (Sep. 19-21, 2020).

Jazaeri, Amir, "In vivo persistence of Iovance tumour-infiltrating lymphocytes LN-145 in cervical cancer patients," Iovance Biotherapeutics, Inc., 873P, Abstract, (2020).

Jazaeri, Amir, "Trial in Progress: A Phase 2, Multicenter Study to Evaluate the Efficacy and Safety Using Autologus Tumor Infiltrating Lymphocytes (LN-145) in Patients with Recurrent, Metastatic, or Presistent Cervical Carcinoma," 329a ASCO Annual Meeting, McCromick Place, Chicago, IL (Jun. 1-5, 2018).

Jazaeri, Amir, "A Phase 2, multicentre study to evaluate the efficacy and safety of using autologous tumor infiltrating lymphocytes (LN-145) in patients with recurrent, metastatic, or persistent cervical carcinomo," P220 SITC Annual Meeting, National Harbor, MD, (Nov. 8-12, 2017).

Jespersen, Henrik et al., "Clinical responses to adoptive T-cell transfer can be modeled in an autologous immune-humanized mouse model," Nature Communications, 8:707, (2007).

Jiang, Li et al., "Ovarian Cancer-Intrinsic Fatty Acid Synthase Prevents Anti-tumor Immunity By Disrupting Tumor-Infillrating Dendritic Cells," Frontiers in immunology, 9:2927, (2018).

Jiang, Peng et al., "Signatures of T cell dysfunction and exclusion predict cancer immunotherapy response," Nature Medicine, 24:1550-1558, (2018).

Jimenez-Reinoso, A., et al., "Synthetic TILs: Engineered Tumor-Infiltrating Lymphocytes With Improved Therapeutic Potential," Front. Oncol., 10:593848, (2021).

Jin et al., 2012, Simplified method of the gmvvth of human tumor infiltrating lymphocytes (TIL) in gas-permeable flasks to numbers needed for patient treatment J, Immunother. 35:283.

Jin, Jianjian et al., "Simplified Method of the Growth of Human Tumor Infiltrating Lymphocytes in Gas-permeable Flasks to Number Needed for Patient Treatment," J Immunother. 35(3):283-292, (2012).

Jinghua, Lu et al., "Molecular Constraints on CDR3 For Thymic Selection of MHC-restricted TCRs From a Random Pre-selection Repertoire," Nature Communications, 10:1-14, (2019).

Jones, E. Yvonne, "Designer protein delivers signal of choice," Nature, 565:165-166, (Jan. 10, 2019).

Kalaora, Shelly et al., "Combined analysis of Antigen Presentation and T-cell Recognition Reveals Restricted Immune Responses in Melanoma," Cancer Discov 8(11): 1366-1375, (2018).

Kallies, Axel et al., "Precursor exhausted T cells: key to successful immunotherapy?" Nature Reveiws Immunology, 20:128-136, (2020).

Kao, Yun-Ruei et al., "Thermbopoietin receptor-independent stimulation of hematopoietic stem cells by eltrombopag," Sci. Transl. med., 10:eaas9563, (2018).

(56) References Cited

OTHER PUBLICATIONS

Kappler, John et al., "Pillars Article: The Major Histocompatibility Complex-restricted Antigen Receptor on T Cells in Mouse and Man: Identification of Constant and Variable Peptides," Cell, 35:295-302, (1983).
Karyampudi, Lavakumar et al., "Iovance Peripheral Blood Lymphocytes (PBL): A Potential Cell Therapy Strategy for the Treatment of Chronic Lymphocytic Leukemia," PF447 EHA Annual Meeting, RAI Amsterdam, Amsterdam, Netherlands, (Jun. 13-16, 2019).
Karyampudi, Lavakumar et al., "Phenotypic and functional characterization of tumor infiltrating lymphocytes (TIL) grown from non-hodgkin lymphoma tumor-implications fot the development of novel therapies for lymphoma," ESMO Annual Meeting, Madrid, Spain, (Sep. 7-12, 2017).
Kawahara et al., "Engineering of mammalian cell membrane proteins," Curr. Opin Chem. Eng., 1:411-417, (2012).
Kawahara et al., Growth promotion of genetically modified hematopoietic progenitors using an antibody/c-MpI chimera. Cytokine, 55(3):402-408, (2011).
Kawahara, Masahiro et al., "Engineering cytokine receptors to control cellular functions," Biochemical Engineering Journal, 48:283-294, (2010).
Kershaw, Michael H. et al., "A Phase I Study on Adoptive Immunotherapy Using Gene-Modified T Cells for Ovarian Cancer," Clin Cancer Res, 12:6106-6115, (2006).
Khalil, Danny N. et al., "In situ vaccination with defined factors overcomes T cell exhaustion in distant tumors," J. Clin. Invest., 129:3435-3447, (2019).
Khan, Omar et al., "TOX transcriptionally and epigenetically programs CD8+ T cell exhaustion," Nature, 571:211-218, (2019).
WIPO Application No. PCT/US22/34606, PCT Invitation to Pay Additional Fees and, Where Applicable, Protest Fee mailed Sep. 9, 2022.
Wong, Sandi, "Lovance shoes autologous tumor-infiltrating lymphocytes effective after anti-PD-1,"BioCentury,[Retrived from the internet Nov. 23, 2019: ,URL:https:www.biocentury.com/article/303797/iovance-show-autologous-tumor-infliltration-lymphocytes-effective-after-anti-pd-1x.].
Wu, Ning et al., "SLAM family receptor in normal immunity and immune pathologies," Current Opinion in Immunology, 38:45-51, (2016).
Wu, R., et al., "Adoptive T cell therapy using autologous tumor-inflitrating lmphocytes for mtastatic melanoma: current status and future outlook," Cancer J., 18(2): 160-175, (2012).
Xia et al., "T Cell Dysfunction in Cancer Immunity and Immunotherapy," Front. Immunol., 10:1719, (Jun. 19, 2019).
Yamane, Noriko et al., "Characterization of novel non-peptide thrombopoietin receptor," European Journal of Pharmacology, 586:44-51, (2008).
Yang, S., et al., "A Simplified Method for the Clinical-scale Generation of Central Memory-like CD8+ T Cells After Transduction With Lentiviral Vectors Encoding Antitumor Antigen T-cell Receptors," J. Immunother., 33(6):648-658 (2010).
Yannelli, J.R. et al., "Growht of tumor-infiltrating lymphocytes form human solid cancer: summary of a 5-year experience," Int. J. Cancer, 65(4):413-421, (1996).
Ye, Q., et al., "Engineered artificial antigen presenting cells facilitate direct and efficient expansion of tumor infiltrating lymphocytes," J. Transl. Med., 9:131, (2011).
Ye, Qunrui et al., "Activation-induced CD137 expression accurately identifies naturally occurring tumor-reactive T cells in cancer patients," OncoImmunology, 2:12, e27184, (Dec. 2013).
Ye, Qunrui et al., "CD137 Accurately Identifies and Enriches for Naturally Occurring Tumor-Reactive T Cells in Tumor," Clin Cancer Res., 20:44-55, (2014).
Yee, C. et al., "Adoptive T cell therapy using antigen-specific CD8+ T cell clones for the treatment of patients with metastatic melanoma: In vivo persistence, migration, and antitumor effect of transferred T cells," PANS, 99:16168-16173, (Dec. 10, 2002).
Yigit, Burcu et al., "SLAMF6 as a Regulator of Exhausted CD8+ T Cells in Cancer," Cancer Immunology Res., 7(9):1485-1496 (2019).
Yong-Chen, Lu et al., "An Efficient Single-Cell RNA-Seq Approach to Identify Neoantigen-Specific T Cell Receptors," Mol. Ther., 26(2):379-389 (2018).
Yossef, Rami et al., "Abstract B055; Enhanced detection of T-cells targeting unique neoantigens and shared muted oncogenes for personalized cancer immunotherapy," Cancer Immunol. Res., 7(2):B055, Supplement, (2019).
Yost, Kathryn E. et al., "Clonal replacement of tumor-specific T cells following PD-1 blockade," 25:1251-1259, (2019).
Yron, I., et al., "In vitro growth of murine T cells. V. The isolation and growth of lymphoid cells infiltrating syngeneic solid tumore," J. Immuol., 125(1):238-245, (1980).
Yu, Peng-Cheng et al., "Association between density of tumor-infiltrating lymphocytes and prognoses of patients with gastric cancer," Medicine, 97(27):1-8, (2018).
Zacharakis, Nikolaos et al., "Breast Cancers Are Immunogenic: Immunologic Analyses and a Phase II Piolot Clinical Trial Using Mutation-Reactive Autologous Lymphocytes," J Clin. Oncol., 40:1741-1754, (Feb. 2, 2022).
Zacharakis, Nikolaos et al., "Immune recognition of somatic mutations leading to complete durable regression in metastatic breast cancer," Nature Medicine, 24:724-730, (2018).
Zgura, Anca et al., Relationship between Tumor Infiltrating Lymphocytes and Progression in Breast Cancer, Maedica (Bucur). Dec. 2018; 13(4): 317-320.
Zhang, Ling et al., "Tumor-infiltrating lymphocytes genetically engineered with an inducible gene encoding interleukin-12 for the immunotherapy of metastatic melanoma," Clin Cancer Res., 21(10):2278-2288, (May 2015).
Zhang, Shu-Qi et al., "High-throughput determination of the antigen specificities of T cell receptors in single cells," Nature Biotechnology, 36:1156-1159, (2018).
Zhao, L., et al., "Engineered T Cell Therapy for Cancer in the Clinic," Front. Immunol., 10:2250, (2019).
Zhao, Yan-Jie et al., "Expression of PD-1 on CD4+ Tumor-Infiltrating Lymphocytes in Tumor Microenvironment Asssociated with Pathological Characteristics of Breast Cancer," J Immunol. Res., 2018:1-18, (2018).
Zheng, Chunhong et al., "Landscape of Infiltrating T Cells in Liver Cancer Revealed by Single=Cell Sequencing," Cell, 169:1342-1356, (2017).
Zhou et al., "Characterization of T-Cell Memory Phenotype after in Vitro Expansion of Tumor-infiltrating Lymphocytes from Melanoma Patients," Anticancer Res., 31(12):4099-4109, (Dec. 2011).
Zhou, J., et al., "Persistence of multiple tumor-specific T-cell clones is associated with complete tumor regression in a melanoma patient receiving adoptive cell transfer therapy," J Immnuother., 28(1):53-62, (2005).
Zhou, J., et al., "Selective growth, in vitro and in vivo, of individual T cell clones from tumor-infiltrating lymphocytes obtained from patients with melanoma," J. Immunol., 173(12):7622-7629, (2004).
Zidlik, Vladimir et al., "Tumor infiltrating lymphocytes in malignant melanoma-allies or foes?," Biomed Pap Med Fac Univ Palacky Olomouc Czech Repub., 164(1):43-48, (2020).
U.S. Appl. No. 16/477,366, filed Jul. 11, 2019, 2020/0032197, Pending.
U.S. Appl. No. 17/826,053, filed May 26, 2022, Pending.
PCT/GB18/050088, Jan. 12, 2018, 2018/130845, Expired.
Kim Peter et al., "Adoptive T Cell Therapy Targeting Somatic P53 Mutations," J Immunother Cancer, 8: A165, (2020).
Kirken, Robert A. et al., "Activation of JAK3, but not JAK1, is Critical for IL-2-induced Proliferation and STAT5 Recruitment by a COOH-Terminal Region of the IL-2 receptor β-Chain," Cytokine, 7:689-700, (1995).
Kivimae, Saul et al., "Harnessing the innate and adaptive immune system to eradicate treated and distant untreated solid tumors," Society for Immunotherapy of Cance 2017 Annual Meeting, Poster #P275, (2017).
Klapper et al. (J Immunol Methods. Jun. 30, 2009; 345(1-2): 90-99. doi:10.1016/j.jim.2009.04.009.) (Year: 2009).

(56) References Cited

OTHER PUBLICATIONS

Klapper, J. A. et al., "Thoracic mastectomy for adoptive immunotherapy of melanoma: a single-institution experience," J. Thorac. Cardiovasc. Surg., 140(6):1276-1282, (2010).

Kotsakis, Athanosios et al., "Myeloid-derived supperssor cell measurements in fresh and cryporeserved blood samples," JIM, 381(102):14-22, (2012).

Kovacsovics-Bankowski et al., "Detailed characterization of tumor infiltrating lymphocytes in two distinct human solid malignancies show phenotypic similarities," J Immunother. Cancer, 2(1):38, (2014).

Krause, Anja et al., "Antigen-dependent CD28 Signaling Selectively Enhances Survival and Proliferation in Genetically Modified Actived Human Primary T Lymphocytes," J. Exp. Med., 188:619-626, (1998).

Kreher, Christian R. et al., "CD4+ and CD8+ cells in cryopreserved human PBMC maintain full functionality in cytokine ELISPOT assays," JIM, 278:79-93, (2003).

Krishna, Sri et al., "Stem-like CD8 T cells Mediate Response of Adoptive Cell immunotherapy Against Human Cancer," Science, 370:1328-1334, (2020).

Kurtulus, Sema et al., "Checkpoint Blockade Immunotherapy Induces Dynamic Changes in PD-1-CD8+ Tumor-Infiltrating T Cells," Immunity, 50:1-14, (2019).

Kvernelan, Anders Handrup et al., "Adoptive cell therapy with tumor-infiltrating lymphocytes supported by checkpoint inhibition across multiple solid cancer types," Journal for ImmunoTherapy of Cancer, 9:e003499 (2021).

Kvemeland etal. (Journal for ImmunoTherapy of Cancer 2021; 9:e003499. doi:10.1136/jitc-2021-003499) (Year: 2021).

Kvistborg, Pia et al., "TIL therapy broadens the tumor-reactive CD8+ T cell compartment in melanoma patients," OncoImmunology, 1:409-418, (2012).

Lanits, Evripidis et al., Chimeric antigen receptor T Cells with dissociated signaling domains exhibit focused antitumor activity with reduced potential for toxicity In Vivo, Cancer Immunol. Res., 1(1):43-53, (2013).

Lauss, Martin et al., "Mutational and Putatve neoantigen load predict clinical benefit of adoptive T cell therapy in melanoma," Nature Communications 8:1738, (2017).

Lazear, Eric., et al., "Targeting of IL-2 to cytotoxic lymphocytes as an improved method of cytokine-driven immuntherapy," Oncoimmunology,1265721:1-3, (2017).

Lazier, Eric et al., "Novel Immuno-oncology Strategy for targeted cytotoxic Lymphocyte Activation," Courier Therapeutics, Universty of Verginia,1 pg ., (2017).

Lee S. et al., "Tumor-Infiltrating lymphocytes in malenoma," Curr. on Call Rep., 14(5):468-474, (2012).

Lee, Sylvia, et al., "Phase 2 Study to Assess the Efficacy and Safety of autologous Tumor Infiltrating Lymphocytes (LN)145 Alone and in combination with Anti PD-L1 Inhibitor Durvamulab (Medi14736) in Patients of loaclly Advanced or Metastic Non -Small Cell Lung Cancer(NSCLC)," 318a ASCO Annual Meeting ,McCormick Place, Chicago, IL (Jun. Jan. 15, 2018).

Leidner R, "A phase 2 study to evaluate the safesty and efficacy of using autologous tumor infiltrating lympho cytes (LN-145)in patents with recurrent and /or metastatic squamous cell carcinoma of the head and neck," P221 SITC Annual Meeting, National Harbor, MD, (Nov. 8-12, 2017).

Letourneo Seven et al., "IL-2/anti-IL-2 antibody complexes show string biological activity by avoiding interaction with IL-2 receptor alpha subunit CD25," PNAS, 107(5);2171-2176, (Feb. 2, 2010).

Li Kang et al., "Superior expansion of T cells using NKG2D-targeted delivery of IL -2:Implications for adoptive T cell immunotherapy," Courier Therapeutics ,University of Vergina ,1pg (2017).

Li Qiang John et al., "Expansion of tumor-infiltrating lymphocytes (TIL) using Iovance's Gen 2 process from bladder for adoptive immuntherapy ,." A05 AACR Annual Meeting ,Denver,Co ,(May 18-21, 2019).

Li Taiwen et al., "TIMER: A Web Server for Comprehensive Analysis of Tumor-Infiltrating Immune cells." Cnacer Research. 77(21):e108-e110, (2017).

Li Xue et al., "Clonal replacement of novel T cells ;a new phenomenon in the tumor microenviroment following PD-1 blockade," Signal Transduction and Targeted Therapy, 4:43 (2019).

Li, Bo et al., "Landscape of tumor -infiltrating T cell repertoire of human cancers," Natures Genetics, 48(7):725-732, (2016).

Li, Jinyang et al., "Tumor cell Intrinsic factors Underlie Heterogeneity of Immune Cell Infiltration and Response to Immunotherapy," Immunity, 49;1-16, (2018).

Lion Biotherapeutics, Inc., "Lion Biotechnologies Announces Presentation at uocoming SITC 31st Annual Meeting," Press Release, 2 pgs., Oct. 26, 2016.

Lion Biotherapeutics, Inc., "Lion Biotechnologies Appoints Maria Fardis, PhD., as CEO," Press Release, 2pgs., Jun. 3, 2016.

Lion Biotherapeutics, Inc., "Lion Biotechnologies manufacturing capabilities and research programes unaffected by review of National Cancer Institute's Manufacturing Facilities," Press release. 1pg., Apr. 17, 2016.

Lion Biotherapeutics,Inc., "Lion Biotechnologies Announces 5-Year Extension of National Cancer Institute CRADA for Development of Novel TIL Immuno-Oncology Therapies," Press Release, 2 pgs, Aug. 24, 2016.

Lion Biotherapeutics,Inc., "Lion Biotechnologies submits investigational new drug application to conduct Phase ©study in metastatics melanoma," Press Release, 1 pg., Jan. 5, 2015.

Inozume et al., 2010, Selection of CDB+PD-1+ lymphocyles in fresh human melanomas enriches for tumor-reactive T-cells. J. Immunother. 33(9):956-64.

Lo, Winifred et al., "Immunologic recognition of a shared p53 mutated neoantigen in a patient with metastatic colorectal cancer," cancer Immunology Research, 7(4):534-543, (2019).

Lowery, F.J., et al., "Molecular signatures of antitumor neoantigen-reactive T cells from metastatics human cancers," Science, 375(6583);877-884, (2022).

Luen, Stephen J, et al., "tumour-infiltrating lymphocytes and the emerging role of immunotherapy in breast cancer," pathology, 49(2):141-155 (Feb. 2017).

Maecker,Holen T, et al., "Impact of cryopreservation on tetramer,cytokine flow cytometry and ELISPOT," BMC Immunology, 6(17):1-14 (2005).

Malekzadeh, Parisa et al., "Antigen Experienced T cell from peripheral Blood Recognize p53 Neoantigens," Clin Cancer Res., 26(6): 1267-1267, (2020).

Malekzadeh, Parisa et al., "Neoantigen screening identifies broad TP53 mutant immunogenicity in patients with epithelial cancer," J Clin Invest, 129(3):e12391, (2019).

Malone, C.C.,et al., "Characterization of human turner-infiltrating lymphocytes expanded in hollow-fiber bioreactor for immunotherapy of cancer," Cancer Biother. Radiopham., 16(5):381-390, ABSTRACT (2001). DOI: 10.1089/108497801753354285.

Mann, Thomas H. et al., "Tick-TOX, its time for T cell exhustion," Nature immunology, 20:1092-1094, (2019).

Matthys, Gemma et al., "Clinical Pharmacokinetics, platelet Response, and safety of Eltrombopag at Supartheraputic Doses of up to 200 mg once Daily in Healthy Volunteers," J Clin Pharmacol., 51:301-308, (2011).

Maus, Marcela V., "Tumour tamed by transfer of one T cell," Nature, 558:193-195, (2018).

Mavaddat, N. et al., "Signaling lymphocytic activation molecule (SLAM,CDw150) is homophillic but self-associates with very low affinity," Journal of Biological Chemistry, 275:28100-28109, (2000).

McCaffrey, J. et al., "Development of a standardised approach to in situ collection of solid tissues as starting materials for the manufacture of ATMP or cell based medicinal products," Cryotherapy, 22:S26-S186, Abstract, (2020).

McCaffrey, J. et al., "Optimisation of the cryopreservation parameters for hematopoietic and tissue derived immune cell recovery," Immetacte Ltd., 1 pg.,(2018).

McLane, Laur M. et al., "CD8 T cell Exhaustion During Chronic Viral Infection ad Cancer," Annu. Rev. Immunol., 37:457-495, (2019).

(56) References Cited

OTHER PUBLICATIONS

Met, Ozcan et al., "Principles of adoptive T cell therapy in cancer," Seminars in Immunopathology, 41:49-58, (2019).
Miller Brian C. et al., "Subsets of exhausted CD8+ T cells diffrentially mediate tumor control and respond to checkpoint blockade," Nature Immunology, 20:326-336, (Mar. 2019).
Forget, M.A., "The beneficial effects of a gas-permeable flask for expansion of Tumor-infiltrating lymphocytes as reflected in their mitochondrial function and respiration capacity." Oncoimmunology, 5(2):e1057386, (2015).
Forget, M.A., et al., "Activation and propagation of tumor-infiltrating lymphocytes on clinical-grade designer artificial antigen-presenting cells for advoptive immunotherapy of melanoma," J. Immunother., 37(9):448-460,(2014).
Forget, Marie-Andree et al., A Novel Method to Generate and Expand Clinical-Grade Genetically Modified, Tumor-Infiltrating Lymphocytes, Frontiers in Immunology, 8(908):1-8, (2017).
Forget, Marie-Andree et al., "Prospective Analysis of Adoptive TIL Therapy in Patients with Matastatic Melanoma: Response, Impact of Anti-CTLA4, and Biomarkers to Predict Clinical Outcome," Clin Cancer Res, 24:4416-4428, (2018).
Forget, Marie-Andree et al.,"TIL therapy and- CTLA4: can they co-exist?," Oncotarget, 10:1-2, (2019).
Fox, Norma E. et al., "F104S c-MpI responds to a transmembrane domain-binding thrombopoietin receptor angonist: Proof of concept that selected receptor mutations in congenital amegakaryocytic thrombocytopenia can be stimulated with alternative thromboppietic agents," Exp Hematol., 38(5):384-391, (2010).
Frank, Ian et al., "Remarkably stable tumor-infiltrating lymphocyres (TIL) for infusion phenotype following cryopreservation," poster #11, Lion Biotechnologies, Society for Immunotherapy of Cancer, National Harbor, Maryland, MD, 1 pg., (Nov. 9-13, 2016).
Friedman, K.M., et al., "Augmented lymphocyte expansion from solid tumors with engineered cells for costimulatory enhancement," J. Immunother., 34(9):651-661, (2011).
Friedman, K.M., et al., "Tumor-specific CD4+ melanoma tumor-infiltrating lymphocytes." J. Immunother., 35(5):400-408, (2012).
Fujii, Hodaka et al., "Functional dissection of the cytoplasmic subregions of the IL-2 receptor βc chain in primary lymphocyte populations," The EMBO Journal, 17:6551-6557, (1998).
Ganesan, Anusha-Preethi et al., "Tissue-resident memory features are linked to the magnitude of cytotoxic T cell responses in human lung cancer," Nature Immunology, 18:940-950, (2017).
Gastman et al., "544: DELTA-1: A globle, multicenter phase 2 study of ITIL-168,an unrestricted autologous tumor-infiltrating lymphocyte (TIL) cell therapy, in adult patients with advanced cutaneous melanoma," J. Immunother. Canc. 9(Supplement 2): A573, (Nov. 1, 2021). [Retrieved from the Internet Nov. 1, 2021 <URL https://jitc.bmj.com/content/jitc/9/Suppl_2/A573.full.pdf>].
Gattinoni, Luca etal., "Adoptive immunotherapy for cancer: building on success," Nature Reviews Immonology, 6:383-393, (2006).
Gaurney, Austin L.et al.,"Distinct regions of c Mpl cytoplasmic domain are coupled to the JAK-STAT signal transduction pathway and Shc phosphorylation ," PNAS, 92:5292-5296,(1995).
Gee, Marvin H. etal., "Antigen Identification for Orphan T cell Receptors Expressed on Tumor-Infiltrating Lymphocytes," Cell, 172:1-15, (2018).
Gerber, Ken, "Pursuit of tumor-infiltrating lymphocyte immunotherapy speeds up," Nat Biotechnol., 37(9):969-971, (Sep. 2019).
Gettinger, S. et al., "Phase II, multicenter study of autologous tumor infiltrating lymphocytes (TIL, LN-144/LN-145/LN-145-S1) in patients with solid tumours," Journal of Thoracic Oncology, 16(4S):S799-800, (2021).
Gettinger, S.N.et al., "A dormant TIL phenotype defines non-small cell lung carcinomas sensitive to immune checkpoint blockers," Nature Communications, 9(3196):1-15,(2018).
Ghasmi, Reza et al., "Selective targeting of IL-2 to NKG2D bearing cells for improved immunotherapy," Nature Communications, 7(1):1-15, (2016).

Giraldo et al., "Tumor-infiltrating and Peripheral Blood T-cell Immunophenotypes Predict Early Relapse in Localized Clead Cell Renal Cell Carcinoma," Clin. Camcer Res., 23(15):4416-4428, (Feb. 17, 2017).
Goedegebuure, P.S., et al., "Adoptive immunotherapy with tumor-infiltrating lymphocytes and interleukin-2 in patients with metastatic malignant melanoma and renal cell carcinoma: a pilot study." J. Clic. Oncol., 13(8): 1939-1949, ABSTRACT (1995).
Goff, S.L., "Tumor Infiltrating lymphocyte therapy for metastatic melanoma: analysis of tumors resected for TIL," J. Immunother., 33(8):840-847, (2010).
Goff, S.L., et al., "Randomized, Prospective Evaluation Comparing Intensity of Lymphodepletion Before Adoptive Tranfer of Tumor-infiltrating Lymphocytes for Patients With Matastatic Melanoma," J. Clin. Oncol., 34(20):2389-2397, (2016).
Gokuldass, Aishwarya et al., "Redirected lysis assay as an efficient potency assay to assess TILs for immunotherapy," poster #14, Lion Biotechnologies, Society for Immunotherapy of Cancer, National Harbor, Maryland, MD, 1 pg., (Nov. 9-13, 2016).
Gontcharova, V. et al., "Persistence of cryopreserved tumor-infiltrating lymphocyte product lifileucel (LN-144) in C-144-01 study of advanced melanoma," AACR Annual Meeting, Lb-069/14, Abstract, (Mar. 29-Apr. 3, 2019).
Gordienko, I.M. et al., "Differential expression of CD150/SLAMF1 in normal and malignant B cells on the defferent stages of maturation," Exp. Oncol., 101-107, (2016).
Granhoj, J.S., et al., "Tumor-infiltrating lymphocytes for adoptive cell therapy: recent advance, challenges, and futere directions," Expert Opin.Biol. Ther., 22(5):627-641, (2022).
Grimm, E.A., et al., "Characterization of interleukin-2-initiated versus OKT3-initiated human tumor-infiltrating lymphocytes from glioblastoma multiforme: growth characteristics, cytolytic activity, and cell phenotype," Cancer Immunol. Immunother., 32(6):391-399, ABSTRACT (1991).
Grimm, Elizabeth A. etal., "Lymphokine-Activated Killer (LAK) Cell phenomenon," J exp. Med., 155:1823-1841, (Jun. 1982).
Gros Alena et al "Recognition of Human Gastrointestinal Cancer Neoantigens by Circulating PD-1 Lymphocytes ," J Clin Invest 129(11):4992-5004,(2019).
Gros, Alena et al.,"PD-1 identifies the patient specific CD8+tumor reactivce repertoire infiltratin human tumors ," J Clin , Invest ,124(5):2246-2259 (2014).
Guo, Xinyi et al., "Global characterisation of T cells in non-small-lung cancer by single cell sequencing ," Nature Medicine, 24:978-985, (2018).
Halbert Brian et al., "Successful Generation of Tumour Infiltrating Lymphocite (TIL)Product From Renal Cell Carcinoma Tumors For Adaptive Cell Therapy ," 176 SITC, Washington DC & Virtual, (Nov. 10-14, 2021).
Hall,M., "Expansion of tumor-infiltrating lymphocytes (TIL) from human pancreatic tumors," J Immunother, Cancer 4:61, (2016).
Hamalainen , Heli et al., "Signaling lymphocytic activation molecule (SLAM) is differntially expressed In human Th1 and Th2 cells ," Journal of Immunological Methods, 242:9-19, (2000).
Hamanishi, Junzo et al., "Programmed cell death 1 ligand 1 and tumor-infiltrating CD8+ T lymphocytes are prognostic factors of human ovarian cancer," PNAS, 104:3360-3365,(Feb. 27, 2007).
Harjes ,Urlike , "States of exhaustion," Nature Reviews Cancer, 19;185, (2019).
Hatzis ,Christos et al.,"Effects of Tissue Handeling on RNA Integrity and Microarray Measurments from Resected Breast Cancer ," J Natl .Cancer Inst., 103:1871-1883, (Dec. 21, 2011).
Hawkins Robert et al., "Treatment patterns and health outcomes in metastatic renal cell carcinoma pateints treated with targeted systemic therapies in the UK," BMC Cancer 20:670, (2020).
Hayakawa,M.,et al "[Study on adoptive immunotherapy with tumor-infratating lymphocytes (TIL) for renal cell carcinoma] Japanese ," Nihon Hinyokika Gakkai Zashi ,81 (1) ; 103-109, (1990).
He,J.,et al,"Ex vivo expansion of tumor-infiltrating lymphocytes from nasopharynangeal carcinoma patients for addoptive immunotherapy," Chin,J .Cancer ,31(6);287-294, (2012).

(56) References Cited

OTHER PUBLICATIONS

Heemskerk, Bianca et al., "Adoptive Cell Therapy for Pateints for Melanoma ,Using Tumor Infiltrating Lymphocytes Genetically Engennerd to Secret Interleukin-2," Human Gene Therapy ;10:496-510, (May 2008).
Henning,Gold ,et al., "Signaling lymphocytic activation molecule (SLAM) regulates T cellular cytotoxicity ," Eur ,J. Immunol. 31:2741-2750, (2001).
Hildreath,C,."CAR-T Companies Proliferate ;List of CAR-T Companies Worldwide," Bioinformant, (Aug. 30, 2021). [Retrived from the Internet Nov. 19, 2021; URL: <https;//bioinformant.com/car-t-copmpanies-the-meteoric-rise-of-cellular-immunotherapies/>].
Hinrichs ,Christian S. et al., "Exploiting the curative potential of adoptive T-cell therapy for cancer," Immunol Reviews, 257:56-71, (2014).
Hoch, Ute et al., "NKTR-214; An immunotherapy with altered selectivity at the IL2 receptor; pharmacokinetics (PK) and pharmacodynamics (PD) in animal models," Moleculer Cancer Therapeutics , 12(11), Abstract, (Nov. 2013).
Hong, J.J., et al., "Successful treatment of melanoma brain metastases with adoptive cell therapy," Clin. Cancer Res., 16(19):4892-4898, (2010).
Hopewell, E.L., et al., "Tumor-infilatring lymphocytes: Streamlining a complex manufacturing process," Cytotherapy, 21(3):307-314, (2019).
Howie , Duncan et al., "The role of SAP in murine CD150(SLAM)-mediated T-cell proliferation and interferon y production," Blood, 100:2899-2907, (2002).
Huang, Chih-Yang et al., "Cytosolic high-mobility group box protein 1 (HMGB1) and/or PD-1+ TILS in the tumor microenvironment may be contributing prognostic biomarkers for patients with locally advanced rectal cancer who have undergone neoadjuvant chemoradiotherapy," Cancer immunology, Immunotherapy, 67:551-562, (2018).
Minutoto, Nicholas G. et al., "The Emergence of Universal Immune Receptor T Cell Therapy for Cancer," Frontiers in Oncology, 9:176, (2019).
Morgan, R.A., et al., "Adoptive cell therapy: genetic modification to redirect effector cell specificity," Cancer J., 16(4):336-341, (2010).
Morgan, Richard A. et al., "Cancer Regression in Patients After Transfer of Genetically Engineered Lymphocytes," Science, 314:126-129, (2006).
Naito, Yoshitaka et al., "CD8+ T cells infiltrated within cancer cell nests as a prognostic factor in human colorectal cancer," Cancer Research 58:3491-3494, (Aug. 15, 1998).
Natarajan, Arvind et al., "Preclinical Activity and Manufacturing Feasibility of Genetically Modified PDCD-1 Knockout (KO) tumor-Infiltrating Lyphocyte (TIL) cell Therapy," 1015 AACR Annual Meeting, New Orleans, LA, (Apr. 8-13, 2022).
Nektar, "Nektar Therapeutics Announces Publication of Two Manuscripts on lead Immuno-oncology candidate, Bempagaldesleukin (Bempeg) in Nature Communications," 2 pgs., San Francisco, CA, (Feb. 3, 2020).
Nektar, "Preclinical Data Presented at ASCO 2016 Annual Meeting Demonstrate that Single-Agent NKTR-214 Produces a Larga Increase in Tumor-Infiltrating Lymphocytes to Provide Durable Anti-Tumor Activity," 2 pgs., San Francisco, CA, (Jun. 6, 2016).
Nelson, Brad H., "CD20+ B Cells: The Other Tumor-Infiltrating Lymphocytes," JIM, 185(9):4977-82, (Nov. 2010).
Nguyen et al., "Expansion and Characterization of Human Melanoma Tumor-Infiltrating Lymphocytes (TILs)," Plos One 5(11):e13940, (Nov. 10, 2010).
Nishimura, Christopher D. et al., "c-MPL provides tumor-targeted T-cell receptor-transgenic T cells with Costimulation and cytokine signals," Blood, 130:2739-2749, (2017).
Non-Final Rejection dated Sep. 12, 2022 for U.S. Appl. No. 17/826,053.
O'Malley, David et al., "Phase 2 Efficacy and Safety of Autologous Tumor-Infiltrating Lymphocyte (TIL) Cell Therapy in Combination with Pembrolizumab in Immune Checkpoint Inhibitor-Naïve Patients with Advance Cancers," 36th Annual Meeting & Pre-Conference Programs SITC, Washington, DC, (Nov. 1014, 2021).
Oberst, Andrew et al., "Catalytic activity of the caspase-8-FLIPL complex inhibits RIPK3-dependent necrosis," Nature, 471:363-367, (2011).
Onmimus, Kenneth et al., "Expansion of Tumor-Infiltrating Lymphocytes (TIL) Using Static Bag for the Clinical Manufacturing Rapid Expansion Protocol (REP) Process," 101 SITC, Washington, DC & Virtual, (Nov. 10-14, 2021).
Oppermans, Natasha et al., "Transgenic T-cell receptor immunotherapy for cancer building on clinical success," Therapeutic Advances in Vaccines and Immunotherapy, 8:1-17, (2020).
Orrego, Enrique et al., "Distribution of tumor-infiltrating immune cell in glioblastoma," CNS Oncol., 7(4): CNS21, (Dec. 2018).
Otto, Grant, "A human antibody selectively targets regulatory T cells," Nature Reviews Drug Discovery, 17:546, (2018).
Paijens, Sterre T. et al., "Tumor-infiltrating lymphocytes in the immunotherapy era," Cellular & Molecular Immunology, 18:842-859, (2021).
Panchal, Neelam et al., "Transfer of gene-corrected T cells corrects humoral and cytotoxic defects in patients with X-linked lymphoproliferative disease," J Allergy Clin Immunol, 142:P235-245, (2018).
Parakurst, M.R., et al., "T cells targeting carcinoembryonic antigen can mediate regression of metastatic colorecta cancer but induce severe transient colitis," Mol. Ther., 19(3):620-626, (2011).
Parisi, Giulia et al., "Persistence of adoptively transferred T cells with a kinetically engineered IL-2 receptor agoinst," Nature Communications, 11(660):1-12, (2020).
Pathak et al., "Eltrombopag for the treatment of thrombocytopenia in patients with malignant and non-malignant hematologic disorders," Expert Opin. Drug Metab. Toxicol, 9(12):1667-1675, (2013).
Pauken, Kristen E. et al., "Epigenetic stability of exhausted T cells limits durability of reinvigoration by PD-1 blockade," Science, 354:1160-1165, (2016).
Pililla-Ibarz, Javier et al., "Trial in Progress: Phase 1/2 Study Evaluating the Safety and Efficacy of Iov-2001, an Autologous, Non-Genetically Modified, Polyclonal T-Cell Product, in Patients with Relapsed or Refractory Chronic Lymphocytic Leukemia (CLL) or Small Lymphocytic Lymphoma (SLL) (IOV-CLL-01)," 2846 ASH 2021, Atlant, GA & Virtual, (Dec. 11-14, 2021).
Pillai, M. et al., "Tumour Infiltrating Lymphocyte Therapy: Clinical Outcomes in Pre-treated Metastatic Melanoma Patients and Biomarker Correlation," Immetacyte, Ltd., 1 pg., (2018).
Pilon-Thomos, Shari, "Adoptive Cell Therapy Using Tumor Infiltrating Lymphocytes (TIL) and Application to Bladder Cancer," 30 pags., (2017).
Plo et al., "Genetic Alterations of the Thrombopoietin/MPL/JAK2 Axis Impacting Megakaryopoiesis," Front Endocrinol (Lausanne), 8:234, (Sep. 12, 2017).
Poschke et al., "The Outcome of Ex Vivo TIL Expansion Is Highly Influenced by Spatial Heterogeneity of the Tumor T-Cell Repertoire and Differences in Intrinsic In Vitro Growth Capacity between T-Cell Clones," Clin. Cancer Res., 26(16):4289-4301 (Apr. 17, 2020).
Powell, Daniel J., Jr. et al., "Translating fundamental immunobiology into adoptive T-cell therapy for ovarian cancer," Clin Cancer Res., 24:IA24, Suppl. 15, (2018).
Price-Troska, Tammy et al., "Inhibiting IL-2 signaling and the regulatory T-cell pahtway using computationally designed peptides," Invest New Drugs, 37:9-16, (2018).
Prieto, P. A., et al., "Enrichment of CD8+ Cells From Melanoma Tumor-infiltrating Lymphocyte Cultures Reveals Tumor Reactivity for Use in Adoptive Cell Therapy," J. Immunother., 33(5):547-556, (2010).
Quiroga, Maria F. et al., "Activation of signaling lymphocytic activation molecule triggers a signaling cascade that enhances Th1 responses in human intracellular infection," The Jorunal of Immunology, 173:4120-4129 (2004).
Ren, Lili et al., "similarity and difference in tumor-inflitrating lymphocytes in orininal tumor tissue and those of vitro expanded population in head and neck cancer," Oncotarget, 9:3805-3814, (2018).

(56) References Cited

OTHER PUBLICATIONS

Requirement for Restriction/Election dated May 18, 2022 for U.S. Appl. No. 16/477,366.
Restifo, N.P., et al., "Adoptive immunotherapy for cancer: harnessing the T cell response," Nat. Rev. Immunol., 12(4):269-281, (2012).
Ribba, Benjamin et al., "Prediction of the Optimal Dosing Regimen Using a Mathematical Model of Tumor Uptake for Immunocytokine-Based Cancer Immunotherapy," Clin Cancer Res, 24:3325-3333, (2018).
Ring, Aaron M. et al., "Mechanistic and structural insight into the function dichotomy between IL-2 and IL-15," Nature Immunol., 13(12):1187-195, (Dec. 2012).
Ripley, R.T., et al., "Liver resection for metastatic melanoma with postoperative tumor-infiltrating lymphocyte therapy," Ann. Surg. Oncol., 17(1):163-170, (2010).
Ritthipichai, Krit, "Activating OX40 receptor promotes the expansion of CD8+ TIL with enhanced T-cell effector function," LB-110 AACR Annual Meeting, Chicago, IL, (Apr. 14-18, 2018).
Ritthipichai, Krit, "Genetic modification of lovance's TIL through TALEN-mediated knockout of PD-1 as a strategy to empower TIL therapy for cancer," AACR Annual Meeting, 1052P, Abstract, (2020).
Ritthipichai, Krit, "K+ Channel Activation Promotes Tumor Infiltrating Lymphocyte (TIL) Expansion and Enhances Expression of CCR7," 66 AAI Annual Meeting, Washington, DC, (May 12-16, 2017).
Ritthipichai, Krit, "Studies of Key Quality Attributes for TIL Product, LN-144," P194 SITC Annual Meeting, National Harbor, MD, (Nov. 8-12, 2017).
Robbins, P.F., et al., "Cutting edge: persistence of transferred lymphocyte clonotypes correlates with cancer regression in patients receiving cell transfer therapy," J. Immunol., 173(12):7125-7130, (2004).
Robbins, Paul F. et al., "Mining exomic sequencing data to identify mutated antigens recognized by adoptively transferred tumor-reactive T cells," Nature Medicine, 19(6):747-752, (2013).
Robertson, Jane et al., "Tumour Infiltrating Lymphocyte-Adoptive Cell Therapy:the emerging importance of clonal neoantigen targets for next-generation products in Non-Small Cell Lung Cancer," IOTECH, 3:7, (2019).
Rohan, Maartje W. et al., "Adoptive transfer of tumor-infiltrating lyphocytes in melanoma: a viable treatment option," Jounal of Immuno Therapy of Cancer, 6(1):102, (2018).
Romangoli, Gloria et al., "Morphological Evaluation of Tumor-Infiltrating Lymphocytes (TILs) to Investigate Invasive Breast Cancer Immunogenicity, Reveal Lymphocytic Networks and Help Relapse Prediction: A Restrospective Study," Int. J. Mol. Sci., 18(9):1936, (2017).
Rosenberg et al., Durable complete responses in heavily prelreated patients with metastalic melanoma using t-cell transfer immunotherapy. Clin. Cancer Res, 17(13):4550-7.
Rosenberg, S. A., et al., "Cancer regrssion in patients with metastatic melanoma after the transfer of autologous antitumor lymphocytes," Proc. Natl. Acad. Sci. U.S.A., 101 Suppl 2(Suppl 2):14639-14645, (2004).
Rosenberg, S. A., et al., "Cell transfer therapy for cancer: lessons form sequential treatments of a patient with metastatic melanoma," J. Immunother., 26(5):385-393, (2003).
Aabas, Abul K, et al., "Revisiting IL-2 Biolog and therepautic prospects," Science Immunology, 3(25): eaat1482, (2018).
Ahmadzadeh, Mojgan et al., Tumor-infiltrating human CD4+ regulatory T cells display a distinct TCR repertoire and exhibit tumor and neoantigen reactivity, Science Immunology 4(31): eaao4310, (2019).
Albu, Roxana I. et al., "Extracellular domain N-glycosylation controls human thrombopoietin receptor cell surface levels," Frontiers in Endocrinology, 2:71, (Nov. 2011).

Aldhamen, YA et al., "Improved cytotoxic T-lymphocyte immune responces to a tumor antigen by vaccines co-expressing the SLAM-associated adaptor EAT-2," Cancer Gene Therapy, 20:564-575, (2013).
Alfaguter, Inbar Azoulay et al., "Silencing PD-1 using PH-762 (PD-1 targeting INTASYL compound) to improve lovance TIL effector function using Gen 2 manufacturing method," P149 SITC Annual Meeting, National Harbor, MD, (Nov. 6-10, 2019).
Almeida, Afonso R.M. et al., "Homeostasis of Peripheral CD4+ T Cells: IL-2R a and IL-2 Shape a Population of Regulartory Cells That Controls CD4+ T Cells," J Immunol, 169:4850-4860, (2002).
Alva, Ajjai et al., "Contemporary experience with high-dose interleukin-2 therapy and impact on survival in patients with metastatic melanoma and metastatic renal cell carcinoma," Cancer Immunol Immunother., 65:1533-1544, (2016).
Alvarez-Vallina, Luis et al., "Antigen-specific targeting of CD28-mediated T cell co-stimulation using chimeric single-chain antibody variable fragment-CD28 receptors," Eur. J. Immunol., 26:2304-2309, (1996).
Amaria, Rodabe Navroze et al., "Adoptive transfer of tumor-infiltrating lymphocytes in patients with sarcomas, ovarian and pancreatic cancers," J Clin Oncol., 37:Suppl., Abstract TPS2650, (2019).
Andersen et al., "T cells isolated from patients with checkpoint inhibitor-resistant melanoma are functional and can mediate tumor regression," Ann. Oncol. 29(7): 1575-1581, (Jul. 1, 2018).
Andrews, Sarah F. et al., "T-bet+ memory B cells stay in place," Immunity, 52:724-726, (2020).
Antohe, Michael et al., "Tumor infiltrating lymphocytes: The regulator of melanoma evolution (Review)," Oncol Lett., 17:4155-4161, (2019).
Armstong, M.,"Iovance delayed again," BioInformant, (May 19, 2021). [Retrieved from the internet: May 19, 2021 URL: <https//www.evaluate.com/node/16891/pdf>].
Atkins, Michael B. et al., "High-Dose Recombinant interleukin 2 Therapy for Patients with Metastatic Melanoma: Analysis of 270 Patients Treated Between 1985 and 1993," Journal of Clinical Oncology, 17:(7):2105-2116, (Jul. 1999).
Aversa, G. et al., "Engagement of the signaling lymphocytic activation molecule (SLAM) on activated T cells results in IL-2-independnet, cyclosporin A-sensitive T cell proliferation and IFN-gamma production," J Immunol., 158-4036-4044, (1997).
Bajgain, P., et al., "Optimizing the production of suspension cells using the G-Rex "M" series," Mol. Ther. Methods Clin. Dev., 1:14015, (2014).
Baldan, V. et al., "Efficient and reproducible generation of tumour-infiltrating lymphocytes for renal cell carcinoma," BJC, 112:1510-1518, (2015).
Bast, Robert C., Jr. et al., "Critical questions in ovarian cancer research and treatment: Report of an American Association for Cancer Research Special Research," Cancer, 125:1963-1972, (2019).
Bedognetti, D. et al., "CXCR3/CCR5 Pathways in Metastatic Melanoma Pateints Treated with Adoptive Therapy and Interleukin-2," BJC, 109:2414-2423, (2013).
Beltra, Jean-Christophe et al., "Developmental Relationships of Four Exhausted CD8+ T Cell Subsets Reveals Underlying Transcriptional and Epigentic Landscape Control Mechanisms," Immunity, 52:825-841, (May 2020).
Besser, M.J., et al., "Adoptive transfer of tumor-infiltrating lymphocytes in patients with metastatic melanoma: intent-to-treat analysis and efficacy after failure to prior immunotherapies," Clin. Cancer Res., 19(17):4792-4800, (2013).
Besser, M.J., et al., "Clinical responses in a phase II study using adoptive transfer of short-term cultured tumor infiltration lymphocytes in metastatic melanoma patients," Clin. Cancer Res., 16(9):2646-2655, (2010).
Bhatia, Alka et al., "Tumour Infiltrating Lymphocytes: Changing Trends," Clinics in Oncology, 3:1409, (2018).
Bierer et al ("The Biologic Roles of CD2, CD4, and CDS Int-Cell Activation," Ann. Rev. Immunol. 1989. 7:579-99) (Year: 1989).
Blank, Christian U. et al.,"Defining T cell exhaustion'," Nature Reviews Immunology, 19:665-674, (2019).

(56) References Cited

OTHER PUBLICATIONS

Boldajipour, Bjan et al., "Tumor-inflitrating lymphocytes are dynamically desensitized to antigen but are maintained by homeostatic cytokine," JCI insight., 1(20):e89289, (2016).
Bologna et al., "Disclosures: Slamf-1/CD150 is a Signaling Receptor Expressed by a Subset of Chronic Lymphocytic Leaukemia Patients Characterized by a Favorable Prognosis," Blood, 120(21):1770, (Nov. 16, 2012).
Bonanno,L, et al., The role of immune microenvironment in small-cellling cancer: Distribution of PD-L1 expression and prognostic role of FOXP3-positive tumour infiltrating lymphocytes: European Journal of Cancer, 101:191-200 (2018).
Borsa, Mariana et al., "Modulation of asymmetric cell division as a mechanism to boost CD8+ T cell memory," Sci. Immunol. 4(34):1-15, (Apr. 12, 2019).
Boussiotis, Vassiliki A. et al., "Prevention of T cell Anergy by Singnaling Through the yc Chain of the IL-2 Receptor," Science,266:1039-1042, (Nov. 11, 1994).
Bowtelll, David D. et al., "Rethinking ovarian cancer II: reducing mortality from high-grade serous ovarian cancer," Nat. Rev. Cancer, 15:688-679,(2015).
Bridgeman et al., "Building better chimeric antigen receptors for adoptive T cell therapy," Curr. Gene Ther., 10(2):77-90, (2010).
Bridgeman et al., Instil Bio Website, "In vitro analysis of tumor infiltrating lymophocytes ," (Nov. 1, 2018).[Retrieved from Internet May 3, 2022; <URL: https://instilbio.com/wp-content/uploads/2021/01/2018-SITC-Poster-in-vitro-analysis-of-Tumour-Infiltrating-Lymphocytes-engineered-with-contimulatory.pdf>].
Bridgeman et al., "CD3?-based chimeric antigen receptors mediate T cell activation via cis-and trans-signaling mechanisms: implications for optimization of receptor structure for adoptive cell therapy," Clin. Exp. Immunol., 175(2):258-267, (2014).
Bridgeman, John S. et al.,"Genetic Engineering of Tumour Infiltrating Lymphocytes (TIL) with a Novel Recombinant Growth Factor Receptor for Treatment of Solid Tumours," Immetacyte, Ltd., 1 pg., (2018).
Bridgeman, John S. et al., "ln vitro analysis of Tumour Infiltrating Lymphocytes engineered with costimulatory anigen receptors delivering targeted costimulation," Immetacyte,Ltd., 1 pg., (2018).
Bright, Richard et al. "Clinical Response Rates from Interlrukin-2 Therapy for metastatic Melanoma Over 30 Years' Experience: A Meta-Analysis of 3312 Patients," J Immunother, 40(1):21-30, (Jan. 2017).
Browning et al., "The T cell activation marker CD150 can be used to identify alloantigen-activated CD4(+)25+ regulatory T cells," Cell. Immunol.,227(2)4 29-139, (2004).
Buchbinder, Elizabeth I. et al., "A restrospective analysis of High-Dose Interleukin (HD IL-2) following IL-2 Ipilimumab in metastatic melanoma," Journal for Immuno Therapy of Cancer, 7:52, (2016).
Buchbinder, Elizabeth I. et al., "Therapy with high-dose Interleukin-2 (HD IL-2) in metastatic melanoma nd renal cell carcinoma following PD1 and PDL1 inhibition," Jounral for ImmunoTherapy of Cancer, 7:49, (2019).
Byrne, Ann et al., "Tissue-resident memory T cells in breast cancer control and immunotherapy responses," Nature Reviews Clinical Oncology, 17:341-348, (2020).
Cafri, Gel et al., "Memory T cells targeting oncogenic mutations detected in peripheral blood of epithelial cancer patients," Nature communications, 10:449, (2019).
Camp, F.A., et al., "Implications of Antigen Selection on T Cell-Bassed Immunotherapy," Pharmaceuticals (Basel), 14(10);993, (2021).
Canale, Fernando P. et al., "CD39 Expression Defines Cell Exhaustion in Tumor-Infiltrating CD8+ T cells," Cancer Research, 78(1):115-128, (2018).
Caushi, Justina X. et al., "Transcriptional programs of neoantigen-specific TIL in anti PD-1-treated lung cancer," Nature, 596:126-132, (2021).
Cervera-Carrascon, V. et al., "TNFa and IL-2 armed adenoviruses enable complete responses by anti-PD-1 checkpoint blockade," Oncoimmunology, 7(5):1-11, (2018).
Chacon, Jessica Ann et al., "Manupulating the Tumor Microenvironment Ex Vivo for Enhanced Expansion of Tumor-Infiltrating Lymphocytes for Adoptive Cell Therapy," Clin Cancer Reseach, 21(3):611-621, (Feb. 2015).
Challier, Cecile et al., "The cytoplasmic domain of Mpl receptor transduces exclusive signals in embryonic and fetal hematopoietic cells," Blood, 100:2063-2070, (2002).
Charych, Deborah et al., "NKTR-214, an Engineered Cytokine with Biased IL2 Receptor Binding Increased Tumor Exposure, and Marked Efficacy in Mouse Tumor Models," Clin. Cancer Res., 22(3):680-290, (Feb. 1, 2016).
Charych, Deborah et al., "Tipping the balance in the tumor microenvironment: An engineered cytokine (NKTR_214) with altered IL2 receptor binding selectivity and improved efficacy," Cancer Research, 73(8), Abstract, (Apr. 2013).
Rosenberg, S. A., et al., Treatment of patients with metastatic melanoma with autologous tumor-infiltrating lymphocytes and interleukin 2, J. Natl. Cancer Inst., 86(15):1159-1166, (1994).
Rosenberg, S.A., et al., "A new approach to the adoptive immunotherapy of cancer with tumor-infiltrating lymphocytes," Science, 233(4770):1318-1321, (1986).
Rosenberg, S.A., et al., "Adoptive cell therapy for the treatment of patients with metastatic melanoma," Curr. Opin. Immunol., 21(2):233-240, (2009).
Rosenberg, S.A., et al., "Cancer immunotherapy," N. Engl. J. Med., 359(10):1072, (2008).
Rosenberg, Steven A. et al., "Abstract IA14: Cell transfer immunotherapy trageting unique somatic mutations in cancer," Cancer Immunol Res 7(2):IA14, Supplement, (2019).
Rosenberg, Steven A. et al., "Adoptive cell transfer as personalized immunotherapy for human cancer," Science, 348:62-68, (2015).
Rosenberg, Steven A. et al., "Adoptive cell transfer: a clinical path to effective cancer immunotherapy," Cancer, 8:299-308, (Apr. 2008).
Rosenberg, Steven A. et al., "Durable complete responses in heavily pretreated patients with metastatic melanoma using T-cell transfer immunotherapy," Clinl Cancer Res, 17(13):4550-4557, (2011).
Rosenberg, Steven A. et al., "Finding suitable targets is the major obstacle to cancer gene therapy," Cancer Gene Therapy, 21:45-47, (2014).
Rosenberg, Steven A. et al., "Gene transfer into humans: immunotherapy of patients with advanced melanoma, using tumor-infiltrating lymphocytes modified by retroviral gene transduction," N. Engl. J. Med. 323(9):570-578, (Aug. 30, 1990).
Rosenberg, Steven A. et al., "Use of tumor-infiltrating lymphocytes and interieukin-2 in the immunotherapy of patients with metastatic melanoma," NEJM, 319:1676-1680, (Dec. 22, 1988).
Royer, Yohan et al., "Janus Kinases Affect Thrombopoietin Receptor Cell Surface Localization and Stability," The Journal of Biological Chemistry, 280:27251-27261, (2005).
Sadelain, Michel et al., "Therapeutic T cell engineering," Nature 545:423-431, (2017).
Saka, Koichiro et al., "Top-down motif engineering of a cytokine receptor directing ex vivo expansion of hematopoietic stem cells," Journal of Biotechnology, 168:659-665, (1995).
Sakaguchi, Shimon et al., "Immunologic self-tolerance maintained by activated T cells expressing IL-2 receptor alpha-chains (CD25)," J Immunol., 155(3):1151-1164, (1995).
Sakellariou-Thompson, Donastas et al., 4-1BB Agonist Focuses CD8+ Tumor-Infiltrating T-Cell Growth into a Distinct Repertoire Capable of Tumor Recognition in Pancreatic Cancer, Clin Cancer Research, 23:7263-7275 (2017).
Sampson-Abelson, Michelle R et al., "Expanding lovance's tumor infiltrating lymphocytes (TIL) from core Biopsies for adoptive T cell therapy using a 22-day manufacturing process," p145 SITC Annual Meeting, National Harbor, MD, (Nov. 6-10, 2019).
Santoiemma, Phillip P. et al., "Systematic evaluation of multiple immune markers reveals prognostic factors in ovarian cancer," Gynecol. Oncol., 143:120-127, (2016).

(56) References Cited

OTHER PUBLICATIONS

Santoiemma, Phillip P. et al., Tumor infiltrating lymphocytes in ovarian cancer, Cancer Biology & Therapy, 16:807-820, (Jun. 2015).

Sarnaik, Amod A. et al., "Lifileucel, a Tumor-Infiltrating Lymphocyte Therapy, in Metastatic Melanoma," J. Clin. Oncol., 39:2656-2666, (2021).

Sarnaik, Amod et al., "A Phase 2, Multicenter Study to Assess the Efficacy and Safety of Autologous Tumor Infiltrating Lymphocytes (LN-144) for Treatment of Patients with Metastatic Melanoma," CT169 AACR Annual Meetin, Chicago, IL, (Apr. 14-18, 2018).

Sarnaik, Amod et al., "Efficacy of single administration of tumor-infiltrating lymphocytes (TIL) in heavily pretreated patients with metastatic melanoma following checkpoint therapy," Lion Biotechnologies, 140 ASCO Annual Meeting, Chicago, IL (Jun. 2-6, 2017).

Sarnaik, Amod et al., "Long-term follow up of lifileucel (LN-144) cryopreserved autologous tumor infiltrating lymphocyte therapy in patients with advanced melanoma progressed on multiple prior therapies," ASCO Annual Meeting, Tampa FL, (2020).

Sarnaik, Amod et al., "Novel Crypreserved Tumor Infiltrating Lymphocytes (LN 144) Administered to Patients with Metastatic Melanoma Demonstrates Efficacy and Tolerability in a Multicenter Phase 2 Clinical Trail," P515 SITC Annual Meeting, National Harbor, MD, (Nov. 8-12, 2017).

Sarnaik, Amod et al., "Safety and efficacy of cryopreserved autologous tumor infiltrating lymphocyte therapy (LN-144, lifileucel) in advaced metastatic melanoma patients following progression on checkpoint inhibitors," 022 SITC Annual Meeting, Washington, DC, (Nov. 7-11, 2018).

Sarnaik, Amod et al., "Safety and efficacy of cryopreserved autologous tumor infiltrating lymphocyte therapy (LN-144, lifileucel) in advaced metastatic melanoma patients who progressed on multiple prior therapies including anti-PD-1," 162 ASCO Annual Meeting, Chicago, IL, (May 31-Jun. 4, 2019).

Sarnaik, Amod et al., "Safety and efficacy of cryopreserved autologous tumor infiltrating lymphocyte therapy (LN-144, lifileucel) in advaced metastatic melanoma patients who progressed on multiple prior therapies including anti-PD-1," J Clin Oncol., 37:Suppl., Abstract 2518, (2019).

Sarnaik, Amod et al., "Safety and efficacy of lifileucel (LN-144) tumor infiltrating lymphocyte therapy in metastatic melanoma patients after progression on multiple therapies—independent review committee data update," P865 SITC Annual Meeting, National Harbor, MD, (Nov. 6-10, 2019).

Sato, Eiichi et al., "Intraepithelial CD8+ tumor-infiltrating lymphocytes and a high CD8+/regulatory T cell ration are associated with favorable prognosis in ovarian cancer," PNAS 102:18538-18543, (Dec. 20, 2005).

Satpathy, Ansuman T. et al., "Massively parallel single-cell chormatin landscapes of human immune cell development and intratumoral T cell exhaustion," Nature Biotechnology, 37:925-936, (Aug. 2019).

Scheper, Wouter et al., "Low and variable tumor reactivity of the intratumoral TCR repertorie in human cancer," Nature Medicine, 25:89-94, (2018).

Schoenfeld, Adam J. et al., "First phase 2 results of autologous tumor-infiltrating lymphocyte (LN-145) monotherapy in patients with advanced, immune checkpoint inhibitor-treated, non-small cell lung cancer (NSCLC)," 458 SITC, Washington DC & Virtual, (Nov. 10-14, 2021).

Schwartzberg, Pamela L. et al., "SLAM receptors and SAP influence lymphocyte interaction, development and function," Nat Rev Immunol., 9(1):39-46, (2009).

Seitter, Samantha J. et al., "Impact of Prior Treatment on the Efficacy of Adoptive Transfer of Tumor-Infiltrating Lymphocytes in Patients with Metastatic Melanoma," 27(19):5289-5298, (2021).

Sen, Debattama R. et al., "The epigenetic landscape of T cell exhaustion," Science, 354:1165-1169, (2016).

Sethuraman, Jyothi et al., "Successful expansion and characterization of tumor infiltrating lymphocytes (TILs) from non-melanoma tumors," Poster #42, Lion Biotechnologies, Society for Immunotherapy of Cancer, National Harbor, Maryland, MD, 1 pg., (Nov. 9-13, 2016).

Sharifi, Reza et sl., "SAP mediates specific cytotoxic T-cell functions in X-linked lymphoproliferative disease," Blood, 103(10):3821-3827, (2004).

Shen, Xinglei et al., "Persistence of Tumor Infiltrating Lymphocytes in Adoptive Immunotherapy Correlates with Telomere Length," J. Immunother., 30:123-129, (2007).

Sidaway, Peter, "TIL infusions effective in HPV-associated cancers," Nature Reviews Clinical Oncology, 16:144, (2019).

Silva, Daniel-Adriano et al., "De novo design of potent and selective mimics of IL-2 and IL-15," Nature, 565:186-191, (2019).

Simpson-Abelson, Michelle R. et al., "Emigrant Tumor infiltrating Lymphocytes (TIL) Profound Differ from Remnant T-cells," 649 AACR Annual Meeting, Washington, DC, (Apr. 1-5, 2017).

Simpson-Abelson, Michelle R. et al., "Iovance generation-2 tumor-infiltrating lymphocytle (TIL) product is reinvigorated during the manufacturing process," 1053P ESMO virtual Congress, (Sep. 19-21, 2020).

Simpson-Abelson, Michelle R. et al., "PD1-positive tumor-infiltrating lymphocytes (TIL) for the next generation of adoptive T cell therapy," P210 SITC Annual Meeting, Washington,DC, (Nov. 7-11, 2018).

Simpson-Abelson, Michelle R. et al., "The T-cell Growth Factor Cocktail IL-2/IL-15/L-21Enhances Expances Expansion and Effector Function of tumor-Infiltration T cells in a Novel Process Developed by Iovance," P367 SITC Annual Meeting, National Harbor, MD, (Nov. 8-12, 2017).

Sims et al., "Diversity and divergence of the glioma-infiltrating R-cell receptor repertoire," Proc. Natl. Acad. Sci. U.S.A., 113(25):E3529-E3537, (2016).

Singer, Meromit et al., "A Distinct Gene Module for Dysfunction Uncoupled from Activation in Tumor-Infiltrating T Cells," Cell, 166:1500-1511, (2016).

Smith, Jenessa B. et al., "Tumor regression and delayed onset toxicity following B7-HR CAR T cell therapy," MOL. Ther., 24:1987-1999.(2016).

Smyrk, Thomas C. et al., "Tumor-Infiltrating Lymphocytes are a Marker for Microsatellite Instavility in Colorectal Carcinoma," 91(12):2417-2422, (Jun. 15, 2001).

Sockolosky, Jonathan T. et al., "Selective targetiing of engineered T cells using orthogonal IL-2 cytokine-receptor complexes," Science, 359:1037-1042.(2018).

Soerville, R.P., et al., "Clinical Scale rapid expansion of lymphocytes for adoptive cell transfer therapy in the WAVE® Bioreactor," j. Transl. Med., 10:69, (2012).

Sogo et al., "T cell growth control using hapten-specific antibody/interleuking-2 receptor chimera," Cytokine, 46(1):127-136, (2009).

Song, De-Gang Eet al., "in Vivo Persistence, Tumor Locaization, and antitumor activity CAR-Engineered T Cells is Enhanced by Contimulatory Signaling through CD137 (4-1BB)," Cancer Res., 71:4617-4627,(2011).

Spindler, Matthew J. et al., "Massively parallel interrogation and mining of natively paired human TCR?β repertoires," Nature Biotecnology, 38:609-619, (2020).

Spruessel, Annika et al., "Tissue ischeme time affects gene and protein expression patterns within minutes following surgical tumor excision," BioTechniques, 36(6): 1030-1037, (2004).

Stefan Mehrle, et al.. Enhancement of anti-tumor activity in vitro and in vivo by CD150 and SAP11, Molecular Immunology. (Feb. 1, 2008), vol. 45. No. 3, pp. 796-804.

Stevanovic, S., et al., "Complete regression of metastaticcervical after treatment with human papillomavirus-targeted tumor-infiltrating T Cells," J. Clin. Oncol., 33(14):1543-1550, (2015).

Subramanian, Krithika, "TILs Show Growing Potential as Novel Immunotherapy," OncologyLive, 19(19):1-12, (2018).

Sun, Hongliang et al., "Eltrombopag, a thrombopoietin receptor agonist, enhances human umbilical cord blood hematopoietic stem/primitive progenitor cell expansion and promotes multi-lineage hematopoiesis," Stem Cell Reseach, 9:77-86, (2012).

(56) References Cited

OTHER PUBLICATIONS

Sykorova, M. et al., "CostAr (Costimulatory Antigen Receptor) Enhancement of Tumour Infiltrating Lymphocyte Therapy," Instibio, 1 pg., (2019).
Synthorx, "Synthorx to Present Preclinical Data for THOR-707, a "Not-Alpha" IL-2 Synthorin, for the Treatment of Solid Tumors at SITC 2018," NEJM, 375:2255-2262, (2016).
Tang, Haidong et al., "Facilitating T Cell Infiltrating in Tumor Microenvironment Overcomes Resistance To PD-L1 Blockade," Cancer Cell, 29:285-296, (2016).
Tang, Li et al., "Enhancing T cell through TcR-signaling-responsive nanoparticle Drug Delivery," Nature Biotechnology, 36:707-716, (2018).
Tanyi, Janos L. et al,. "Personnalized cancer vaccine effectively mobilizes antitumor T Cell immunity in ovarian cancer," Sci. Transi. Med., 10:eaao5931, (2018).
Tong, Wei et al., "The Membrane-proximal Region of the Thrombopoietin Receptor Confers Its high Surface Expression by Jak2-dependent and—independent Mechanisms," Jpomal of Biological Chemistry, 281:38930-38940, (2006).
Topalian, S,L., et al., "Expansion of human tumor infiltrating lymphocytes for use in immunotherapy trials," J. Immunol. Methods, 102(1):127-141, (1987).
Tran, Eric et al., "Cancer Immunotherapy Based on Mutation-Specific CD4+ T Cells in a Patient with Epithelial Cancer," Science, 344:641-645, (May 2014).
Tran, Eric et al., "Final common pathway' of human cancer immunotherapy: targeting random somatic mutations," Nature Immunology, 18:255-262, (2017).
Tran, Eric et al., "T-Cell Transfer Therapy Targeting Mutant KRAS in Cancer," Science 344:641-645, (May 2014.).
Tran, K.Q., et al., "Minimally cultured tumor-infiltrating lymphocytes display optimal characteristics for adoptive cell therapy cell," J. immunother, 31(8):742-751, (2008).
Turcotte, S., et al., "Phenotype and function of T cells infiltrating visceral metastases from gastrointestinal cancers and melanoma: implications for adoptive cell transfer therapy," J Immunol., 191(5):2217-2225, (2013).
U.S. Securities and Exchange Commission, Form 8-K for Iovance Biotherapeutics, Inc., First Quarter Financial Results and Corporate Updates, dated May 6, 2021.
Usacheva, Anna et al., "Contribution of the Box 1 and Box 2 motifs of cytokine receptors to Jaki association and activation," The Journal of Biological Chemistry, 277:48220-48226, (2002).
Veatch, Joshua R. et al., "Tumor-infiltrating BRAFV600E-specific CD4+ T cells correlated with complete clinical response in melanoma," J Clin Invest., 128(4):1563-1568, (2018).
Veatch, Joshua R. et al., "Tumor-infiltrating lymphocytes make inroads in non-small-cell lung cancer," Nature Medicine, 27:1338-1344, (Aug. 2021).
Veerapathran Anand et al., "Artificial antigen presenting cells promote expansion of tumor-infiltrating lymhocytes (TILs)," Poster#47, Lion Biotechnologies, Socitey for Immunotheray of Cancer, National Harbor, Maryland, MD, 1 pg., (Nov. 9-13, 2016).
Veerapathran M., "Cryopreservation-Induced Enchancement of Interleukin-2 Production in Human Peripheral Blood Monuclear Cells," Cryobiology 29:165-174, (1992).
Veerapathran, M., "Effects of cryopreservation on immune responses: VII. Freezing induced enhancement of IL-6 production in human peripheral blood mononuclear cells," Cryobiology, 31:468-477, (1994).
Vodnala, Suman Kumar et al., "Identifying the source of tumour-infiltrating T cells," Natrue, 576:385-386, (2019).
Vodnala, Suman Kumar et al., "T cell sternness and dysfunction in tumors are triggered by a common mechanism," Science, 363(6434):eaau0135, (Mar. 2019).
Wang, L.L., et al., "Cell therapies in the clinic," Bioeng. Transl. Med., 6(2):e10214, (2021).
Wang, S., et al., "Perspectives of tumor-infiltrating lymphocyte treatment in solid tumors," BMC Med., 19(1):140, (2021).
Wang, Sheng-Yuan et al., "The Influence of Cryopreservation on Cytokine Production by Human T Lymphocytes," Cryobiology,37:22-29, (1998).
Wardell, Seth et al., "A Cryopreserved Tumor Infiltrating Lymphocyte (TIL) Product for LN-144, Generated with an Abbreviated Method Suitable for High Throughput Commercial Manufacturing Exhibits Favorable Qualify Attributes For Adoptive Cell Transfer," P203 SITC 32nd Annual Meetin, National Harbor, MD, 1 pg., (Nov. 8-12, 2019).
Wardell, Seth et al., "Iovance Gen 2 TIL Manufacturing Process Produces Drug Products that Exhibit Favorable Quality Attributes for Adoptive Cell Transfer Across 5 Solid Tumor Indications," P226 SITC Annual Meetin, National Harbor, MD, (Nov. 6-10, 2019).
Weber Evan W. et al., "The Emerging Landscape of Immune Cell Therapies," Cell, 181;46-62, (2020).
Weber Evan W. et al., "Transient "rest" induces functional reinvigoration and epigenetic remodeling in exhausted CAR-T cells," BioRxIV, 1-37, (2020).
Weber, Amy Mackey et al., "Targeting 4-1BB in tumors enhanes anti-tumor immune responese," AACR Meeting 2403/207, Abstract, (2019).
Weber, J et al., "White paper on adoptive cell therapy for cancer with turner-infiltrating lymphocytes: a report of the CTEP subcommittee on adoptive cell therapy," Clin Cancer Res., 17(7):1664-1673, (2011).
Weinstein-Marom, H., et al., "Genetic Modification of tumor-Infiltrating Lymphocytes via Retroviral Transduction," Front Immunol., 11:584148, (2021).
Wherry, E John, "T cell exhustion," Nature Immunology, 12:492-499, (Jun. 2011).
Wilson Wolf ,"G-Rex Product Brochure" wilson Wolf Company Website,(2016). [Retrieved freom the internet Aug. 18, 2022: URL: <https://www.wilsonwolf.com/wp-content/uploads/2016/11/G-Rex-Brochure.pdf.].
WIPO Application No. PCT/GB2016/053949, PCT International Preliminary Report on Patentability dated Jun. 19, 2018.
WIPO Application No. PCT/GB2016/053949, PCT International Search Report and Written Opinion of the International Searching Authority dated Feb. 24, 2017.
WIPO Application No. PCT/GB2019/051745, PCT International Preliminary Report on Patentability dated Dec. 22, 2020.
WIPO Application No. PCT/GB2019/051745, PCT International Search Report and Written Opinion of the International Searching Authority dated Oct. 18, 2019.
WIPO Application No. PCT/GB2020/051790, PCT International Preliminary Report on Patentability dated Jan. 25, 2022.
WIPO Application No. PCT/GB2020/051790, PCT International Search Report and Written Opinion of the International Searching Authority dated Oct. 2, 2020.
WIPO Application No. PCT/IB2021/000878, PCT International Search Report and Written Opinion of the International Searching Authority dated Aug. 5, 2022.
WIPO Application No. PCT/IB2021/000882, PCT International Search Report and Written Opinion of the International Searching Authority dated May 13, 2022.
WIPO Application No. PCT/IB2021/000883, PCT International Search Report and Written Opinion of the International Searching Authority dated Jun. 15, 2022.
Chen, Zeyu et al., "TCF-1-Centered Trancriptional Network Drives an Effector versus Exhausted CD8 T Cell-Fate Decision," Immunity, 51:1-16, (2019).
Chesney, JA et al., "Trail in progress: A Phase 2 Multicenter Study (IOV-LUN-202) of Autologous Tumor-Infiltrating Lymphocyte (TIL) Cell Therapy (LN-145) in Patients with Metastatic Non-Small cell Lung Cancer (mNSCLC)," 7948 AACR Annual Meeting, New Orleans, LA, (Apr. 8-13, 2022).
Chesney, Jason Alan et al., "A phase II stude of autologous tumor infiltrating lymphocytes (TIL, LN-144/LN-145) in patients with solid tumors," J Clin Oncol., 37: Suppl., Abstract TPS2648, (2019).
Chesney, Jason Alan et al., "A phase II study of autologous tumor infiltrating lymphocytes (TIL, LN_144/LN_145) IN patients with solid tumors," 290a ASCO Annual Meeting, Chicogo. IL, (May 31-Jun. 4, 2019).

(56) References Cited

OTHER PUBLICATIONS

Chu, Talyn et al., "Charting the Roadmap of T Cell Exhaustion," Immunity, 52:724-26, (2020).

Chuang, Huai-Chia et al., "Epstien-Barr viris LMP1 inhibits the expression of SAP gene and upregulates Th1 cytokines in the pathogenesis of hemophagocytic syndrome," Blood, 106:3090-3096, (2005).

Cipherbio Data Team, "$18 Billion Invested in 135 Cell Therapy Companies," CipherBio News,(Aug. 18, 2021). [Retrieved from the internet Aug. 18, 2021: URL: <https://cipherbio.com>].

Clinicaltrials.gov, "Study of Lifilecel (LN-144), Autologous Tumor Infiltrating Lymphocytes, in the Treament of Patients With Metastatic Melanoma (LN-144), Trail record 5 of 14 for: iovance," (Dec. 23, 2019) [Retrieved from the Internet Dec. 23, 2019): <URL: https://www.clinicatials.gov/ct2/show/study/NCT02360579?term=iovance&draw=2&show_locs=Y#locn>].

Clinicaltrials.gov,"Sudy of Autologous Tumor Infiltrating Lymphocutes in Patients with Solid Tumors, Trial Record 1 of 1 for: IOV-COM-202," (Apr. 14, 2020). [Retrieved from the Internet Apr. 14, 2020: <URL: https://www.clinicaltrials.gov/ct2/show/NCT03645928?term=IOV-COM-2028draw=2&rank=1>].

Clover Biotech Research, "Iovance Biotherapeutics: Compelling Bet in Metastatic Melanoma," 6 pgs., Press Release, Aug. 14, 2018.

Cohen, Paul A. et al., "Pathological Chemotherapy response score is prognostic in tubo-ovarian high-grade serous carcinoma: A systematic review and meta-analysis of individual patient data," Gynecologic Oncology, 154:441-448, (2019).

Costantini, A. et al., "Effects of cryopreservation on lymphocyte immunophenotype and function," JIM, 278:145-155, (2003).

Creelan, Ben et al., "Durble complete responses to adoptive cell transfer using tumor infiltrating lymphocytes (TIL) in non-small cell lung cancer (NSCLC): A phase I trial," AACR Annual Meeting, CT056, Abstract, (2020).

Creelan, Benjamin C. et al., "Tumor-infiltrating lymphocyte treatment for anti-PD-1-resistant metastatic lung cancer: a phase 1 trial," Nature Medicine,27:1410-1418, (2021).

Crookes, H. et al., "Stability consideration for crypreserved starting material to facilitate large-scale production of ATMPs," Cytotheapy, 22:S26-S186, Abstracts, (2020).

Crowther, Michael D. et al., "T-Cell Gene Therapy in cancer Immunotherapy: Why It is No Longer Just CARs on the Road," 9(7):1588. (2020).

Crunkhorn, Sarah,"Designing cytokine mimics can optimize cancer therapy potential," Nature Review Drug Discovery, 18(3):173, (Mar. 2019).

Cubas, Rafael et al., "AKT inhibition during ex vivo TIL expansion enhance cytokine production and fuction while increaseing then population of less differenitiated (CD39-CD69-)CD8+ T-Cells," 54P ESMO Immuno-Oncology, Geneva, Switzerland, (Dec. 8-11, 2021).

Cytiva,"Improve outcomes for TIL therapies by tacking process challenges," Fierce Biotech [Retrieved from the Internet Nov. 24, 2020: https://www.flercebiotech.com/sponsored/improve-outcomes-for-till-therapies-by-tackling-process-challenges].

Dafni, U., et al., "Efficacy of adoptive therapy with tumor-infiltrating lymophcytes and recombinant interleukin-2 in advanced cutaneous melanoma: a systematic review and meta-analysis," Ann. Oncol., 30(12):1902, (2019).

Danaher, Patrick et al., "Gene expression markers of tumor-infiltrating leukocytes," NanoString Technologies, 1 pg., (Nov. 2016).

Dangaj, Denarda et al., "Cooperation between Constitutive and Inducible Chemokines Enables T Cell Engraftment and Immune Attack in Solid Tumors," Cancer Cell, 35:885-900, (2019).

Deleeuw, Ronald J. et al., "The Prognostic Value of FoxP3+ Tumor-Infiltrating Lymphocytes in Cancer: A Critical Review of the Literature," Clin Cancer Res, 18(11):3022-3029, (2012).

Demetriou et al. ("CD2 expression acts as a quantitative checkpoint for immunological synapse structure and T-cell activation." bioRxiv preprint doi: https://doi.org/101101/589440; this version posted Mar. 29, 2019). (Year: 2019).

Deniger, D.C., et al., "A Pilot Trail of the Combination of Vemurafenib with Adoptive Cell Therapy in Patients with Metastatic Melanoma," Clin Cancer Res., 23(2):351-362 (2017).

Devar, Dewakar et al., "High-dose interieukin-2 (HD IL-2) for advanced melanoma: a single center experience from the University of Pittsburgh Cancer Institute," Journal for Immuno Therapy of Cancer, 5:1-10, (2017).

Dillman, R.O., et al., "Continuous interieukin-2 and tumor-infiltrating lymphocytes as treatment of advanced melanoma. A national biotherapy study group trial," Cancer, 68(1):1-8, (1991).

Ding, Wei et al., "Prognostic value of tumor-infiltrating lymphocytes in hepatocellular carcinoma," Medicine, 97:e13301, (2018).

Donia et al., "Simplified protocol for clinical-grade tumor-infiltrating lymphocyte manufacturing with use of the Wave bioreactor," Cytotherapy 16(8):1117-1120, (Aug. 1, 2014).

Donia, M., et al., "Characterization and comparison of 'standard' and 'young' tomour- infiltrating lymphocytes for adoptive cell therapy at a Danish translational research institution." Scand. J Immunol. 75(2): 157-167, (2012).

Drachman et al., "Studies with chimeric Mpl/JAK2 receptors indicate that both JAK2 and the membrane-proximal domain of Mpl are required for cellular proliferation," J.Biol. Chem., 277(26):23544-23553, (2002).

Dudley, M.E., "Adoptive Cell Therapy for Patients with Melanoma," J. Cancer, 2:360-362, (2011).

Dudley, M.E., et al., "A phase I study of nonmyeloablative chemotherapy and adoptive transfer of autologous tumor antigen-specifflc T lymphocytes in patients with metastatic melanoma," J. Immunother., 25(3):243-251, (2002).

Dudley, M.E., et al., "Adoptive cell therapy for patients with metastatic melanoma: evaluation of intensive myeloablative chemoradiation preparative regimens," J. Clin. Oncol., 26(32):5233-5239, (2008).

Dudley, M.E., et al., "Adoptive cell transfer therapy." Semin. Oncol., 34(6):524-531, (2007).

Dudley, M.E., et al., "Adoptive-cell-tranfer therapy for the treatment of patients with caner," Nat. Rev. Cancer, 3(9):666-675, (2003).

Dudley, M.E., et al., "CD8+ enriched "young" tumor infiltrating lymphocytes can mediate regression of metastatic melanoma," Clin. Cancer. Res., 16(24):6122-6131, (2010).

Dudley, M.E., et al., "Generation of tumor-infiltrating lymphocyte cultures for use in adoptive transfer therapy for melanoma patients," J. Immunother., 26(4):332-342, (2003).

Dudley, M.E., et al., "Randomized sleection design trial evaluating CD8+enriced versus unselected tumor-infiltrating lymphocytes for adoptive cell therapy for patients with melanoma." J. Clin. Oncol., 31(17:2152-2159, (2013).

Dudley, M.E. et al., "Adoptive cell transfer therapy following non-myeloablative but lymphodleting chemotherapy for the treatment of patients with refractory metastatic melanoma," J. Clin. Oncol., 23(10):2346-2357, (2005).

Dudley, Mark E. et al., "Cancer Regression and Autoimmunity in Patients after Clonal Repopulation with Antitumor Lymphocytes," Science, 298:850-854, (2002).

Dunbar, P. Rod et al., "Cuting Edge: Rapid Cloning of tumor-Specific CTL Suitable for Adoptive Immunotherapy of Melanoma," JIM, 162:6959-6962, (1999).

Duraiswamy, Jaikumar et al., "Myeloid antigen-presenting cell niches sustain antitumor T cells and license PD-1 blockade via CD28 Costimulation," Cancer Cell, 391:1-20, (2021).

Eisenberge, Galit et al., "Soluble SLAMF6 Receptor Induces Strong CD8+ T-cell Effector Function and Improves Anti-melanoma Activity In Vivo," Cancer Immunology Research 6(2):127-138, (2018).

Elkord, Eyad, "Frequency of human T regulatpry cells in peripheral blood in significantly reduced by cryopreservation," JIM, 347:87-90, (2009).

Ellebaek et al. (Journal of Translational Medicine 2012, 10:169 doi: 10.1186/1479-5876-10-169). (Year: 2012).

(56) References Cited

OTHER PUBLICATIONS

Ellebaek, Eva etal., "Adoptive cell therapy with Autologous tumor infiltrating lymphocytes and low-dose Interleukin-2 in metastatic melanoma patients," Jouenal of Translational Medicine, 10:169, (2012).

Examiner Interview Summary Record (PTOL—413) dated Oct. 13, 2022 for U.S. Appl. No. 17/826,053.

Fan, Xiaozhou et al., "Engagement of the ICOS pathway markedly enhances efficacy of CTLA-4 blockade in cancer immunotherapy," J. Exp. Med., 211:715-725, (2014).

Fan, Xin-Juan et al., "Impact of cold Ischemic Time and Freeze-Thaw Cycles on RNA, DNA and Protein Quality in Colorectal Cancer Tissues Biobanking," Journal of cancer, 10(20): 49784988, (2019).

Garber, Ken, "Pursuit of tumor-infiltrating lymphocyte immunotherapy speeds up," Nature Biotechnology, 37:969-971, (Sep. 2019).

Harrison, Devin L. et al., "T-Cell Mechanobiology: Force Sensation, Potentiation, and Translation," Frontiers in Physics, 7(45):1-18, (Apr. 2019).

Hopewell, Emily L. et al., "Tumor Infiltrating Lymphocytes Streamlining a Complex Manufacturing Process," Cytotherapy, 21(3):307-314, (Mar. 2019).

IPEA/409—International Preliminary Report on Patentability dated Jun. 30, 2022 for WO Application No. PCT/GB20/053315.

Kooragayala, Keshav et al., "Adoptive Cellular Therapy for Metastatic Melanoma: The Road to Commercialization and Treatment Guidelines for Clinicians," Ann Surg Oncol, (Sep. 16, 2022).

Kumar, Amrendra et al., "Cell Therapy with TILs: Training and Taming T Cells to Fight Cancer," Frontiers in Immunology, 12(690499):1-15, (2021).

List of references Mailed on Oct. 7, 2022 for U.S. Appl. No. 17/733,875.

List of references Mailed on Sep. 28, 2022 for U.S. Appl. No. 17/826,081.

N.A. Giraldo, et al., Tumor-Infiltrating and Peripheral Blood T-cell Immunophenotypes Predict Early Relapse in Localized Clear Cell ReMI Cell Carcinoma, C. Clin Cancer Res (Aug. 1, 2017) 23(15):4416-4428.

Non-Final Rejection dated Oct. 7, 2022 for U.S. Appl. No. 17/733,875.

Non-Final Rejection dated Sep. 28, 2022 for U.S. Appl. No. 17/826,072.

Non-Final Rejection dated Sep. 28, 2022 for U.S. Appl. No. 17/826,081.

Outgoing—ISA/210—International Search Report dated May 3, 2021 for WO Application No. PCT/GB20/053315.

Outgoing—ISA/210—International Search Report dated Apr. 19, 2018 for WO Application No. PCT/GB18/050088.

\* cited by examiner

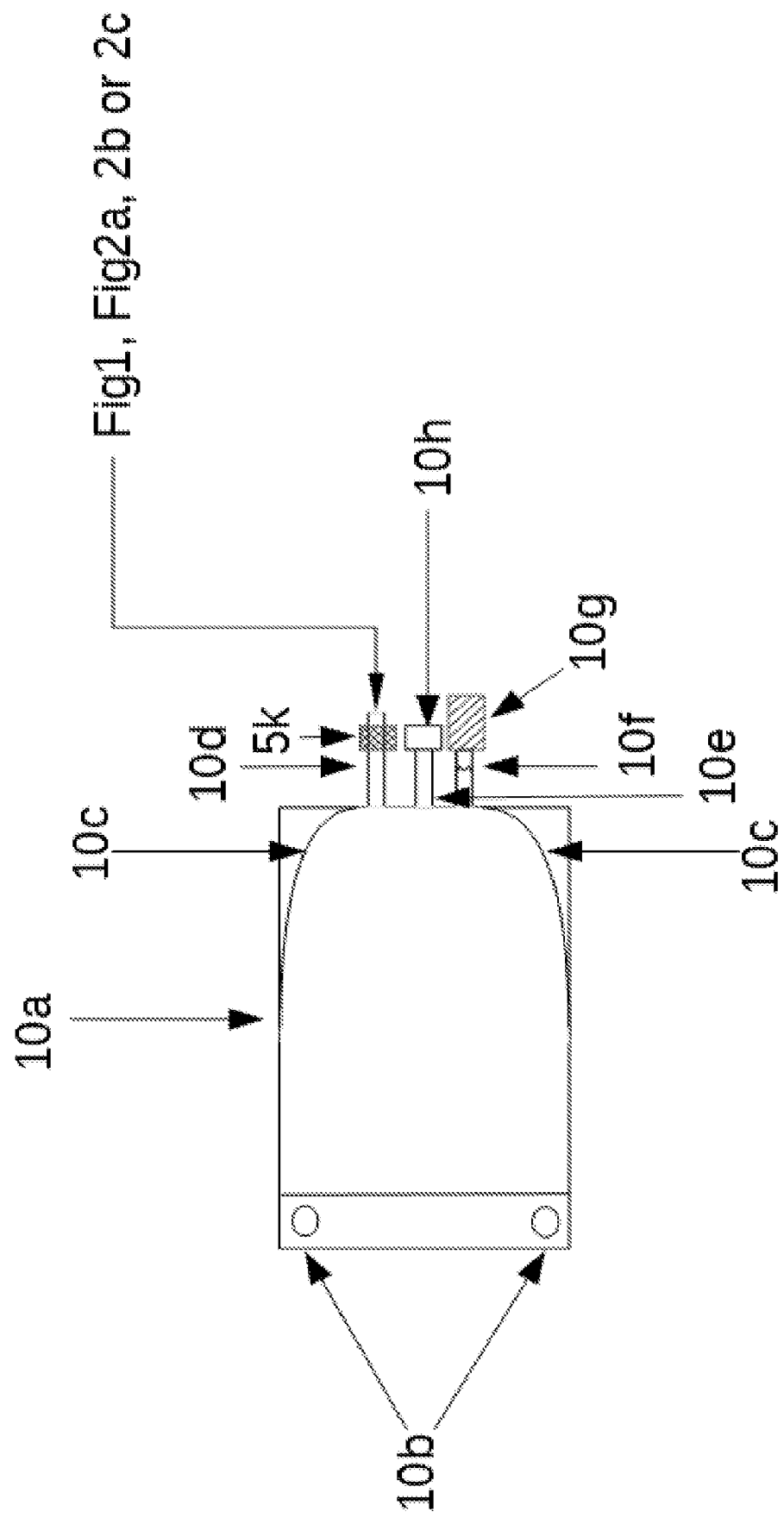

| Tissue Sample Dimensions | Volume of digestion media (ml) | 1st Step | 2nd Step | 3rd Step | Fully disaggregation |
|---|---|---|---|---|---|
| 1 x 1 x 1 (~1 g) | 25 | 3 min disaggregation & 30 min @ 37°C | 1 min disaggregation & 30 min @ 37°C | 1 min disaggregation | Y |
| 1 x 1 x 1 (~1g) | 25 | 1 min disaggregation & 30 min @ 37°C | 1 min disaggregation & 30 min @ 37°C | 1 min disaggregation | Y |
| 1.5 x 1.5 x 1.5 (~3 g) | 25 | 5 min disaggregation & 30 min @ 37°C | 1 min disaggregation & 30 min @ 37°C | 1 min disaggregation | Y |
| 2 x 2 x 2 (~7 g) | 25 | 7 min disaggregation & 30 min @ 37°C | 1 min disaggregation & 30 min @ 37°C | 1 min disaggregation | Y |
| 2 x 2 x 2 (~7 g) | 50 | 10 min disaggregation & 30 min @ 37°C | 1 min disaggregation & 30 min @ 37°C | 1 min disaggregation | N (30-50% intact) |

FIG. 5B

ASEPTIC TISSUE PROCESSING METHOD, KIT AND DEVICE

CROSS-REFERENCE TO RELATED APPLICATIONS

This application is a continuation of U.S. application Ser. No. 16/477,366 filed Jul. 11, 2019, which is a national stage entry of PCT/GB2018/050088 filed Jan. 12, 2018, which claims priority to GB Application No. 1700621.4 filed Jan. 13, 2017, each of which is hereby incorporated by reference in its entirety.

The present invention concerns a kit and a semi-automatic device using that kit for aseptic disaggregation of solid tissue derived eukaryotic cells into either single cells or small cell number aggregates. The invention further relates to a semi-automatic aseptic tissue processing method comprising: a process for aseptic disaggregation of solid tissue derived eukaryotic cells into either single cells or small cell number aggregates and their further processing.

BACKGROUND

The conditions during solid tissue disaggregation and time taken to harvest the cells have a substantial impact on the viability and recovery of the final cellularised material. Typically a solid tissue derived cell suspension, that is obtained, comprises a wide variety of different cell types and the disaggregation media and tissue debris or fluids. Often, selective targeting and or isolation of an individual or multiple cell types is prerequisite for the starting material prior to manufacture of regenerative medicines, adoptive cell therapies, ATMPs, diagnostic in vitro studies or scientific research. Generally these selection or enrichment techniques rely on one of the following properties: size, shape, density, adherence or strong protein: protein interactions (i.e. antibody: antigen) or providing a growth supporting environment by controlling the culture conditions or more complex cell marker interactions associated with semi-permanent or permanent coupling to magnetic or non-magnetic solid or semi-solid phase substrates can be used.

For enrichment, isolation or selection in principle any sorting technology can be used. This includes for example affinity chromatography or any other antibody-dependent separation technique known in the art. Any ligand-dependent separation technique known in the art may be used in conjunction with both positive and negative separation techniques that rely on the physical properties of the cells. An especially potent sorting technology is magnetic cell sorting. Methods to separate cells magnetically are commercially available e.g. from Thermo fisher, Miltenyi Biotech, Stem cell Technologies, Cellpro, Seattle, Advanced Magnetics, Boston or Quad Technologies Boston. For example, monoclonal antibodies can be directly coupled to magnetic polystyrene particles like Dynal M 450 or similar magnetic particles and used e.g. for cell separation. The Dynabeads technology is not column based, instead these magnetic beads with attached cells enjoy liquid phase kinetics in a sample tube, and the cells are isolated by placing the tube on a magnetic rack. However, in a preferred embodiment for enriching, sorting and/or detecting neuronal cells from a sample containing neuronal cells according the present invention monoclonal antibodies are used in conjunction with colloidal superparamagnetic microparticles having an organic coating by e.g. polysaccharides (Magnetic-activated cell sorting (MACS) technology (Miltenyi Biotec, Bergisch Gladbach, Germany)). These particles (nanobeads or MicroBeads) can be either directly conjugated to monoclonal antibodies or used in combination with anti-immunoglobulin, avidin or antihapten-specific MicroBeads or coated with other mammalian molecules with selective binding properties.

Magnetic particle selection technologies such as those described above, allows cells to be positively or negatively separated by incubating them with magnetic nanoparticles coated with antibodies or other moieties directed against a particular surface marker. This causes the cells expressing this marker to attach to the magnetic nanoparticles. Afterwards the cell solution is placed within a solid or flexible container in a strong magnetic field. In this step, the cells attach to the nanoparticles (expressing the marker) and stay on the column, while other cells (not expressing the marker) flow through. With this method, the cells can be separated positively or negatively with respect to the particular marker(s).

In case of a positive selection the cells expressing the marker(s) of interest, which attached to the magnetic column, are washed out to a separate vessel, after removing the column from the magnetic field.

In case of a negative selection the antibody or selective moiety used is directed against surface markers(s) which are known to be present on cells that are not of interest. After application of the cells/magnetic nanoparticles solution onto the column the cells expressing these antigens bind to the column and the fraction that goes through is collected, as it contains the cells of interest. As these cells are non-labelled by the selective antibodies or moiety(s) coupled to nanoparticels, they are "untouched".

The known manual or semi-automated solid tissue processing steps are labour-intensive and require a knowledge of the art.

In addition where the material is used for therapeutic purposes, the processing requires strict regulated environmental conditions during handling the cell cultures, for example tissue processing as apart of or prior to disaggregation; enzymatic digestion and transfer into storing devices or incubation conditions for disaggregation/cellularisation and viable tissue yields. Typically this process would require multiple pieces of laboratory and tissue processing equipment, and personal with the skills and knowledge of the scientific art with critical stages contained within either hazard containment or tissue processing facility(s) aseptic environment(s) in order to perform the same activity safely and also minimise the risk of contamination(s).

The invention therefore arises from a need to provide improved solid tissue processing, including an apparatus/device that undertakes said processing that achieves the unmet need described above.

SUMMARY OF INVENTION

The present invention concerns a single use aseptic kit comprising a disaggregation module for receipt and processing of material comprising solid mammalian tissue; an optional enrichment module for filtration of disaggregated solid tissue material and segregation of non-disaggregated tissue and filtrate; and a stabilisation module for optionally further processing and/or storing disaggregated product material, wherein each of said modules comprises one or more flexible containers connected by one or more conduits adapted to enable flow of the tissue material there between; and wherein each of said modules comprises one or more ports to permit aseptic input of media and/or reagents into the one or more flexible containers.

In prior art the tissue may undergo physical and or enzymatic disaggregation/cellularisation in a single container. In the present invention sets of containers which are interconnected and have specific separate functions maintain an aseptically closed system to process, optionally enrich but stabilise the disaggregated and cellularised solid tissue product. Essentially the invention provides a rapid pre-sterilised environment to minimise the time required and risk of contamination or operator exposure during the processing of the solid tissue.

The kit described here allows for closed solid tissue processing eliminating the risk of contamination of the final cellularised product compared to standard non-closed tissue processing. This is especially when the process is performed within a tissue retrieval/procurement site and requires storage prior to final cell processing for its ultimate utility. In addition, safety of the operator is increased due to reduction of direct contact with biological hazardous material which may contain infectious organisms such as viruses.

The kit also enables either all of or a portion of the finally processed cellularised material to be stabilised for either transport or storage prior to being processed for its ultimate utility.

The invention will enable the solid tissue to be processed at the time of tissue retrieval, or later if required, without impact upon the retrieval procedure or the viability of the cellularised product.

In some embodiments employing optional enrichment via a form of physical purification to reduce impurities such as no longer required reagents; cell debris; non-disaggregated tissue and fats. A single cell or small cell number aggregates can be enriched for stabilisation after disaggregation by excluding particles and fluids of less than 5 µm or incompletely disaggregated material of or around 200 µm across or larger but this will vary upon the tissue and the efficiency of disaggregation and various embodiments in the form of tissue specific kits may be employed depending upon the tissue or ultimate utility of the disaggregated solid tissue.

In some embodiments the one or more flexible containers comprise a resilient deformable material. The one or more flexible containers of the disaggregation module may comprise one or more sealable openings. The one or more flexible containers of the disaggregation module and/or the stabilisation module may also comprise a heat sealable weld.

In further embodiments the one or more flexible containers that are part of any module comprise internally rounded edges.

The one or more flexible containers of the disaggregation module may comprise disaggregation surfaces adapted to mechanically crush and shear the solid tissue therein.

Further, the one or more flexible containers of the enrichment module may comprise a filter adapted to retain a retentate of cellularised disaggregated solid tissue.

In embodiments, one or more flexible containers of the stabilisation module comprise media formulation for storage of viable cells in solution or in a cryopreserved state. In some embodiments the In further embodiments the kit further comprises a radio frequency or other digitally recognisable identification tag so that it may be scanned and recognised during automated processing, such as with/in the automated device in embodiments of the present invention. Crucially the tag provides information about the conditions and steps required to be auto processed, so simply by scanning the kit, any automated system used with the kit to process the tissue can be undertaken without further intervention or contamination. Once the tissue sample has been placed in the disaggregation module, it can for example be sealed, manually, or automatically, before processing begins.

In this regard, in preferred embodiments that include a device, the kit associated tag is detected by the device's processor and the device then runs a specific program according to a type of disaggregation and/or enrichment and/or stabilisation process; one or more types of media used in those processes; including an optional freezing solution suitable for controlled rate freezing. Put another way, the kit is therefore be readable by an automated device used to execute a specific fully automatic method for processing the specific tissue when inserted to such a device.

The invention is particularly useful in a sample processing, particularly automated processing. Thus, in a further aspect the invention concerns use of the single use aseptic kit described above in a semi-automated process for the aseptic disaggregation and/or enrichment and stabilisation of mammalian cells or cell aggregates.

A particular advantage is that solid tissue disaggregation (and optional processes including all described manipulations herein described required to achieve optimal results) can be performed in a closed system, i.e. an aseptic process with minimal risk of contaminations and with minimal user knowledge.

The invention further relates to an automated device for semi-automated aseptic disaggregation and/or enrichment and stabilisation of cells or cell aggregates from mammalian solid tissue comprising a programmable processor and the single use aseptic kit as described in any of the before mentioned examples above.

In embodiments, as previously described, the device may have a comprising radio frequency identification tag reader to recognise the single use kit. The programmable processor is capable of recognising the single use aseptic kit via its tag and subsequently able to execute the kit programme which defines the type of disaggregation, enrichment and stabilisation processes together with the respective media types required for those processes.

In this regard, the programmable processor is adapted to communicate with and control one or more of: the disaggregation module; the enrichment module; and the stabilisation module of the device. The device, including its processor, may therefore have multiple functionality to assess the flow of materials through the kit making decisions of when a step is completed as part of the pre-programmed functions and the feedback the device gets from its sensors.

For example, the programmable processor may control the disaggregation module to enable a physical and/or biological breakdown of the solid tissue material in that container. The programmable processor may also control the disaggregation module to enable a physical and enzymatic breakdown of the solid tissue material.

In some embodiments the enzymatic breakdown of the solid tissue material is by the selection and provision of one or more media enzyme solutions selected from collagenase, trypsin, lipase, hyaluronidase, deoxyribonuclease, Liberase H1, pepsin, or mixtures thereof.

In addition or alternatively the programmable processor may control disaggregation enabling the surfaces within the disaggregation flexible containers to mechanically crush and shear the solid tissue. In embodiments, the disaggregation surfaces are controlled by mechanical pistons, for example.

In some embodiments, the programmable processor controls the stabilisation module to cryopreserve the enriched disaggregated solid tissue in the container, for example, this may be achieved by using a programmable temperature setting, a condition which is determined by reading the tag of the kit inserted in the device.

In some embodiments, to undertake different functions of the process, one or more of the additional components of the device and/or kit are provided. Such features may be available in any combination. This may include for example: sensors in the device capable of recognising whether a disaggregation process has been completed in the disaggregation module of the kit prior to transfer of the disaggregated solid tissue to the optional enrichment module; weight sensors to determine an amount of media required in the containers of one or more of the disaggregation module; the enrichment module; and/or the stabilisation module and means to control that transfer of material between respective containers; and temperature sensors to control the temperature within the containers of the one or more of the disaggregation module; the enrichment module; and/or the stabilisation module.

Other possible features include an optional bubble sensor to control the transfer of media between the input and output ports of each container in the module; one or more pumps may provide means to control the transfer of media between the input and output ports; and/or pressure sensors to assess the pressure within the enrichment module; valves to control an optional tangential flow filtration process within the enrichment module; and/or one or more clamps to control the transfer of media between the input and output ports of each module.

For example, the programmable processor is adapted to maintain an optimal storage temperature range in the stabilisation module until the container is removed; or executes a controlled rate of freezing.

These embodiments of the device and kit allow solid tissue derived cells or cell aggregates to be: stored for short periods (minutes to days) or stored for long periods (multiple days to years) prior to their ultimate utility depending on the type or stabilisation process used with the stabilisation module.

For ease of use, the device of the invention may further comprise a user interface. That interface may comprise a display screen to display instructions that guide a user to input parameters, confirm pre-programmed steps, warn of errors, or combinations thereof.

In many cases it is desirable that the automated device is adapted to be transportable and thus may comprise dimensions that permit easy manoeuvrability and/or aid movement such as wheels, tyres, handles and the like.

The final cellular material product can then be used for but not limited to either: regenerative medicine, adoptive cell therapies, ATMPs, diagnostics or to further the basic scientific understanding of tissue, cell function or organism function.

The combination of an aseptic kit, automated processing device and associated media formulations, which can disaggregate solid tissues to provide functional living cells or the product of the cells for subsequent therapeutic, diagnostic or scientific use, is therefore highly desirable.

In some embodiments the cells produced using the kit and/or device of the invention are useful for providing functional living cells and maybe cultured further for that use. Cell culture is a process by which cells are grown outside the original host using controlled environmental and supportive conditions which vary by cell type and organism. These are often sterile artificial vessels which allow gas and temperature to be maintained and either manual or automated changes in essential nutrients, metabolites, growth factors and gases which enable regulation of the cells requirements to survive and in most cases thrive. Cell culture requirements differ broadly by the type of cell(s) and its required purpose. Cell culture conditions can be optimised for cell expansion, cell differentiation or manufacturing of different phenotypes of the cell or its products. The most commonly varied factor in culture systems is the cell culture medium, for which a vast number of recipes is known (see for example "Cell Culture Techniques" Humana Press, 1st. Edition, 2011)

In some embodiments disaggregated or cellularised material produced by the device and kit can be useful as the starting material to isolate specific cell populations which are grown out using stimulation or non-required cells are inhibited or apoptosis/cell death is induced resulting in a semi/purified population.

Such cells can be further sorted by one or more of the following processes: Fluorescence-activated cell sorting using antibody/protein labelling or natural fluorescence; Magnetic separation of cells, e.g. the magnetic activated cell sorting (MACS technology, Miltenyi Biotec GmbH, Germany). This technology requires a marker that allows direct separation of the cells of interest by an antibody coupled to a magnetic microbead (Miltenyi et al., Cytometry 1990; 11:231-238). Alternatively, where it is not possible or not desirable to actively select the target population a process of negative isolation can be employed. In this approach, non-target cells are magnetically labelled and depleted, thereby leaving the unlabelled cells of interest; Label free cell separation and sorting using physical separation methods where either the target is not known, is a mixed population and physical cell (or clumps of cells) characteristics can be used to separate the cellular material from the current media to: remove impurities or reagents that are no longer required such as enzymes, cell debris, connective tissue, fat & mineral deposits; or exchange fluids which may be better for stabilising the cells for distribution and/or storage. It is envisaged that embodiments of the invention may include such functionality within the parameters of the processor or the automated device and operating system.

For example, the purity, of the disaggregated and cellularised solid tissue product, can be further increased if one or more cell surface marker(s) are used to select for or deplete a subpopulation of cells either as an independent step within the process or after processing using the methods described.

The present invention also relates to a method for enhanced semi-automated disaggregation cellularisation and storage of tissue derived cells. Optionally, steps of enrichment, formulation and cryopreservation are also provided.

In a further aspect of the invention, there is provided a semi-automatic aseptic tissue processing method comprising: automatically determining aseptic disaggregation tissue processing steps and one or more further tissue processing steps and their associated conditions from a digital tag identifier on an aseptic processing kit, optionally in accordance with the kit described herein; placing a tissue sample into a flexible plastic container of the aseptic processing kit; and processing the tissue sample by automatically executing the one or more tissue processing steps by communicating with and controlling the disaggregation module; the optional enrichment module; and the stabilisation module.

The one or more automatically executed processes may be selected from one or more of:

1) transferring media, preferably enzyme media, into the disaggregation chamber (for example, in accordance with the sealable disaggregation flexible container of the kit of the invention). The media maybe transferred into the disaggregation chamber, or in one embodiment also enters and collects enzymes prior to disaggregation using one or more embodiments of the invention, e.g. a mechanism such as weight sensors which will assess the required amount of media to add either determined by: direct operator input or weight of solid tissue. Incubating with the media at an optimal temperature of between 30 & 37° C. but could be as low as 0° C. upto 40° C. for at least 1 minute to several hours but more preferable 15 to 45 minutes.

2) undertaking physical disaggregation for a minimum of a few seconds up to several hours with an optimal time of between 1 and 10 minutes required to break up the solid tissue until there is no visual change (FIG. 5A). The disaggregation is designed to compress the tissues using a variable speed and time depending upon the time taken to disaggregate and feedback via sensors within the disaggregation module.

Steps 1) or 2) may be repeated until the tissue stops changing or has been disaggregated into a liquid cell suspension (whichever comes 1st monitored by a sensor in the disaggregation module).

3) removing disaggregated tissues, associated material and impurities by passing the disaggregated tissue and media through one or more filters enabling optional enrichment of the cell suspension. Direct pass through one or more mechanical filters with holes at least >0.1 µm to 1000 µm but most preferably between 50 and 250 µm and more preferably 100 µm to 200 µm. Alternatively, other separation methods maybe used such as:
  I density based separation using centrifugation and/or sedimentation with or without a cell aligned density retention solution (e.g. Ficoll-paque GE Healthcare).
  II Hydrodynamic filtration where fluid flow and flow obstructing materials enhance the resolution and fractionation of the cells and impurities based on size and shape
  III. Field flow fractionation where an applied field (e.g. flow, electric, gravitational, centrifugal) acts in a perpendicular or reverse direction to the selection flow (e.g. Tangential flow filtration, Hollow fibre flow filtration, Asymmetric flow filtration, Centrifugal flow filtration). In which case: cells or impurities which are most responsive to the force are driven to the wall where flow is lowest and therefore a long retention time; while cells or impurities which are least responsive to the force remain laminar to the flow and elute quickly (tangential flow filtration)
  IV Acoustophoresis where one or more an acoustic frequency(ies) tuned to or harmonized with populations of cells or impurities is used to drive the required cells or impurities in a tangential path to the input stream.

4. Re-suspending the disaggregated cell product in fresh or additional media. This could be a cell enrichment media in order to undergo an independent targeted enrichment procedure or direct cell culture or cold storage media (such as HypoThermosol® from BioLife Solutions).

5. Transferring to a stabilising module containers for storage for hours to days or 6. Re-suspending in, or addition of a, cryoprotectant—a freezing solution for storage of the disaggregated solid tissue derived product for days to years (such as CryoStor® Freezing solution from BioLife Solutions) and transferring to one or more flexible stabilising module having a cryopreservation container(s)

7. Performing a controlled rate freezing process

8. Separating the aseptic processing kit from the device for independent storage or distribution.

During such steps it is apparent that the disaggregated module and the storage module may comprise one and the same flexible container, for receiving the sample and storing the sample and a further flexible container for housing the media for disaggregation. In some embodiments the same flexible containers are part of different modules of the kit.

BRIEF DESCRIPTION OF THE FIGURES

FIG. 3A (also referred to herein as FIG. 3a or FIG. 3a, and the like) depicts an embodiment of the subject matter described herein.

FIG. 5B (also referred to herein as FIG. 5B, and the like) reports data on tissue size versus disaggregation time, incubation and volume in a 100mL fill flexible container.

DETAILED DESCRIPTION

Figure 1:
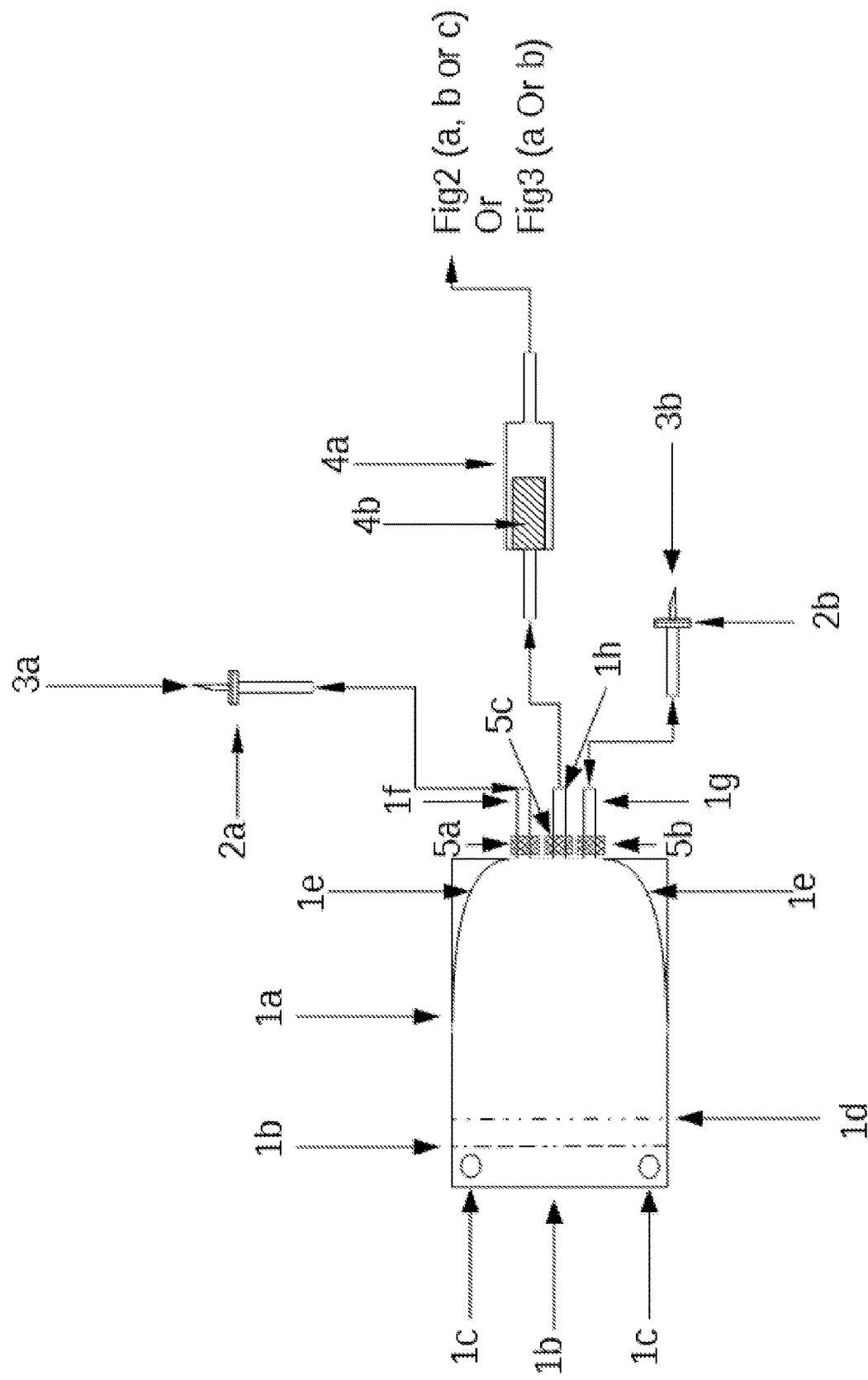
FIG. 1 (also referred to herein as FIG. 1, FIG. 1 or FIG. 1, and the like) depicts an embodiment of the subject matter described herein.

The processing of tissue to cells according to the kit, semi-automated device and methods of present disclosure are described further in the accompanying examples and figures numbered 1 to 7.

Moreover, by utilising the kit, device and processes described herein, in conjunction with ordinary skills in the art, further embodiments of the present disclosure can be readily identified. Those skilled in the art will readily understand known variations.

Definitions of the Disclosure

Unless defined otherwise, technical and scientific terms used herein have the same meaning as commonly understood by one of ordinary skill in the art to which this invention belongs.

"depletion" as used herein refers to a process of a negative selection that separates the desired cells from the undesired cells which are labelled by one marker-binding fragment coupled to a solid phase.

"disaggregation or disaggregate" as used herein refers to the transformation of solid tissue into a single cells or small cell number aggregates where a single cell as a spheroid has a diameter in the range of 5 µm, 6 µm, 7 µm, 8 µm, 9 µm, 10 µm, 20 µm, 30 µm, 40 µm, 50 µm, 60 µm, 70 µm, 80 µm, 90 µm, 100 µm or more where this is more usually between 7 to 20 µm.

"cellularised or cellularisation" as used herein refers to the process of disaggregation where by the solid tissue a multicellular material generally made up of multiple cell lineages/types is broken down into small numbers of cells including but not limited to one cell but could be multiple cells of various lineages or cell types in very small numbers i.e. clump of cells or cell aggregates.

"engineered" as used herein refers to either addition of nucleic material or factors which change the tissue derived cell function from their original function to have a new or improved function for its ultimate utility.

"filtrate" as used herein refers to the material that passes through a filter, mesh or membrane.

"flexible container" as used herein refers to a flexible packaging system in multiple formats with one or more different types of film. Each film type is selected to provide specific characteristics to preserve the physical, chemical, and functional characteristics of the sterile fluids, solid tissue derived cellular material and the container integrity depending upon the step of the process.

"freezing solution" or "cryopreservation solution" also referred in the field to as the cryoprotectant is a solution that contains cryoprotective additives. These are generally permeable, non-toxic compounds which modify the physical stresses cells are exposed to during freezing in order to minimise freeze damage (i.e. due to ice formation). Most commonly a % Vol/Vol of one or more of the following: Dimethylsulphoxide (DMSO); Ethylene glycol; Glycerol; 2-Methyl-2,4-pentanediol (MPD); Propylene glycol; Sucrose; & Trehalose.

"media" means various solutions known in the art of cell culturing, cell handling and stabilisation used to reduce cell death, including but not limited to one or more of the following media Organ Preservation Solutions, selective lysis solutions, PBS, DMEM, HBSS, DPBS, RPMI, Iscove's medium, X-VIVO™, Lactated Ringer's solution, Ringer's acetate, saline, PLASMALYTE™ solution, crystalloid solutions and IV fluids, colloid solutions and IV fluids, five percent dextrose in water (D5W), Hartmann's Solution. The media can be standard cell media like the above mentioned media or special media for e.g. primary human cell culture (e.g. for endothelia cells, hepatocytes or keratinocytes) or stem cells (e.g. dendritic cell maturation, hematopoietic expansion, keratonocytes, mesenchymal stem cells or T cell expansion). The media may have supplements or reagents well known in the art, e.g. albumins and transport proteins, amino acids and vitamins, antibiotics, attachments factors, growth factors and cytokines, hormones, metabolic inhibitors or solubilising agents. Various media are commercially available e. g. from ThermoFisher Scientific or Sigma-Aldrich.

"non-labelled" or "untouched" as used herein refers to the cells which are not bound by one marker-binding fragment coupled to a solid phase. The non-labelled, untouched cell fraction contains the desired target cells.

"non-target cells" as used herein refers to cells which are specifically bound by one marker-binding fragment which is coupled to a solid phase that is used to remove an unwanted cell type.

"positively separated" as used herein refers to the active separation of cells which are bound by one marker-binding fragment coupled to a solid phase and these cells are the required population of cells.

"negatively separated" as used herein refers to the active separation of cells which are bound by one marker-binding fragment coupled to a solid phase and these cells are not the required population of cells.

"purity" as used herein refers to the percentage of the target population or populations desired from the original solid tissue.

"regenerative medicine(s)", "adoptive cell therapy(ies)" or "advanced therapy medicinal product(s)" are used interchangeably herein to refer to cellular material that is used for therapeutic purposes of one or more mammals either by: the action of a part of or all of the cellular material; the supportive actions of a part of or all of the cellular material with the aim to improve the wellbeing of the mammal after application. The therapeutic cells can either be used directly or may require further processing, expansion and/or engineering to provide these actions.

"sample" as used herein refers to a sample containing cells in any ratio. Preferentially, these cells are viable. But, these cells can also be fixed or frozen cells which may be used for subsequent nucleic acids or protein extraction. The samples may be from animals, especially mammals such as mouse, rats or humans. Any compressible solid tissue that contains cells can be used. The invention is illustrated mainly through the isolation of hematopoietic and cancer cells from solid tumour tissue. However, the invention relates to a method for isolation of a breadth of cells from any mammalian solid tissue.

"marker" as used herein refers to a cell antigen that is specifically expressed by a certain cell type. Preferentially, the marker is a cell surface marker, so that enrichment, isolation and/or detection of living cells can be performed.

"solid phase" as used herein refers to the coupling of the marker-binding fragment, e.g. an antibody, bound to another substrate(s), e.g. particles, fluorophores, haptens like biotin, polymers, or larger surfaces such as culture dishes and microtiterplates. In some cases the coupling results in direct immobilization of the antigen-binding fragment, e.g. if the antigen-binding fragment is coupled to a larger surface of a culture dish. In other cases this coupling results in indirect immobilisation, e.g. an antigen-binding fragment coupled directly or indirectly (via e.g. biotin) to a magnetic bead is immobilised if said bead is retained in a magnetic field. In further cases the coupling of the antigen-binding fragment to other molecules results not in a direct or indirect immobilization but allows for enrichment, separation, isolation, and detection of cells according to the present invention, e.g. if the marker-binding fragment is coupled to a chemical or physical moiety which then allows discrimination of labelled cells and non-labelled cells, e.g. via flow cytometry methods, like FACSsorting, or fluorescence microscopy.

"solid tissue" as used herein refers to a piece or pieces of animal derived mammalian solid tissue which by its three dimensions i.e. length, breadth and thickness as a geometrical body is larger than the size of multiple individual cell based units and often contains connective materials such as collagen or a similar matrix that make up structure of the tissue whereby said solid tissue cannot flow through tubes or be collected by a syringe or similar small conduit or receptacle and is i.e. with dimensions in the range of 500 µm, 1 mm, 2 mm, 3 mm, 4 mm, 5 mm, 1 cm, 2 cm, 3 cm, 4 cm, 5 cm, 10 cm, 20 cm, 30 cm or more "particle" as used herein refers to a solid phase such as colloidal particles, microspheres, nanoparticles, or beads. Methods for generation of such particles are well known in the field of the art. The particles may be magnetic particles or have other selective properties. The particles may be in a solution or suspension or they may be in a lyophilised state prior to use in the present invention. The lyophilized particle is then reconstituted in convenient buffer before contacting the sample to be processed regarding the present invention.

"magnetic" in "magnetic particle" as used herein refers to all subtypes of magnetic particles which can be prepared with methods well known to the skilled person in the art, especially ferromagnetic particles, superparamagnetic particles and paramagnetic particles. "Ferromagnetic" materials are strongly susceptible to magnetic fields and are capable of retaining magnetic properties when the field is removed. "Paramagnetic" materials have only a weak magnetic susceptibility and when the field is removed quickly lose their weak magnetism. "Superparamagnetic" materials are highly magnetically susceptible, i.e. they become strongly magnetic when placed in a magnetic field, but, like paramagnetic materials, rapidly lose their magnetism.

"marker-binding fragment" as used herein refers to any moiety that binds preferentially to the desired target molecule of the cell, i.e. the antigen. The term moiety comprises, e.g., an antibody or antibody fragment. The term "antibody" as used herein refers to polyclonal or monoclonal antibodies which can be generated by methods well known to the person skilled in the art. The antibody may be of any species, e.g. murine, rat, sheep, human. For therapeutic purposes, if non-human antigen binding fragments are to be used, these can be humanized by any method known in the art. The antibodies may also be modified antibodies (e.g. oligomers, reduced, oxidized and labelled antibodies). The term "antibody" comprises both intact molecules and antibody fragments, such as Fab, Fab', F(ab')2, Fv and single-chain antibodies. Additionally, the term "marker-binding fragment" includes any moiety other than antibodies or antibody fragments that binds preferentially to the desired target molecule of the cell. Suitable moieties include, without limitation, oligonucleotides known as aptamers that bind to desired target molecules (Hermann and Pantel, 2000: Science 289: 820-825), carbohydrates, lectins or any other antigen binding protein (e.g. receptor-ligand interaction).

"retentate" as used herein refers to the material that does not pass through a filter, mesh or membrane.

"ultimate utility" as used herein refers to manufacture of or direct use in regenerative medicines, adoptive cell therapies, ATMPs, diagnostic in vitro studies or scientific research.

With reference to FIG. 1 there is disclosed:
1a Flexible container for: disaggregation; and digestion in the embodiment involving enzymatic digestion.
1b Open end for transfer of solid tissue materials into container 1a
1c hanging holes to support container 1a
1d target heat weld location to seal container 1a using heat welder 13m
1e rounded edges on internal container 1a surfaces to reduce losses which may occur as part of transfer to examples illustrated in FIG. 2 (a, b or c) or FIG. 3 (a or b)
1f tubing 1f enables media 3a to be transferred into container 1a via sterile filter 2a
1g in example tubing 1g enables digestion enzymes 3b to be transferred into container 1a via sterile filter 2b
1h after disaggregation, especially involving enzymatic digestion a phase of incubation, the mixture is transferred out via tubing 1h via filter unit 4a containing filter 4b prior to entering
2a spike and sterile filter for media 3a
2b spike and sterile filter for enzymes 3b in one example, where enzymes are required
3a media for disaggregation and in one example enzymatic digestion
3b enzymes for disaggregation in one example
4a flexible filter unit
4b non-disaggregated tissue filter
5a tubing clamp to allow media (3a) to enter the flexible container 1a via filter 2a
5b in one example where enzymes are used a tubing clamp will allow enzymes (3b) to enter the flexible container 1a via filter 2b
5c tubing clamp to allow contents of flexible container 1a to pass via filter 4a into one or more examples identified in FIG. 2 (a-c) Or FIG. 3 (a or b)

Figure 2A:
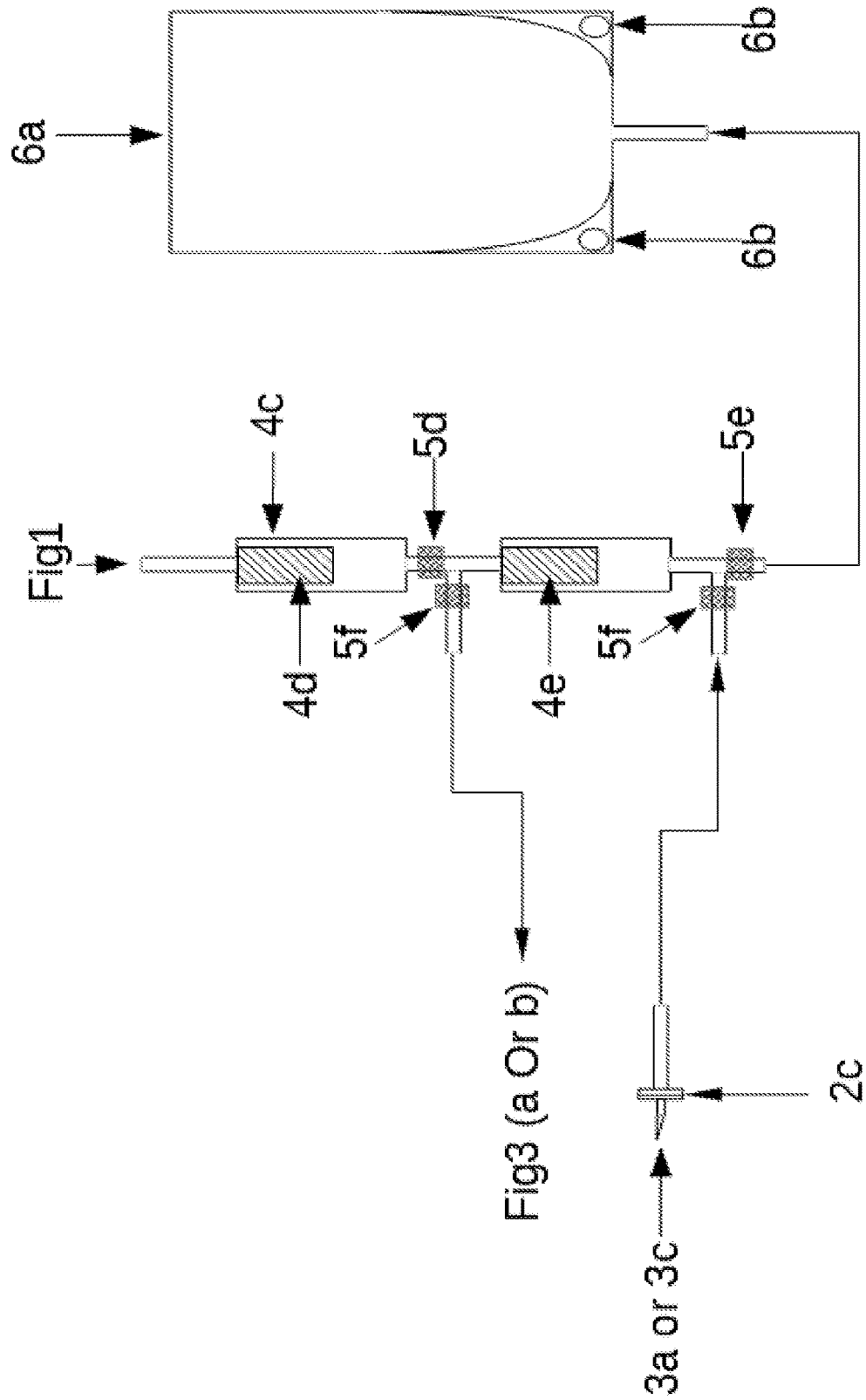
FIG. 2A (also referred to herein as FIG. 2a, FIG. 2a or FIG. 2a, and the like) depicts an embodiment of the subject matter described herein.
Figure 2B:
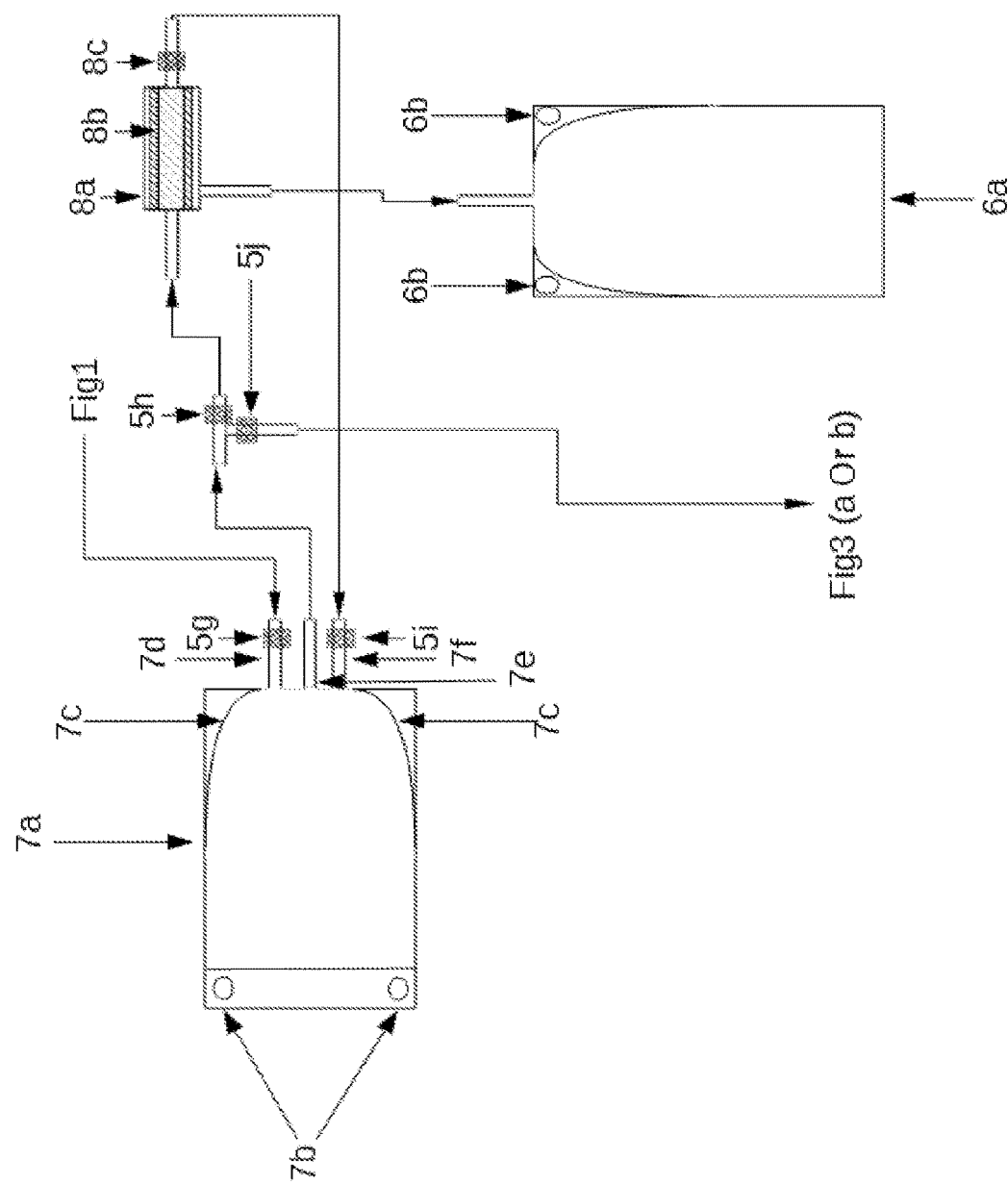
FIG. 2B (also referred to herein as FIG. 2b, FIG. 2b or FIG. 2b, and the like) depicts an embodiment of the subject matter described herein.
Figure 3B:
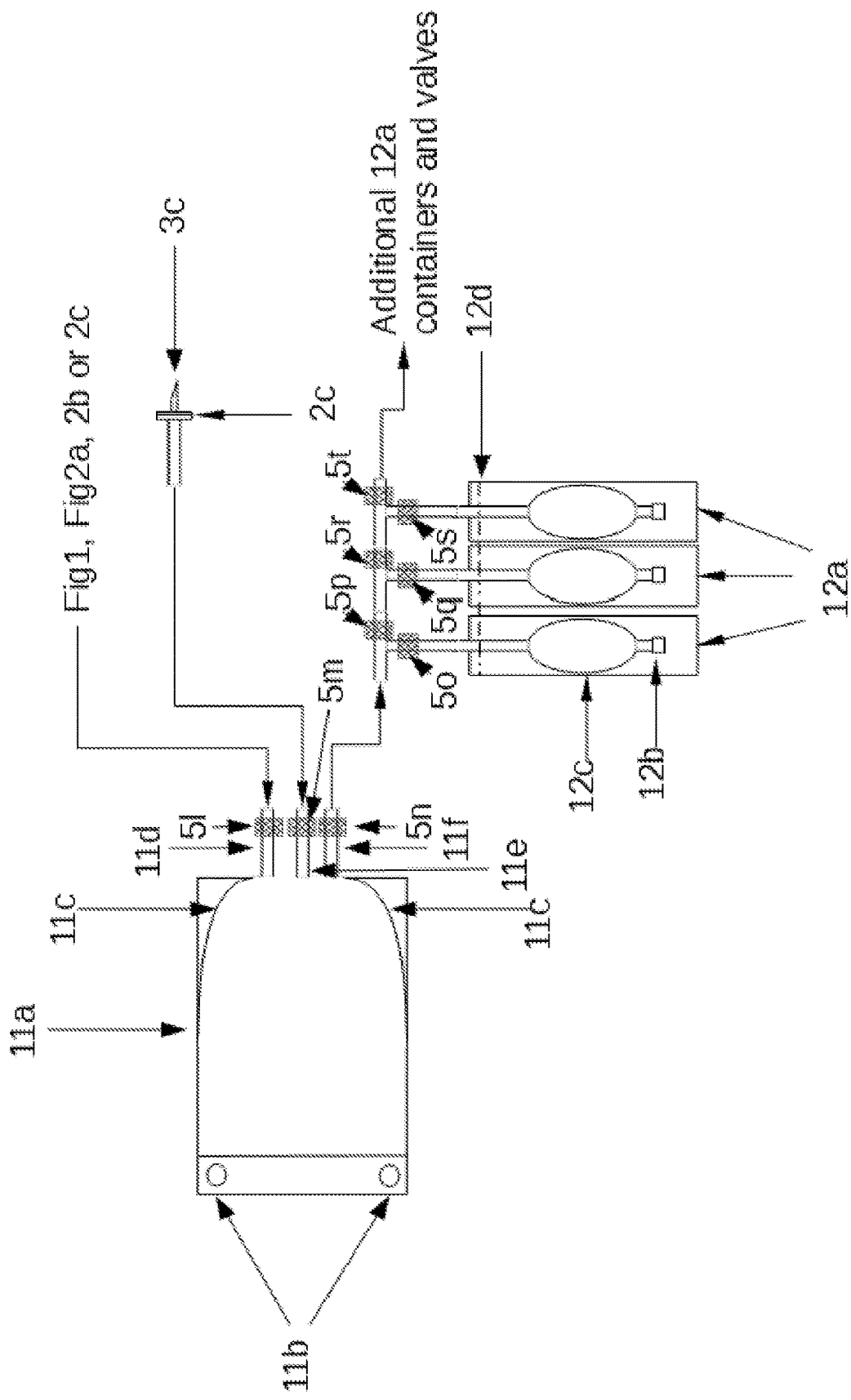
FIG. 3B (also referred to herein as FIG. 3b or FIG. 3b, and the like) depicts an embodiment of the subject matter described herein.

FIG. 2a provides a further example of the invention in which:
2c spike and sterile filter for media
3a in one example short term storage media
3c freezing solution a media required for cryopreservation in one of the examples illustrated in FIG. 2a or FIG. 3b
4c in one example an additional flexible filter module containing filters 4d & 4e
4d in one example FIG. 2a a flexible filter unit may be required for additional size segregation of cell/tissue clumps
4e in one example FIG. 2a a flexible filter unit is required to retain cells but allow the media/cell fragments to be washed out
5d in one example FIG. 2a tubing clamp is in place to stop material from container 1a that has passed though 4a & 4c from returning back to container 1a
5e in one example FIG. 2a tubing clamp is in place to allow waste material from container 1a that has passed through 4a, 4c and 4e to enter container 6a but stop media (3a or 3c) entering via filter 2c from entering container 6a
5f both tubing clamps stop material from container 1a that has passed though filters 4a, 4c and 4e from entering the tubing to the media container (3a or 3c) or transferring to one of the examples FIG. 3(a or b) before the waste has passed into container 6a via 5e. Once the waste has been depleted then tubing clamps 5e and 5d close and both tubing clamps 5f allowing media (3a or 3c) to transfer cells within filter 4e into one of the examples identified in FIG. 3(a or b)
6a a waste container
6b hanging holes to support container 6a FIG. 2b provides yet a further example in which:
5g a tubing clamp in place to allow contents of container 1a to enter the flexible container 7a via filter 4a
5h a tubing clamp in place to allow contents of container 7a to pass through filter 8a retaining and enriching for cells while allowing waste and debris to pass through filter 8b into container 6a with the pressure controlled by valve 8c before the enriched cells return to container 7a via an open clamp 5i
5i a tubing clamp is in place to allow contents of container 7a via open tubing clamp 5h to pass through filter 8a retaining and enriching for cells while allowing waste and debris to pass through filter 8b into container 6a with the pressure controlled by valve 8c before the enriched cells return to container 7a
5j after cell enrichment has occurred then tubing clamp 5h closes and 5j opens allowing contents of 7a to pass on to one of the examples FIG. 3(a or b)
6a a waste container
6b hanging holes to support container 6a
7a a flexible container to receive the contents of: 1a via filter 4a; and filter 8a 7b hanging holes to support container 7a 7c rounded edges on internal container 7a to reduce losses which may occur as part of transfer to examples illustrated in FIG. 3(a or b)

Figure 2C:
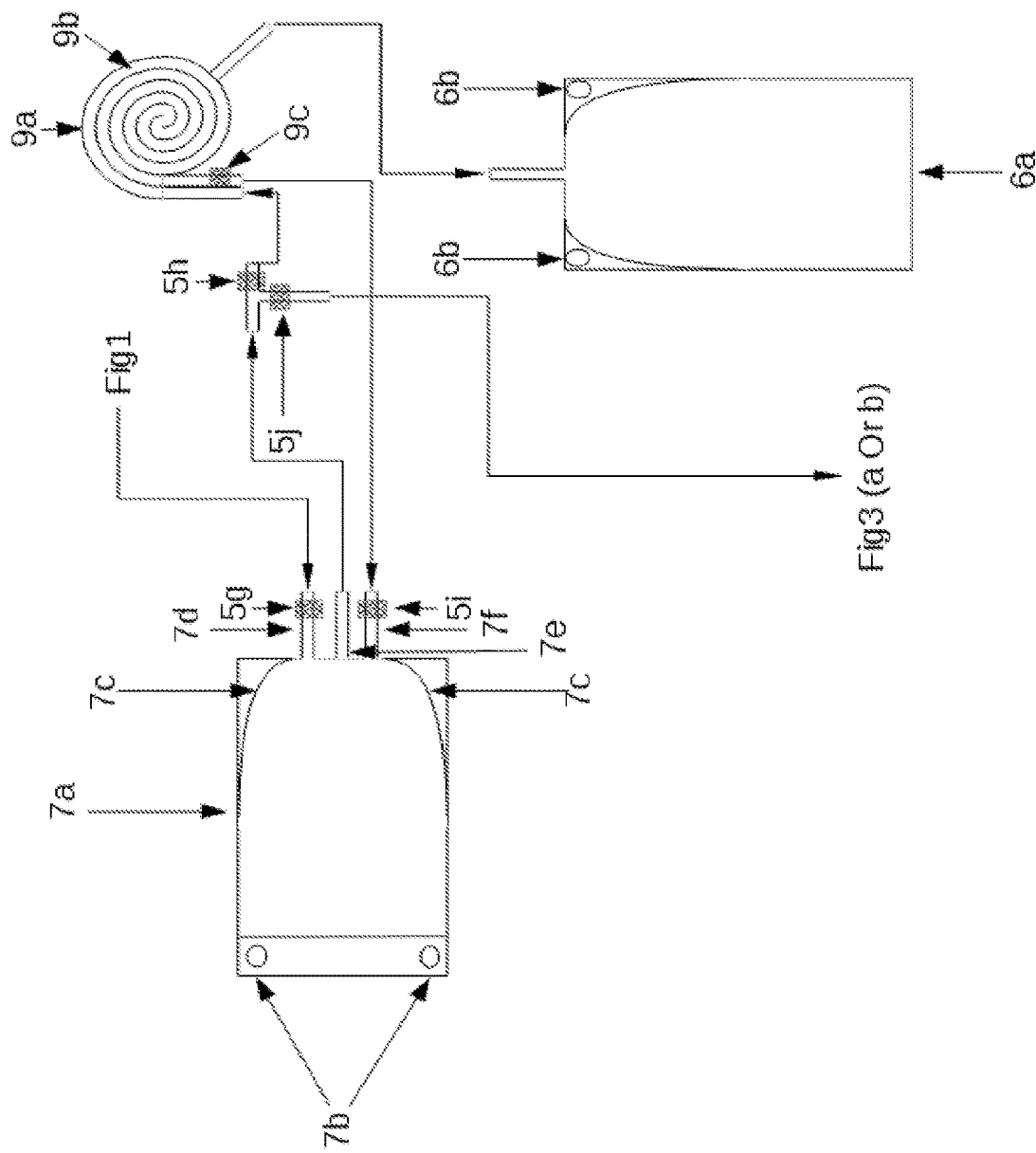
FIG. 2C (also referred to herein as FIG. 2c, FIG. 2c or FIG. 2c, and the like) depicts an embodiment of the subject matter described herein.

7d tubing to allow container 7a to receive the contents of: 1a via filter 4a; and filter 8a 7e tubing to allow contents of container 7a to pass through filter 8a retaining and enriching for cells while allowing waste and debris to pass through filter 8b into container 6a with the pressure controlled by valve 8c before the enriched cells return to container 7a via an open clamp 5i 7f tubing to allow contents of container 7a via open tubing clamp 5h to pass through filter 8a retaining and enriching for cells while allowing waste and debris to pass through filter 8b into container 6a with the pressure controlled by valve 8c before the enriched cells return to container 7a 8a contents of container 7a can be filtered to remove waste media and debris via filter 8b while enriching for cells under the control of valve 8c before returning to container 7a 8b & 8c see 8a In one example, as shown in FIG. 2c it is described that 5g a tubing clamp in place to allow contents of container 1a to enter the flexible container 7a via filter 4a 5h a tubing clamp in place to allow contents of container 7a to pass through filter 9a retaining and enriching for cells while allowing waste and debris to pass through filter 9b into container 6a with the pressure controlled by valve 9c before the enriched cells return to container 7a via an open clamp 5i 5i a tubing clamp is in place to allow contents of container 7a via open tubing clamp 5h to pass through filter 9a retaining and enriching for cells while allowing waste and debris to pass through filter 9b into container 6a with the pressure controlled by valve 9c before the enriched cells return to container 7a 5j after cell enrichment has occurred then tubing clamp 5h closes and 5j opens allowing contents of 7a to pass on to one of the examples FIG. 3(a or b)

6a a waste container 6b hanging holes to support container 6a 7a a flexible container to receive the contents of: 1a via filter 4a; and filter 9a 7b hanging holes to support container 7a 7c rounded edges on internal container 7a to reduce losses which may occur as part of transfer to examples illustrated in FIG. 3(a or b)

7d tubing to allow container 7a to receive the contents of: 1a via filter 4a; and filter 9a 7e tubing to allow contents of container 7a to pass through filter 9a retaining and enriching for cells while allowing waste and debris to pass through filter 9b into container 6a with the pressure controlled by valve 9c before the enriched cells return to container 7a via an open clamp 5i 7f tubing to allow contents of container 7a via open tubing clamp 5h to pass through filter 9a retaining and enriching for cells while allowing waste and debris to pass through filter 9b into container 6a with the pressure controlled by valve 9c before the enriched cells return to container 7a 9a contents of container 7a can be filtered to remove waste media and debris via filter 9b while enriching for cells under the control of valve 9c before returning to container 7a 9b & 9c see 9a FIG. 3a provides yet a further example of the invention in which:

5k a tubing clamp is in place to allow the contents of: 1a (in example FIG. 1 via filter 4a or in example FIG. 2a via filter 4c); or 7a (in example FIG. 2b via filter 8a or in example FIG. 2c via filter 9a) to be transferred into container 10a 10a a flexible container to receive the contents of: 1a via filter 4a (in example FIG. 1) where examples described in FIG. 2(a, b or c) are not required; 1a via filters 4a & 4c (in example FIG. 2a); 7a via filter 8a (in example FIG. 2b); or 7a via filter 9a (in example FIG. 2c)

10b hanging holes to support container 10a 10c rounded edges on internal container 10a to reduce losses which may occur as part of transfer out via 10e or f 10d tubing to enable container 10a to receive the contents of: 1a via filter 4a (in example FIG. 1) where examples described in FIG. 2(a, b or c) are not required; 1a via filters 4a & 4c (in example FIG. 2a); 7a via filter 8a (in example FIG. 2b); or 7a via filter 9a (in example FIG. 2c)

10e tubing to enable contents of container 10a to be withdrawn via connector 10h 10f tubing with a flexible membrane to enable a sterile spike to be introduced via cover 10g to enable contents of container 10a to be withdrawn 10g aseptic cover for tubing containing membrane 10f 10h connector to enable contents of 10a to be withdrawn via tubing 10e In a further example, as shown in FIG. 3b there is provided:

2c spike and sterile filter for media (3c)

3c media required for cryopreservation 5l tubing clamp to allow the contents of: 1a (in example FIG. 1 via filter 4a or in example FIG. 2a via filter 4c); or 7a (in example FIG. 2b via filter 8a or in example FIG. 2c via filter 9a) to be transferred into container 11a 5m tubing clamp to allow media (3c) to enter the flexible container 11a via filter and spike 2c 5n tubing clamp to allow contents of container 11a to enter one of the 12a containers depending on the open or closed status of tubing clamps 5o to 5t 5o-5t tubing clamps to allow contents of container 11a to enter one of the 12a containers depending on the open or closed status of tubing clamps 5o to 5t 11a a flexible container to receive the contents of: 1a via filter 4a (in example FIG. 1) where examples described in FIG. 2(a, b or c) are not required; 1a via filters 4a & 4c (in example FIG. 2a); 7a via filter 8a (in example FIG. 2b); or 7a via filter 9a (in example FIG. 2c)

11b hanging holes to support container 11a 11c rounded edges on internal container 11a to reduce losses which may occur as part of transfer out via 11f 11d tubing to enable container 10a to receive the contents of: 1a via filter 4a (in example FIG. 1) where examples described in FIG. 2(a, b or c) are not required; 1a via filters 4a & 4c (in example FIG. 2a); 7a via filter 8a (in example FIG. 2b); or 7a via filter 9a (in example FIG. 2c)

11e tubing to allow cryopreservation media 3c to be transferred into container 11b 11f tubing to enable the contents of 11a to be transferred to container(s) 12a 12a flexible containers to cryopreserve and store the final disaggregated cells product.

12b a fixture allowing aseptic transfer of the cells out of the container (12a)

Figure 4:
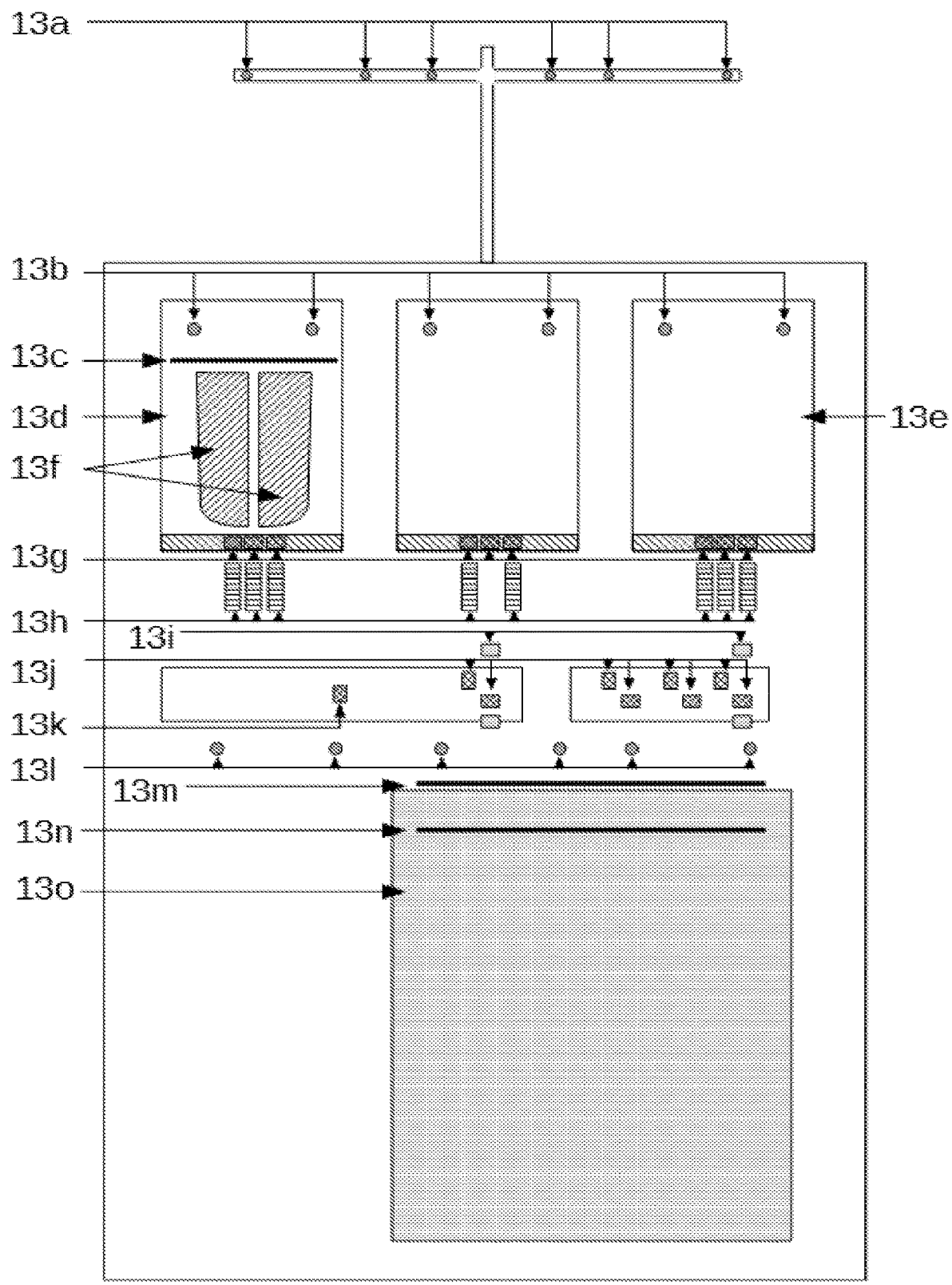
FIG. 4 (also referred to herein as FIG. 4, FIG. 4 or FIG. 4, and the like) depicts an embodiment of the subject matter described herein.

12c a space as part of 12a suitable for the volume to be stored 12d a target location for welding the tubing and secondary flexible container as part of 12a using welder 13n FIG. 4 shows a further example of the device and kit of the invention in which:

13a Pegs for hanging media 3a, 3b, 3c 13b pegs connected to weight sensors for hanging containers 1a and depending on the examples used these could include one or more of: 7a, 10a & 11a. Where the weight sensors are used to define decision stages to control the automated processing of the materials 13c Heat welder to seal container 1a at target site 1d after tissue has been introduced 13d disaggregation module with an opening that can be closed and locked to enable disaggregation and in the example that uses digest enzymes is capable of controlling temperatures between 0° C. and 40° C. to a tolerance of 1° C. to enable digestion. The module also has a built in sensor to assess the level of solid tissue disaggregation by determining the variation in light distribution against time to identify change and thereby identifying completion of the disaggregation process which will occur over a period of seconds to hours.

13e final formulation module with an enclosure to allow temperature control of either container 10a or 11a depending on the example used which is capable of controlling temperatures between 0° C. and ambient environmental temperature to a tolerance of 1° C.

13f disaggregation surfaces which come directly into contact with container 1a and pushes against the back of the module 13d enclosure which can be closed and locked during disaggregation and digestion where enzymes are utilised.

13g tubing clamp 13j tubing clamp 13h peristaltic tubing pumps 13i tubing locators 13k tubing valve required for examples FIGS. 2b & 2c 13l Pegs for hanging containers depending on the examples used these could include one or more of: 6a & 12a 13m tubing welder and cutter required for example FIG. 3b for tubing to container(s) 12a 13n tubing welder required for example FIG. 3b for tubing to container(s) 12a at target location 12d 13o controlled rate cooling module capable of cooling or maintaining any temperature between 8° C. and at least −80° C.

Example Method

The method of the invention is exemplified according to the following process. It is clearly stated that other than the essential features of the method, the various optional steps listed herein can be independently combined to achieve the relevant technical advantages associated with the type of sampling and result to be achieved.

A semi-automatic aseptic tissue processing method comprising: automatically determining aseptic disaggregation tissue processing steps and one or more further tissue processing steps and their associated conditions from a digital tag identifier on an aseptic processing kit, optionally in accordance with the kit described herein; placing a tissue sample into a flexible plastic container of the aseptic processing kit; and processing the tissue sample by automatically executing the one or more tissue processing steps by communicating with and controlling the disaggregation module; the optional enrichment module; and the stabilisation module.

Essentially the process may comprise taking an open ended bag (1st flexible container that is part of disaggregation module) that will receive the biopsy/tissue sample which is already connected via one or more conduits to (conduit) or can be connected via a manual operator controlled aseptic connection to I. a single container with digestion media (2nd flexible container that is part of the disaggregation module) and with or without a stabilisation solution (same 2nd flexible container is part of the stabilisation module also)

II. one container with a digestion solution (2nd flexible container that is part of the disaggregation module) & another container with a stabilisation solution (4th flexible container is part of the stabilisation module)

on addition of the biopsy and sealing of the open ended bag the digestion media can be added via the conduit or aseptic connections (conduit/ports claim 1) and the tissue material processed.

On completion of the digestion by which point the tissue is now a single or small number aggregate cellular suspension the cells can optionally be filtered prior to step 4 (optional enrichment module for filtration comprises the 1st flexible container containing sample and filtered to a 3rd container for receiving the enriched filtrate)

Where the stabilisation media is not present in the same flexible container i.e. option 2.II. this will require the container with stabilisation solution to be added by opening the attached conduit or manual operator controlled aseptically connection to be competed and said connection to be opened enabling in both cases the stabilisation solution to be added before the process continues.

The single or small number aggregate cellular suspension in the original flexible container or which may be optionally subdivided into multiple storage stabilisation containers thereafter are maintained in a stable state on the device and/or will undergo cryopreservation prior to removal for, transport, storage and or used in their ultimately utility. (The stabilisation module also comprises 1st or 3rd container as used in storage/freezing/storage)

In one further non-limiting example of the process:

a) Collection of tissue sample by a separate procedure such as biopsy's or surgery to collect the required tissue material (not part of the invention) is placed into the initial flexible plastic container (see FIG. 1—container 1a).

b) Media (see example FIG. 1—media 3a) is transferred into the disaggregation chamber, or in one example also enters and collects enzymes (see FIG. 1—enzymes 3b), prior to disaggregation using one or more of the following examples of the invention a mechanism such as weight sensors (see FIGS. 1-13b as part of module 13d) will assess the required amount of media to add either determined by: direct operator input or weight of solid tissue.

c) The single use flexible disaggregation container, solid tissue, media and in one example enzymes are combined during a physical disaggregation process for a minimum of a few seconds up to several hours with an optimal time of between 1 and 10 minutes required to break up the solid tissue until there is no visual change (FIG. 5B Table). The disaggregation device is designed to compress the tissues using a variable speed and time depending upon the time taken to disaggregate and feedback via sensors within the disaggregation module (see example FIG. 1-13d).

d) In one embodiment where enzymes are present this will require incubation periods at an optimal temperature of between 30 & 37° C. but could be as low as 0° C. up to 40° C. for at least 1 minute to several hours but more preferable 15 to 45 minutes.

e) Step c and in the embodiment where enzymes step d) can be repeated until the tissue stops changing or the see example has been disaggregated into a liquid cell suspension whichever comes 1st monitored by a sensor in the disaggregation module disaggregation module (FIG. 1-13d).

f) In one embodiment incompletely disaggregated tissues, associated material and impurities are removed enabling enrichment of the cell suspension by passing the disaggregated tissue and media using one or more of the following embodiments:
  i. Direct pass through one or more mechanical filters with holes at least >0.1 μm to 1000 μm but most preferably between 50 and 250 μm and more preferably 100 μm to 200 μm (illustrated in FIG. 2a)
  ii. Density based separation using centrifugation and/or sedimentation with or without a cell aligned density retention solution (e.g. Ficoll-paque GE Healthcare).
  iii. Hydrodynamic filtration where fluid flow and flow obstructing materials enhance the resolution and fractionation of the cells and impurities based on size and shape
  iv. Field flow fractionation where an applied field (e.g. flow, electric, gravitational, centrifugal) acts in a perpendicular or reverse direction to the selection flow (e.g. Tangential flow filtration, Hollow fibre flow filtration, Asymmetric flow filtration, Centrifugal flow filtration). In which case: cells or impurities which are most responsive to the force are driven to the wall where flow is lowest and therefore a long retention time; while cells or impurities which are least responsive to the force remain laminar to the flow and elute quickly (tangential flow filtration illustrated in FIG. 2b & c)
  v. Acoustophoresis where one or more an acoustic frequency (ies) tuned to or harmonized with populations of cells or impurities is used to drive the required cells or impurities in a tangential path to the input stream.

g) In one embodiment the disaggregated enriched tissue product will be resuspended in a fresh media (FIG. 2a using media 3a) such as:
  i. a cell enrichment media in order to undergo an independent targeted enrichment procedure as described previously
  ii. direct cell culture or cold storage media (such as Hypo-Thermosol® from BioLife Solutions.

h) in the embodiment employed in g) the resuspended disaggregated solid tissue derived product will be transferred to one of the embodiment final product containers (illustrated in FIG. 3a) for storage for hours to days prior to being used for its ultimate utility.

i) otherwise after step f) the embodiment (illustrated in FIG. 3b) will apply where the disaggregated solid tissue derived product will undergo re-suspension in a cryoprotectant (FIG. 3b-media 3c) a freezing solution for storage of the disaggregated solid tissue derived product for days to years such as CryoStor® Freezing solution from BioLife Solution.

j) At this stage the disaggregated solid tissue derived product re-suspended in freezing solution using the device (FIG. 4—module 13e) will be transferred to 1 or more flexible cryopreservation container(s) (illustrated in FIG. 3a—container 12a) and in one embodiment of the device it will perform a controlled rate freezing process using the device (FIG. 4—module 13o).

k) After which the bags can be separated from the device and aseptic processing kit for independent storage or distribution.

Figure 6:
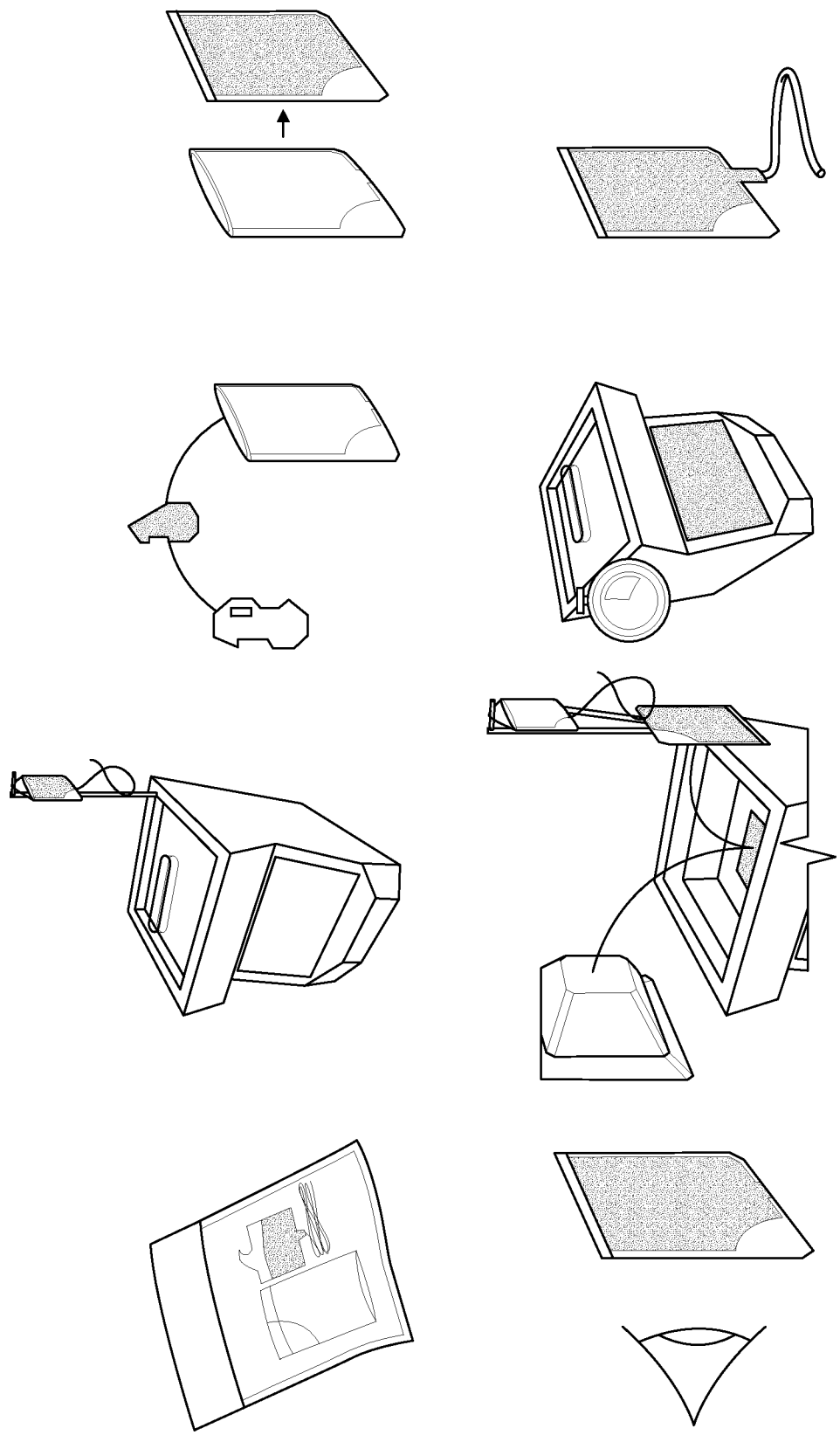
FIG. 6 (also referred to herein as FIG. 6, and the like) depicts an embodiment of the subject matter described herein.
Figure 7:
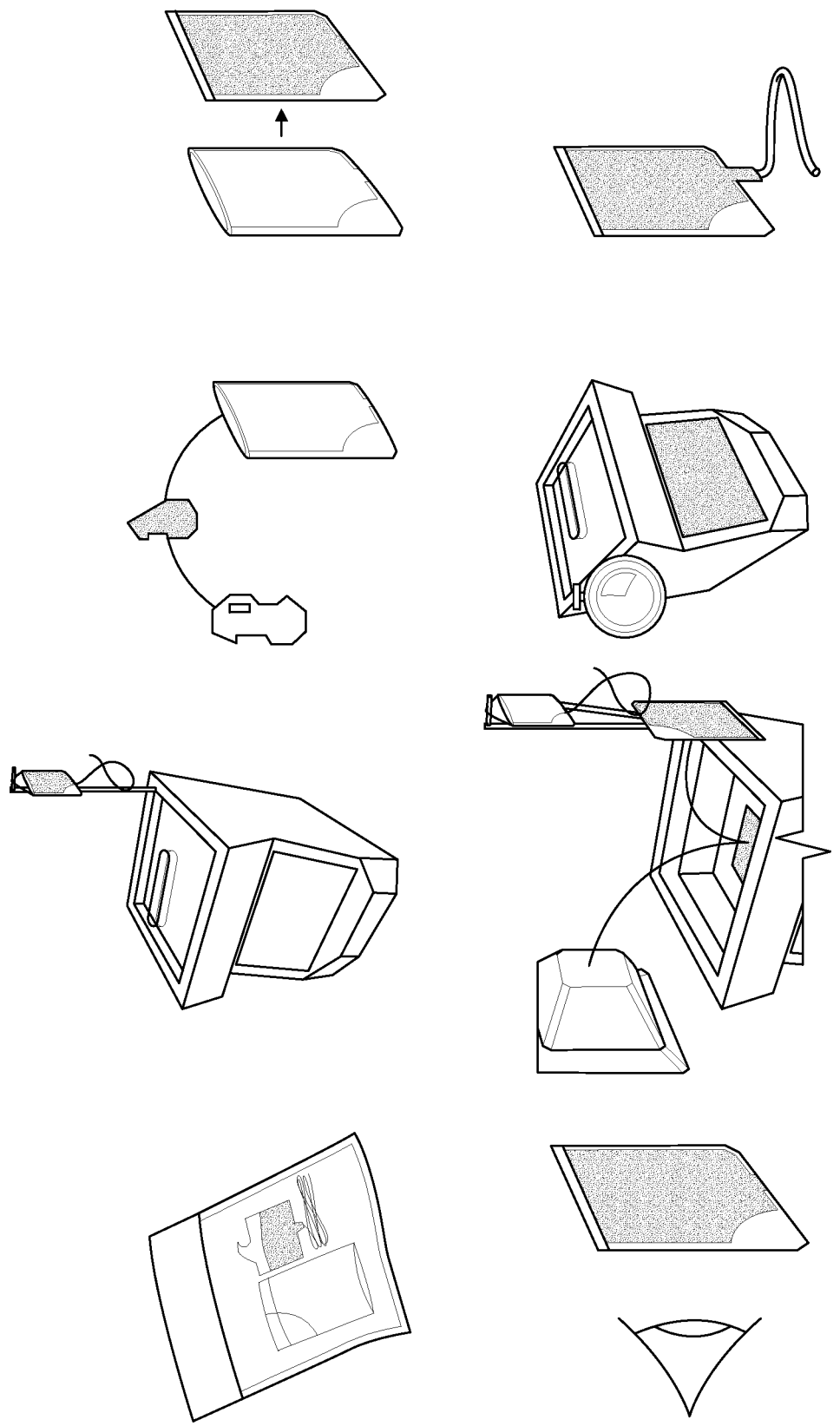
FIG. 7 (also referred to herein as FIG. 7, and the like) depicts an embodiment of the subject matter described herein.

FIGS. 6 and 7 describe further examples in which the disposable kit of the invention can be used with an automatic device for semi-automatic aseptic processing of tissue samples.

FIG. 6 describes the following semi-automatic aseptic tissue processing method using multiple flexible containers for different starting solutions that are part of the modules of the process used for disaggregation and stabilisation.

Process step 1—The user may login to device and scan the tag on the aseptic kit using the device to transfer the automatic processing steps to be used. The device processor recognises the tag and is provided with information needed to carry out the specific processing instructions related to that particular kit.

Process step 2—The digestion media containing flexible bag (part of disaggregation module) and cryo/stabilisation solution containing flexible bag (part of the stabilisation module) are each hung or secured to the device.

Process step 3—The biopsy or tissue sample for processing may be placed into a flexible container (part of both modules) of the aseptic kit via an open end.

Process step 4—The flexible container comprising the sample may then be sealed using a heat weld to close the open end (used to add the sample during initial processing).

Process step 5—The user may then interact with the user interface of the processor to confirm the tissue sample is present and enter any further tissue material specific information, if required.

Process step 6—Digestion media and cryo/stabilisation solution flexible containers are connected with the flexible container housing the sample, after which it maybe placed into the device for automatic processing.

Process step 7—The device executes the cycles according to the kit information undertaking disaggregation of the sample and stabilisation/cryo preservation of resulting cells.

Process step 8—When stabilised/frozen disconnect and discard used media and cryo/stabilisation containers of kit. Tissue processed into single or multi-cell solution in flexible container is disconnected before transferring into storage or transport container prior to its ultimate utilisation.

FIG. 7 describes how flexible containers comprising the media used in the process may be shared between the modules of the aseptic processing kit and method.

Process step 1—The user may login to device and scan the tag on the aseptic kit using the device to transfer the automatic processing steps to be used.

Process step 2—A flexible bag (part of disaggregation/stabilisation module) comprising both the media and cryo/stabilisation solution is hung or otherwise secured to the device.

Process step 3—The biopsy or tissue sample for processing may be placed into a further flexible container (part of both modules) of the aseptic kit via an open end.

Process step 4—The flexible container comprising the sample may then be sealed using a heat weld to close the open end.

Process step 5—The user may then interact with the user interface of the processor to confirm the tissue sample is present and enter any tissue material specific information, if required.

Process step 6—Digestion media and cryo/stabilisation solution flexible container is connected with the flexible container housing the sample, after which it maybe placed into the device for automatic processing.

Process step 7—The device cycles to enable disaggregation of the sample and stabilisation of resulting cells, optionally via cryopreservation.

Process step 8—When freezing/stabilising is complete the user disconnects and discard used flexible containers of kit. Tissue processed into single or multi-cell solution in the remaining flexible container is disconnected before transferring into storage or transport container prior to its ultimate utilisation.

Enzymatic Digestion

By way of example, in another embodiment of the method of the invention, where the disaggregation process is being supplemented with enzymatic digestion the media formulation for enzymatic digestion must be supplemented with enzymes that aid in protein breakdown causing the cell to cell boundaries to breakdown as described above.

Media Formulation for Enzymatic Digestion

Various liquid formulations known in the art of cell culturing or cell handling can be used as the liquid formulation used for cell disaggregation and enzymatic digestion of solid tissues, including but not limited to one or more of the following media Organ Preservation Solutions, selective lysis solutions, PBS, DMEM, HBSS, DPBS, RPMI, Iscove's medium, X-VIVO™, AIM-VT™, Lactated Ringer's solution, Ringer's acetate, saline, PLASMALYTE™ solution, crystalloid solutions and IV fluids, colloid solutions and IV fluids, five percent dextrose in water (D5W), Hartmann's SolutionDMEM, HBSS, DPBS, RPMI, AIM-VT™, Iscove's medium, X-VIVO™, each can be optionally supplemented with additional cell supporting factors e.g. with foetal calf serum, human serum or serum substitutes or other nutrients or Cytokines to aid in cell recovery and survival or specific cell depletion. The media can be standard cell media like the above mentioned media or special media for e.g. primary human cell culture (e.g. for endothelia cells, hepatocytes or keratinocytes) or stem cells (e.g. dendritic cell maturation, hematopoietic expansion, keratonocytes, mesenchymal stem cells or T cells). The media may have supplements or reagents well known in the art, e.g. albumins and transport proteins, amino acids and vitamins, metal-ion(s), antibiotics, attachments factors, de-attachment factors, surfactants, growth factors and cytokines, hormones or solubilising agents. Various media are commercially available e. g. from ThermoFisher, Lonza or Sigma-Aldrich or similar media manufacturers and suppliers.

The liquid formulation required for enzymatic digestion must have sufficient calcium ions present in the of at least 0.1 mM up to 50 mM with an optimal range of 2 to 7 mM ideally 5 mM.

The solid tissue to be digested can be washed after disaggregation with a liquid formulation containing chelating agents EGTA and EDTA to remove adhesion factors and inhibitory proteins prior to washing and removal of EDTA and EGTA prior to enzymatic digestion.

The liquid formulation required for enzymatic digestion is more optimal with minimal chelating agents EGTA and EDTA which can severely inhibit enzyme activity by removing calcium ions required for enzyme stability and activity. In addition β-mercaptoethanol, cysteine and 8-hydroxyquinoline-5-sulfonate are other known inhibitory substances.

Cryopreservation

As described in preferred embodiments final cell container for cryopreservation is a flexible container manufactured from resilient deformable material. In this embodiment of the device the final container is either transferred directly to a freezer −20 to −190° C. or more optimally located in the controlled rate freezing apparatus either associated with the device or supplied separately (manufactured by for example Planer Products or Asymptote Ltd) in which the temperature of the freezing chamber and the flexible storage container(s) employed to contain the enriched disaggregated solid tissue container is controlled either by: injecting a cold gas (normally nitrogen for example Planer products); or by removing heat away from the controlled cooling surface(s). Both methods result in the ability to accurately control with an error of less than 1° C. or more preferable 0.1° C. the freezing process at the required rate for the specific cell(s) to be frozen based on the freezing solution and the desired viability of the product. This cryopreservation process must take into account the ice nucleation temperature which is ideally as close as possible to the melting temperature of the freezing solution. Followed by crystal growth in an aqueous solution, water is removed from the system as ice, and the concentration of the residual unfrozen solution increases. As the temperature is lowered, more ice forms, decreasing the residual non-frozen fraction which further increases in concentration. In aqueous solutions, there exists a large temperature range in which ice co-exists with a concentrated aqueous solution. Eventually through temperature reduction the solution reaches the glass transition state at which point the freezing solution and cells move from a viscous solution to a solid-like state below this temperature the cells can undergo no further biological changes and hence are stabilised, for years potentially decades, until required.

Further Applications of the Invention

The disaggregated cell products achieved by the method of the present invention can be cultured and/or analysed (characterised) according to all methods known to the person skilled in the art.

The cells obtainable by the methods disclosed herein may be used for subsequent steps such as research, diagnostics, tissue-banks, biobanks, pharmacological or clinical applications known to the person skilled in the art. Cells can then be taken into culture using a Medium optimized for this application, e.g. T cell Mixed Media (Cellular Therapeutics) usually containing but not limited to growth factors such as IL-2, IL-7, IL-15, IL-21 or stimulatory conditions such as plates or polystyrene beads coated with antibodies. In the present invention isolated cells were seeded into culture containers and maintained using procedures standardly used by a person skilled in the art such as a humidified atmosphere (1-20% usually 5% CO2, 80 to 99% usually 95% air) at temperatures between 1 to 40 usually 37° C. for several weeks and supplements may be added supplemented with 10% FBS and 3000 IU/mL IL-2.

Such cell cultures can be used to study e.g. cell function, tumour cell killing, cell signalling, biomarkers, cell pathways, nucleic acids, and other cell or tissue related factors that may be used to identify donor, tissue, cell or nucleic acid status.

The enriched cells could be used before and/or after cell culturing as a pharmaceutical composition in the therapy, e.g. cellular therapy, or prevention of diseases. The pharmaceutical composition can be used for the treatment and/or prevention of diseases in mammals, especially humans, possibly including administration of a pharmaceutically effective amount of the pharmaceutical composition to the mammal.

The disease may be any disease, which can be treated and/or prevented through the presence of solid tissue derived cells and/or through increasing the concentration of the relevant cells in/at the relevant place, i.e. the tumours or sites of disease. The treated and/or preventively treated disease may be any disorder, e.g. cancer or a degenerative disorder. The treatment may be the transplantation of enriched, engineered or expanded cells or any combination of these and either administered to the relevant part of the body or supplied systemically.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

FURTHER SPECIFIC EXAMPLES

Example 1

Impact of the Length of Disaggregation

Figure 5A:
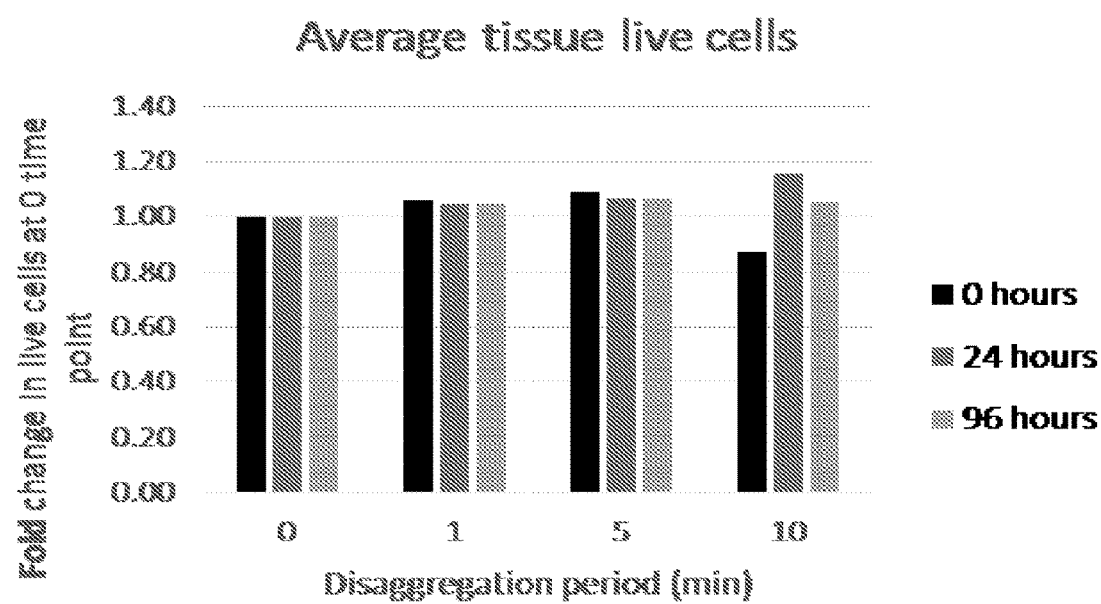
FIG. 5A (also referred to herein as FIG. 5A, and the like) depicts the average tissue live cells over time.

Peripheral blood mononuclear cells were physically disaggregated for 0, 1, 5 & 10 minutes continuously before a being cultured in vitro for 0, 24 & 96 hours to assess cell recovery. The results demonstrate the physical process has negligible impact over 1 or 5 minutes and at 10 minutes the impact was transient where and initial reduction in viable cells at 0 hours was equivalent to non-disaggregated cells at 24 & 96 hours (FIG. 5A).

Example 2

Solid Tissue Sample Size, Volume of Digestion Media, Disaggregation and Incubation Times Conditions of: Solid tissue size, volume of digestion media, disaggregation time and incubation conditions have been tested and demonstrate full disaggregation of solid tissue (FIG. 5B) except where the volume of digestion media cushioned the solid tissue during the disaggregation process resulting in 30-50% of the solid tissue remaining intact.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs.

The foregoing description has been presented only for the purposes of illustration and is not intended to limit the disclosure to the precise form disclosed, but by the claims appended hereto.

Non-Patent Literature Cited

Miller R G and Phillips R A. Separation of cells by velocity sedimentation. J Cell Physiol 1969; 73: 191-201

Buckner D, Graw R G, Eisel R J, et al. Leukapheresis by continuous flow centrifugation (CFC) in patients with chronic myelocytic leukemia (CML). Blood 1969; 33: 353-369

Liu W, Hou Y, Chen H, et al. Sample preparation method for isolation of single-cell types from mouse liver for proteomic studies. Proteomics 2011; 11: 3556-3564

Nagase K, Kimura A, Shimizu T, et al. Dynamically cell separating thermo-functional biointerfaces with densely packed polymer brushes. J Mater Chem 2012; 22: 19514-19522

Rembaum A, Yen R C K, Kempner D H, et al. Cell labelling and magnetic separation by means of immunoreagents based on polyacrolein microspheres. J Immunol Methods 1982; 52: 341-351.

Cahoy J D, Emery B, Kaushal A, et al. A transcriptome database for astrocytes, neurons, and oligodendrocytes: a new resource for understanding brain development and function. J Neurosci 2008; 28:264-278

Miltenyi S, Müller W, Weichel W, et al. High gradient magnetic cell separation with MACS. Cytometry 1990; 11:231-238.

Topalian S L, Muul L M, Solomon D, et al. Expansion of human tumor infiltrating lymphocytes for use in immunotherapy trials. J Immunol Methods. 1987; 102(1):127-41.

Bonner W A, Sweet R G, Hulett H R, et al. Fluorescence activated cell sorting. Rev Sci Instrum 1972; 43: 404-409

Gossett D R, Weaver W M, Mach A J. Et al., Label-free cell separation and sorting in microfluidic systems, Anal Bioanal Chem, 2010,397, 3249-3267

Bárbara Cunha B, Peixoto C, Silva M M, et al., Filtration methodologies for the clarification and concentration of human mesenchymal stem cells, J. of Membrane Sci., 2015,478, 117-129

Klein A B, Witonsky S G, Ahmed S A, et al. Impact of different cell isolation techniques on lymphocyte viability and function. J Immunoassay Immunochem 2006; 27: 61-76

Steinberg M S. 'ECM': its nature, origin and function in cell aggregation. Exp Cell Res 1963; 30: 257-279.

Hefeneider S H, McCoy S L, Morton J I, et al. DNA binding to mouse cells is mediated by cell-surface molecules: the role of these DNA-binding molecules as target antigens in murine lupus. Lupus 1992; 1: 167-173.

Pisetsky D S and Fairhurst A-M. The origin of extracellular DNA during the clearance of dead and dying cells—review. Autoimmunity 2007; 40: 281-284

Renner W A, Jordan M, Eppenberger H M, et al. Cell-cell adhesion and aggregation: influence on the growth behaviour of CHO cells. Biotechnol Bioeng 1993; 41: 188-193

Shedlock D J, Aviles J, Talbott K T et al., Induction of Broad Cytotoxic T Cells by Protective DNA Vaccination Against Marburg and Ebola. Molecular Therapy, 2013; 21, 1432-1444

Baust J G, & Baust J M, Advances in Biopreservation, 2006, Chapt. 8, 157-196

Seglen, P. O., Preparation of Isolated Rat Liver Cells, Methods in Cell Biology, 1976; 13, 29

Quistorff, B., Dich, J., & Grunnet, N. Preparation of isolated rat liver hepatocytes. Methods in molecular biology, Chapt 14, 1990; 151-160.

Seifter, S., Gallop, P. M., Klein, L., et al. Studies on Collagen, Part II. Properties of Purified Collagenase and Its Inhibition. J. Biol. Chem. 1959; 234:285

The invention claimed is:

1. A method of aseptic tissue processing to prepare T-cells from a sample, comprising:
   obtaining a sample that has not been previously cryopreserved comprising cancer cells and T-cells contained in a closed flexible bag for disaggregation comprising at least one port;
   aseptically transferring media enzyme solution into the closed flexible bag for disaggregation through a port in the closed flexible bag for disaggregation;
   subjecting the sample contained in the closed flexible bag for disaggregation to physical and enzymatic disaggregation to disaggregate into single cell or small number aggregate cellular suspensions comprising T-cells;

aseptically separating the single cell or small number aggregate cellular suspensions comprising T-cells and transferring the single cell or small number aggregate cellular suspensions comprising T-cells through a port into a closed flexible bag for cell culture;

aseptically transferring a culture medium for T-cell expansion into the closed flexible bag for cell culture through a port in the closed flexible bag for cell culture; and, culturing the T-cells in the closed flexible bag for cell culture.

2. The method of claim 1, wherein the flexible bag for disaggregation further contains cell media.

3. The method of claim 1, wherein the media enzyme solution is selected from the group consisting of collagenase, trypsin, lipase, hyaluronidase, deoxyribonuclease, Liberase H1 and pepsin, and or mixtures thereof.

4. The method of claim 3, wherein the media enzyme solution comprises collagenase and deoxyribonuclease.

5. The method of claim 1, wherein the subjecting the sample to physical and enzymatic disaggregation to disaggregate into single cell or small number aggregate cellular suspensions comprising T-cells comprises mechanically crushing, shearing or compressing the sample.

6. The method of claim 5, wherein the method comprises compressing the sample.

7. The method of claim 5, wherein the subjecting the sample to physical and enzymatic disaggregation is from a few seconds to several hours.

8. The method of claim 7, wherein the subjecting the sample to physical and enzymatic disaggregation is from about 15 to about 45 minutes.

9. The method of claim 5, wherein subjecting the sample to physical and enzymatic disaggregation is at a temperature of from about 0° C. to about 40° C.

10. The method of claim 9, wherein subjecting the sample to physical and enzymatic disaggregation is at a temperature of from about 30° C. to about 37° C.

11. The method of claim 1, wherein the aseptically separating single cell or small number aggregate cellular suspensions comprising T-cells is selected from the group consisting of density based separation, hydrodynamic filtration, field flow fractionation, acoustopheresis and filtration.

12. The method of claim 11, wherein the aseptically separating single cell or small number aggregate cellular suspensions comprising T-cells is filtration.

13. The method of claim 12, wherein the filtration comprises passing the disaggregated tissue and media through one or more filters.

14. The method of claim 13, wherein the one or more filters are mechanical filters with holes from about 50 p.m to about 250 p.m.

15. A method of aseptic tissue processing to isolate single cell or small number aggregate cellular suspensions for T-cell expansion, comprising:

obtaining a sample that has not been previously cryopreserved comprising solid tumor tissue and T-cells contained in a closed flexible bag for disaggregation comprising at least one port;

aseptically transferring media enzyme solution comprising collagenase into the closed flexible bag for disaggregation through a port in the closed flexible bag for disaggregation;

subjecting the sample contained in the closed flexible bag for disaggregation to physical and enzymatic disaggregation to disaggregate into single cell or small number aggregate cellular suspensions comprising T-cells, wherein:

the single cell is of a spheroid shape having a diameter from about 7 μm to about 20 μm; and, the physical and enzymatic disaggregation comprises mechanical compression cycles at a temperature of from about 30° C. to about 37° C. for about 15 to about 45 minutes;

aseptically filtering the single cell or small number aggregate cellular suspensions comprising T-cells through a mechanical filter with holes from about 50 μm to about 250 μm, and aseptically transferring the filtered single cell or small number aggregate cellular suspensions comprising T-cells through a port into a closed flexible bag for cell culture;

aseptically transferring a culture medium for T-cell expansion into the closed flexible bag for cell culture through a port in the closed flexible bag for cell culture; and, culturing the T-cells in the closed bag for cell culture.

* * * * *

UNITED STATES PATENT AND TRADEMARK OFFICE
CERTIFICATE OF CORRECTION

PATENT NO. : 11,618,878 B2  
APPLICATION NO. : 17/826062  
DATED : April 4, 2023  
INVENTOR(S) : Guest Page 1 of 1

It is certified that error appears in the above-identified patent and that said Letters Patent is hereby corrected as shown below:

In the Claims

Column 24,
Lines 8-9, Claim 14 "50 p.m to about 250 p.m." should read --50 µm to about 250 µm.--.

Signed and Sealed this  
Fourteenth Day of November, 2023

Katherine Kelly Vidal  
*Director of the United States Patent and Trademark Office*